United States Patent
Klausen et al.

(10) Patent No.: US 10,986,850 B2
(45) Date of Patent: Apr. 27, 2021

(54) POLYPEPTIDES HAVING LYSOZYME ACTIVITY, POLYNUCLEOTIDES ENCODING SAME AND USES AND COMPOSITIONS THEREOF

(71) Applicant: Novozymes A/S, Bagsvaerd (DK)

(72) Inventors: Mikkel Klausen, Copenhagen (DK); Kirk Matthew Schnorr, Holte (DK); Lars Kobberoee Skov, Ballerup (DK); Soeren Nymand-Grarup, Copenhagen (DK); Marianne Thorup Cohn, Copenhagen (DK); Peter Bjarke Olsen, Copenhagen (DK); Ming Li, Beijing (CN); Ye Liu, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/463,205

(22) PCT Filed: Dec. 21, 2017

(86) PCT No.: PCT/CN2017/117753
§ 371 (c)(1),
(2) Date: May 22, 2019

(87) PCT Pub. No.: WO2018/113743
PCT Pub. Date: Jun. 28, 2018

(65) Prior Publication Data
US 2019/0328005 A1 Oct. 31, 2019

(30) Foreign Application Priority Data

Dec. 21, 2016 (WO) ................ PCT/CN2016/111320
Mar. 8, 2017 (WO) ................ PCT/CN2017/075960

(51) Int. Cl.
| | |
|---|---|
| *A23K 20/189* | (2016.01) |
| *A23K 20/174* | (2016.01) |
| *A23K 20/22* | (2016.01) |
| *A23K 20/24* | (2016.01) |
| *A23K 20/20* | (2016.01) |
| *A23K 50/30* | (2016.01) |
| *A23K 50/75* | (2016.01) |
| *A23K 10/30* | (2016.01) |
| *C12N 9/36* | (2006.01) |

(52) U.S. Cl.
CPC ............ *A23K 20/189* (2016.05); *A23K 10/30* (2016.05); *A23K 20/174* (2016.05); *A23K 20/22* (2016.05); *A23K 20/24* (2016.05); *A23K 20/30* (2016.05); *A23K 50/30* (2016.05); *A23K 50/75* (2016.05); *C12N 9/2462* (2013.01); *C12Y 302/01017* (2013.01)

(58) Field of Classification Search
None
See application file for complete search history.

(56) References Cited

U.S. PATENT DOCUMENTS

| | | | |
|---|---|---|---|
| 2016/0030528 A1 | 2/2016 | Metcalf | |
| 2019/0351032 A1* | 11/2019 | Kjaerulff | ................. A23L 33/18 |
| 2020/0305465 A1* | 10/2020 | Aureli | .................... A23K 50/75 |

FOREIGN PATENT DOCUMENTS

| | | |
|---|---|---|
| EP | 2904912 A1 | 8/2015 |
| WO | 2005/011587 A2 | 2/2005 |
| WO | 2005/080559 A1 | 9/2005 |
| WO | 2009/102755 A1 | 8/2009 |
| WO | 2011/104339 A1 | 9/2011 |
| WO | 2012/027374 A2 | 3/2012 |
| WO | 2012/035103 A1 | 3/2012 |
| WO | 2013/076253 A1 | 5/2013 |
| WO | 2013/076259 A2 | 5/2013 |
| WO | 2013/110627 A1 | 8/2013 |
| WO | 2016/210238 A1 | 12/2016 |
| WO | 2017/001701 A1 | 1/2017 |

OTHER PUBLICATIONS

Schnorr et al, EBI Accession No. BAP10817 (2013).
Visser et al., EBI Accession No. AZT73868 (2012).
Mondo et al., EBI Accession No. A0A1Y1Z9R4 (2017).
Baroncelli et al., NCBI Reference No. XP_018657583.1 (2016).
Berka et al., NCBI Reference No. XP_003650266.1 (2012).
Berka et al., NCBI Reference No. XP_003662567.1 (2012).
Berka et al., UniProt Accession No. G2QWF5 (2016).
Birren et al., NCBI Reference No. XP_001215317.1 (2008).
Corrochano et al., NCBI Reference No. XP_018287694.1 (2016).
Galagan et al., NCBI Reference No. XP_964535.1 (2015).
Jimenez et al., GenBank Accession No. OIW26653.1 (2016).
Kanematsu et al., GenBank Accession No. GAP89829.1 (2015).
Kohler et al., GenBank Accession No. KIJ42223.1 (2015).
Kohler et al., GenBank Accession No. KIN06446.1 (2015).
Kohler et al., GenBank Accession No. KIN08373.1 (2015).
Korczynska et al., Acta Crystallographica Section F, vol. F66, pp. 973-977 (2010).
Kubicek et al., NCBI Reference No. XP_013942670.1 (2015).
Li et al., UniProt Accession No. A0A0A2VUR3 (2015).
Linde et al., GenBank Accession No. CDS02619 (2015).
Masschalck et al., Journal of Food Protection, vol. 65, No. 12, pp. 1916-1923 (2002).
Meinhardt et al., NCBI Reference No. XP_007849295.1 (2014).
Morin et al., NCBI Reference No. XP_006463298.1 (2014).
Nierman, NCBI Reference No. XP_001276751.1 (2008).
Nowrousian et al., NCBI Reference No. XP_003352547.1 (2011).
Peter et al., GenBank Accession No. OCK75562.1 (2016).

(Continued)

*Primary Examiner* — Iqbal H Chowdhury
(74) *Attorney, Agent, or Firm* — Elias Lambiris

(57) ABSTRACT

Animal feed or animal feed additives comprising one or more polypeptides having lysozyme activity are disclosed. Polypeptides having lysozyme activity, polynucleotides encoding the polypeptides, nucleic acid constructs, vectors, and host cells comprising the polynucleotides as well as methods of producing and using the polypeptides are also provided.

18 Claims, 1 Drawing Sheet

Specification includes a Sequence Listing.

(56) References Cited

OTHER PUBLICATIONS

Priebe et al., GenBank Accession No. CEJ53659.1 (2015).
Priebe et al., GenBank Accession No. CEL10138.1 (2016).
Riley et al., GenBank Accession No. KDQ07276.1 (2014).
Shang et al., GenBank Accession No. OAA73042.1 (2016).
Shang et al., GenBank Accession No. OAA81279.1 (2016).
Shang et al., UniProt Accession No. A0A162JSB9 (2016).
Sun et al., Nature Communications, vol. 8322, No. 6, pp. 1-12 (2015).
Terfehr et al., GenBank Accession No. KFH43569.1 (2014).
Wang et al., NCBI Reference No. XP_018138018.1 (2016).
Wang et al., NCBI Reference No. XP_018142497.1 (2016).
Wang et al., NCBI Reference No. XP_018175238.1 (2016).
Wang et al., UniProt Accession No. A0A179GAU8 (2017).
Zeiner et al., NCBI Reference No. XP_018032810.1 (2016).

\* cited by examiner

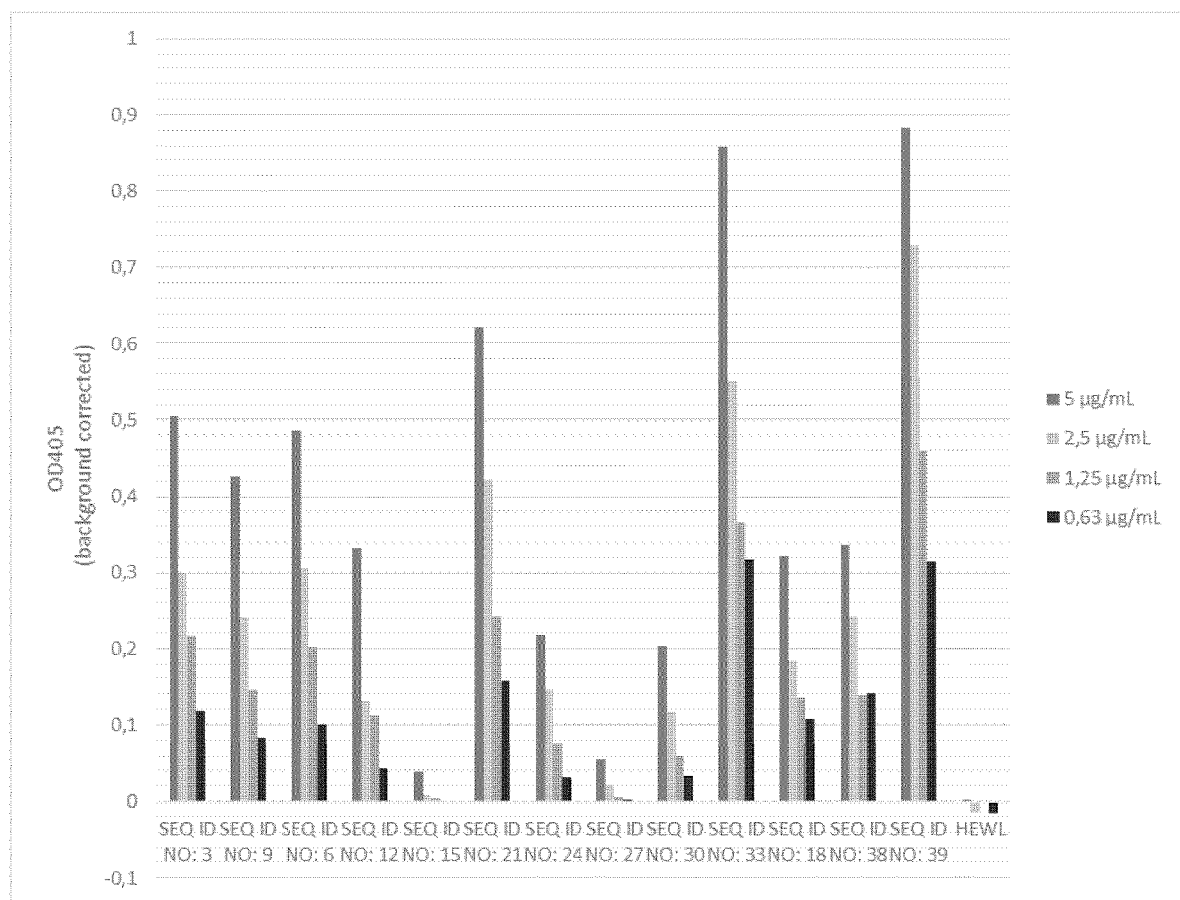

POLYPEPTIDES HAVING LYSOZYME ACTIVITY, POLYNUCLEOTIDES ENCODING SAME AND USES AND COMPOSITIONS THEREOF

CROSS-REFERENCE TO RELATED APPLICATIONS

This application is a 35 U.S.C. 371 national application of international application no. PCT/CN2017/117753 filed Dec. 21, 2017, which claims priority or the benefit under 35 U.S.C. 119 of International application nos. PCT/CN2016/111320 and PCT/CN2017/075960 filed Dec. 21, 2016 and Mar. 8, 2017, respectively. The content of each application is fully incorporated herein by reference.

REFERENCE TO A SEQUENCE LISTING

This application contains a Sequence Listing in computer readable form, which is incorporated herein by reference.

FIELD OF THE INVENTION

The present invention relates animal feed or animal feed additives comprising one or more polypeptides having lysozyme activity. The invention also relates to polypeptides having lysozyme activity, polynucleotides encoding the polypeptides nucleic acid constructs, vectors, and host cells comprising the polynucleotides as well as methods of producing and using the polypeptides.

BACKGROUND OF THE INVENTION

Lysozyme is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse as a result of unbalanced osmotic pressure.

Lysozyme naturally occurs in many organisms such as viruses, plants, insects, birds, reptiles and mammals. In mammals, Lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms.

Lysozyme has been classified into five different glycoside hydrolase (GH) families (CAZy, cazy.orq): hen egg-white lysozyme (GH22), goose egg-white lysozyme (GH23), bacteriophage T4 lysozyme (GH24), *Sphingomonas* flagellar protein (GH73) and *Chalaropsis* lysozymes (GH25). Lysozymes from the families GH23 and GH24 are primarily known from bacteriophages and have recently been identified in fungi. The lysozyme family GH25 has been found to be structurally unrelated to the other lysozyme families.

Lysozyme extracted from hen egg white is the primary product available on the commercial market, but does not cleave N,6-O-diacetylmuramic acid in e.g. *Staphylococcus aureus* cell walls and is thus unable to lyse this important human pathogen among others (Masschalck B, Deckers D, Michiels C W (2002), "Lytic and nonlytic mechanism of inactivation of gram-positive bacteria by lysozyme under atmospheric and high hydrostatic pressure", *J Food Prot.* 65(12): 1916-23).

Antimicrobial growth promoters (AGP's) have traditionally been used for growth promotion in animals, and probably work by preventing low level infections by pathogens such as *Clostridium perfringens*. However, AGP's are increasingly being banned worldwide and therefore new solutions to promote animal growth but which are not AGP's are of interest.

WO2013/076253 and WO2005/080559 disclose GH25 lysozymes for use in animal feed. However, said lysozymes are not highly active in degrading the cell wall from *Micrococcus lysodeikticus* (a typical lysozyme activity assay) and more active lysozymes would be desired. The object of the present invention is to provide new and more active lysozymes which could be suitable for animal health.

SUMMARY OF THE INVENTION

The invention relates to polypeptides which have improved lysozyme activity against the peptidoglycans found in the cell walls of *Micrococcus lysodeikticus*. The lysozymes of the invention are all GH25 lysozymes and all have improved ability to lyse bacterial cell walls of *Micrococcus lysodeikticus*, thereby rendering them suitable for use in animal feed to improve the animal health. The lysozymes of the invention have improved activity compared to the lysozyme described in WO2013/076253 (it is described herein as SEQ ID NO 39). A large subset of the GH25 lysozymes have surprisingly been found to furthermore have lysozyme activity against *Lactobacillus johnsonii*. *Lactobacillus johnsonii* is an important bacterium of the intestinal flora of animals. Without being bound to a particular theory, it is believed that removal of dead *Lactobacillus johnsonii* cells from the intestinal flora, by means of enzymatic lyses of the partially degraded bacterial cell wall, to be an important contributor to intestinal health of an animal.

An aspect of the invention is directed to an isolated GH25 polypeptide having lysozyme activity selected from the group consisting of:
(a) a polypeptide having at least 90% sequence identity to the polypeptide of SEQ ID NO: 3;
(b) a polypeptide having at least 80% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 80% sequence identity to the polypeptide of SEQ ID NO: 30;
(k) a polypeptide having at least 80% sequence identity to the polypeptide of SEQ ID NO: 33;
(l) a polypeptide having at least 83% sequence identity to the polypeptide of SEQ ID NO: 38;
(m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(n) a polypeptide comprising the polypeptide of (a), (b), (c), (d), (e), (f), (g), (h), (i), (j), (k), (l) or (m) and a N-terminal and/or C-terminal His-tag and/or HQ-tag;
(o) a polypeptide comprising the polypeptide of (a), (b), (c), (d), (e), (f), (g), (h), (i), (j), (k), (l) or (m) and a N-terminal and/or C-terminal extension of between 1 and 10 amino acids; and
(p) a fragment of the polypeptide of (a), (b), (c), (d), (e), (f), (g), (h), (i), (j), (k), (l) or (m) having lysozyme activity and having at least 90% of the length of the mature polypeptide.

A further aspect of the invention relates to isolated GH25 polypeptide having lysozyme activity selected from the group consisting of:
(a) a polypeptide having at least 90% sequence identity to the polypeptide of SEQ ID NO: 3;
(b) a polypeptide having at least 80% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(k) a polypeptide having at least 80% sequence identity to the polypeptide of SEQ ID NO: 33;
(l) a polypeptide having at least 83% sequence identity to the polypeptide of SEQ ID NO: 38;
(m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(n) a polypeptide comprising the polypeptide of (a), (b), (c), (d), (f), (g), (h), (i), (j), (k), (l) or (m) and a N-terminal and/or C-terminal His-tag and/or HQ-tag;
(o) a polypeptide comprising the polypeptide of (a), (b), (c), (d), (f), (g), (h), (i), (j), (k), (l) or (m) and a N-terminal and/or C-terminal extension of between 1 and 10 amino acids; and
(p) a fragment of the polypeptide of (a), (b), (c), (d), (f), (g), (h), (i), (j), (k), (l) or (m) having lysozyme activity and having at least 90% of the length of the mature polypeptide.

An embodiment of the invention is directed to the polypeptides as defined by the invention and having improved lysozyme activity a) compared to the lysozyme activity of hen eggwhite lysozyme (HEWL) or b) compared to the lysozyme activity of SEQ ID NO: 39 as determined by the Method for the Determination of Lysozyme Activity Against *Micrococcus lysodeikticus*.

Typically, the polypeptides of the invention have improved lysozyme activity a) compared to the lysozyme activity of hen eggwhite lysozyme (HEWL) and b) compared to the lysozyme activity of SEQ ID NO: 39 as determined by any one of i) Method for the Determination of Lysozyme Activity Against *Micrococcus lysodeikticus* and ii) Method for the Determination of Lysozyme Activity Against *Lactobacillus johnsonii*.

Further aspects of the invention are directed to a method of hydrolysing peptidoglycan in bacterial cell walls comprising treating bacterial cells with one or more GH25 polypeptides of the invention and to a method of increasing the digestibility of peptidoglycans in animal feed with one or more GH25 polypeptides of the invention.

An important aspect of the invention relates to an animal feed or an animal feed additive comprising the polypeptide of the invention. Similarly, the invention is directed to a zootechnical additive for use in feed for poultry or swine, said additive comprising the polypeptide of the invention.

The invention is furthermore directed to a method of improving the intestinal health in an animal comprising reducing the amount of dead *Lactobacillus johnsonii* cells, or cell wall debris therefrom, in the digestive tract of said animal, comprising feeding the animal with a feed or feed additive. In a separate aspect, the polypeptide in the feed or feed additive for reducing the amount of dead *Lactobacillus johnsonii* cells, or cell wall debris therefrom, in the digestive tract of said animal, comprising feeding the animal with a feed or feed additive comprising a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 39.

The invention may furthermore be defined as being directed to a method of promoting the elimination of dead *Lactobacillus johnsonii* cells, or cell wall debris therefrom, from the digestive tract of an animal comprising feeding said animal a source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 39.

The invention also relates to a granule comprising one or more GH25 polypeptides as described above. The invention further relates to an isolated polypeptide having lysozyme activity as described in the claims.

The invention further relates to compositions comprising the polypeptide of the invention, such as animal feed additives or animal feed; use of the polypeptide of the invention in animal feed, in animal feed additives, in the preparation of a composition for use in animal feed, for improving one or more performance parameters in an animal; and isolated polynucleotides encoding the polypeptides of the invention, recombinant host cells and method of producing the polypeptide of the invention.

Overview of Sequence Listing

SEQ ID NO: 1 is the genomic DNA sequence of a GH25 lysozyme as isolated from *Myceliophthora fergusii*.

SEQ ID NO: 2 is the amino acid sequence as deduced from SEQ ID NO: 1.

SEQ ID NO: 3 is the amino acid sequence of the mature GH25 lysozyme from *Myceliophthora fergusii*.

SEQ ID NO: 4 is the cDNA sequence of a GH25 lysozyme as isolated from *Penicillium* sp. 'qii'.

SEQ ID NO: 5 is the amino acid sequence as deduced from SEQ ID NO: 4.

SEQ ID NO: 6 is the amino acid sequence of the mature GH25 lysozyme from *Penicillium* sp. 'qii'.

SEQ ID NO: 7 is the cDNA sequence of a GH25 lysozyme as isolated from *Paecilomyces* sp. XZ2658.

SEQ ID NO: 8 is the amino acid sequence as deduced from SEQ ID NO: 7.

SEQ ID NO: 9 is the amino acid sequence of the mature GH25 lysozyme from *Paecilomyces* sp. XZ2658.

SEQ ID NO: 10 is the cDNA sequence of a GH25 lysozyme as isolated from *Paecilomyces* sp. XZ2658.

SEQ ID NO: 11 is the amino acid sequence as deduced from SEQ ID NO: 10.

SEQ ID NO: 12 is the amino acid sequence of the mature GH25 lysozyme from *Paecilomyces* sp. XZ2658.

SEQ ID NO: 13 is the cDNA sequence of a GH25 lysozyme as isolated from *Mortierella alpina*.

SEQ ID NO: 14 is the amino acid sequence as deduced from SEQ ID NO: 13.

SEQ ID NO: 15 is the amino acid sequence of the mature GH25 lysozyme from *Mortierella alpina*.

SEQ ID NO: 16 is the cDNA sequence of a GH25 lysozyme as isolated from *Purpureocillium lilacinum*.

SEQ ID NO: 17 is the amino acid sequence as deduced from SEQ ID NO: 16.

SEQ ID NO: 18 is the amino acid sequence of the mature GH25 lysozyme from *Purpureocillium lilacinum*.

SEQ ID NO: 19 is the cDNA sequence of a GH25 lysozyme as isolated from *Onygena equina*.

SEQ ID NO: 20 is the amino acid sequence as deduced from SEQ ID NO: 19.

SEQ ID NO: 21 is the amino acid sequence of the mature GH25 lysozyme from *Onygena equina*.

SEQ ID NO: 22 is the genomic DNA sequence of a GH25 lysozyme as isolated from *Lecanicillium* sp. WMM742.

SEQ ID NO: 23 is the amino acid sequence as deduced from SEQ ID NO: 22.

SEQ ID NO: 24 is the amino acid sequence of the mature GH25 lysozyme from *Lecanicillium* sp. WMM742.

SEQ ID NO: 25 is the cDNA sequence of a GH25 lysozyme as isolated from *Penicillium atrovenetum*.

SEQ ID NO: 26 is the amino acid sequence as deduced from SEQ ID NO: 25.

SEQ ID NO: 27 is the amino acid sequence of the mature GH25 lysozyme from *Penicillium atrovenetum*.

SEQ ID NO: 28 is the cDNA sequence of a GH25 lysozyme as isolated from *Malbranchea flava*.

SEQ ID NO: 29 is the amino acid sequence as deduced from SEQ ID NO: 28.

SEQ ID NO: 30 is the amino acid sequence of the mature GH25 lysozyme from *Malbranchea flava*.

SEQ ID NO: 31 is the cDNA sequence of a GH25 lysozyme as isolated from *Engyodontium album*.

SEQ ID NO: 32 is the amino acid sequence as deduced from SEQ ID NO: 31.

SEQ ID NO: 33 is the amino acid sequence of the mature GH25 lysozyme from *Engyodontium album*.

SEQ ID NO: 34 is the cDNA sequence of a GH25 lysozyme as isolated from *Flammulina velutipes*.

SEQ ID NO: 35 is the amino acid sequence as deduced from SEQ ID NO: 34.

SEQ ID NO: 36 is the codon optimised DNA the GH25 lysozyme as isolated from *Flammulina velutipes*.

SEQ ID NO: 37 is the amino acid sequence as deduced from SEQ ID NO: 36.

SEQ ID NO: 38 is the amino acid sequence of the mature GH25 lysozyme from *Flammulina velutipes*.

SEQ ID NO: 39 is the mature amino acid sequence of a wild type GH25 lysozyme from *Acremonium alcalophilum* as described in WO 2013/076253.

SEQ ID NO: 40 is the conserved motif F[I/L/V][A/S/K][H/N/S]GGGW.

SEQ ID NO: 41 is the conserved motif DGXTLPG.

SEQ ID NO: 42 is the conserved motif WWX[Q/T]CTG.

SEQ ID NO: 43 is the conserved motif F[I/L/V][A/S][H/N/S]GGGWS.

SEQ ID NO: 44 is the forward primer WIN1054-F.
SEQ ID NO: 45 is the reverse primer WIN1054-R.
SEQ ID NO: 46 is the forward primer WIN1057-F.
SEQ ID NO: 47 is the reverse primer WIN1057-R.
SEQ ID NO: 48 is the forward primer WIN1058-F.
SEQ ID NO: 49 is the reverse primer WIN1058-R.
SEQ ID NO: 50 is the forward primer WIN1068-F.
SEQ ID NO: 51 is the reverse primer WIN1068-R.
SEQ ID NO: 52 is the forward primer C8VRQ-F.
SEQ ID NO: 53 is the reverse primer C8VRQ-R.
SEQ ID NO: 54 is the forward primer C8VRJ-F.
SEQ ID NO: 55 is the reverse primer C8VRJ-R.
SEQ ID NO: 56 is the forward primer C8VRZ-F.
SEQ ID NO: 57 is the reverse primer C8VRZ-R.
SEQ ID NO: 58 is the forward primer C8VRT-F.
SEQ ID NO: 59 is the reverse primer C8VRT-R.
SEQ ID NO: 60 is the forward primer C8VS8-F.
SEQ ID NO: 61 is the reverse primer C8VS8-R.

BRIEF DESCRIPTION OF THE FIGURE

FIG. 1 illustrates the results of Example 17: Method for the Determination of Lysozyme Activity Against *Lactobacillus johnsonii*. The FIGURE shows lysozyme activity (OD405) towards peptidoglycan extracted from *L. johnsonii* cell walls. The activity of four different concentrations for each lysozyme (0.63; 1.25, 2.5 and 5.0 µg/mL) is illustrated in the bar plot. Each OD measurement represents the difference after the original (background) reading was subtracted and represents the average of two OD measurements.

DETAILED DESCRIPTION OF THE INVENTION

The term "animal" refers to any animal except humans. Examples of animals are monogastric animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

The term "animal feed" refers to any compound, preparation, or mixture suitable for, or intended for intake by an animal. Animal feed for a monogastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

The term "antimicrobial activity" is defined herein as an activity that kills or inhibits the growth of microorganisms, such as, algae, archea, bacteria, fungi and/or protozoans. The antimicrobial activity can, for example, be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the lysozyme binding to the surface of the microorganism and inhibiting its growth. The antimicrobial effect can also include the use of the lysozymes of the present invention for activation of bacterial autolysins, as an immunostimulator, by inhibiting or reducing bacterial toxins and by an opsonin effect.

The term "body weight gain" means an increase in live weight of an animal during a given period of time e.g. the increase in weight from day 1 to day 21.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The "European Production Efficacy Factor" is a way of comparing the performance of animals. This single-figure facilitates comparison of performance within and among farms and can be used to assess environmental, climatic and managemental variables. The EPEF is calculated as [(livability (%)×Liveweight (kg))/(Age at depletion (days)× FCR)]×100, wherein livability is the percentage of animals alive at slaughter, Liveweight is the average weight of the animals at slaughter, age of depletion is the age of the animals at slaughter and FCR is the feed conversion ratio at slaughter.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression.

FCR is a measure of an animal's efficiency in converting feed mass into increases of the desired output. Animals raised for meat—such as swine, poultry and fish—the output is the mass gained by the animal. Specifically, FCR is calculated as feed intake divided by weight gain, all over a specified period. Improvement in FCR means reduction of the FCR value. A FCR improvement of 2% means that the FCR was reduced by 2%.

The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, *brassica* (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

The term "fragment" means a polypeptide having one or more (e.g., several) amino acids absent from the amino and/or carboxyl terminus of a mature polypeptide or domain; wherein the fragment has lysozyme activity.

In one aspect, the fragment comprises at least 90% of the length of the mature polypeptide, such as at least 186 amino acids of SEQ ID NO: 2, at least 186 amino acids of SEQ ID NO: 3, at least 194 amino acids of SEQ ID NO: 5, at least 194 amino acids of SEQ ID NO: 6, at least 183 amino acids of SEQ ID NO: 8, at least 183 amino acids of SEQ ID NO: 9, at least 182 amino acids of SEQ ID NO: 11, at least 182 amino acids of SEQ ID NO: 12, at least 183 amino acids of SEQ ID NO: 14, at least 183 amino acids of SEQ ID NO: 15, at least 187 amino acids of SEQ ID NO: 17, at least 187 amino acids of SEQ ID NO: 18, at least 186 amino acids of SEQ ID NO: 20, at least 186 amino acids of SEQ ID NO: 21, at least 186 amino acids of SEQ ID NO: 23, at least 186 amino acids of SEQ ID NO: 24, at least 194 amino acids of SEQ ID NO: 26, at least 194 amino acids of SEQ ID NO: 27, at least 195 amino acids of SEQ ID NO: 29, at least 195 amino acids of SEQ ID NO: 30, at least 186 amino acids of SEQ ID NO: 32, at least 186 amino acids of SEQ ID NO: 33, at least 186 amino acids of SEQ ID NO: 35, at least 186 amino acids of SEQ ID NO: 37 or at least 186 amino acids of SEQ ID NO: 38.

In another aspect, the fragment comprises at least 92% of the length of the mature polypeptide, such as at least 190 amino acids of SEQ ID NO: 2, at least 190 amino acids of SEQ ID NO: 3, at least 198 amino acids of SEQ ID NO: 5, at least 198 amino acids of SEQ ID NO: 6, at least 187 amino acids of SEQ ID NO: 8, at least 187 amino acids of SEQ ID NO: 9, at least 186 amino acids of SEQ ID NO: 11, at least 186 amino acids of SEQ ID NO: 12, at least 187 amino acids of SEQ ID NO: 14, at least 187 amino acids of SEQ ID NO: 15, at least 191 amino acids of SEQ ID NO: 17, at least 191 amino acids of SEQ ID NO: 18, at least 190 amino acids of SEQ ID NO: 20, at least 190 amino acids of SEQ ID NO: 21, at least 190 amino acids of SEQ ID NO: 23, at least 190 amino acids of SEQ ID NO: 24, at least 198 amino acids of SEQ ID NO: 26, at least 198 amino acids of SEQ ID NO: 27, at least 199 amino acids of SEQ ID NO: 29, at least 199 amino acids of SEQ ID NO: 30, at least 190 amino acids of SEQ ID NO: 32, at least 190 amino acids of SEQ ID NO: 33, at least 190 amino acids of SEQ ID NO: 35, at least 190 amino acids of SEQ ID NO: 37 or at least 190 amino acids of SEQ ID NO: 38.

In another aspect, the fragment comprises at least 94% of the length of the mature polypeptide, such as at least 194 amino acids of SEQ ID NO: 2, at least 194 amino acids of SEQ ID NO: 3, at least 203 amino acids of SEQ ID NO: 5, at least 203 amino acids of SEQ ID NO: 6, at least 191 amino acids of SEQ ID NO: 8, at least 191 amino acids of SEQ ID NO: 9, at least 190 amino acids of SEQ ID NO: 11, at least 190 amino acids of SEQ ID NO: 12, at least 191 amino acids of SEQ ID NO: 14, at least 191 amino acids of SEQ ID NO: 15, at least 195 amino acids of SEQ ID NO: 17, at least 195 amino acids of SEQ ID NO: 18, at least 194 amino acids of SEQ ID NO: 20, at least 194 amino acids of SEQ ID NO: 21, at least 194 amino acids of SEQ ID NO: 23, at least 194 amino acids of SEQ ID NO: 24, at least 203 amino acids of SEQ ID NO: 26, at least 203 amino acids of SEQ ID NO: 27, at least 203 amino acids of SEQ ID NO: 29, at least 203 amino acids of SEQ ID NO: 30, at least 194 amino acids of SEQ ID NO: 32, at least 194 amino acids of SEQ ID NO: 33, at least 194 amino acids of SEQ ID NO: 35, at least 194 amino acids of SEQ ID NO: 37 or at least 194 amino acids of SEQ ID NO: 38.

In another aspect, the fragment comprises at least 96% of the length of the mature polypeptide, such as at least 198 amino acids of SEQ ID NO: 2, at least 198 amino acids of SEQ ID NO: 3, at least 207 amino acids of SEQ ID NO: 5, at least 207 amino acids of SEQ ID NO: 6, at least 195 amino acids of SEQ ID NO: 8, at least 195 amino acids of SEQ ID NO: 9, at least 194 amino acids of SEQ ID NO: 11, at least 194 amino acids of SEQ ID NO: 12, at least 195 amino acids of SEQ ID NO: 14, at least 195 amino acids of SEQ ID NO: 15, at least 199 amino acids of SEQ ID NO: 17, at least 199 amino acids of SEQ ID NO: 18, at least 198 amino acids of SEQ ID NO: 20, at least 198 amino acids of SEQ ID NO: 21, at least 198 amino acids of SEQ ID NO: 23, at least 198 amino acids of SEQ ID NO: 24, at least 207 amino acids of SEQ ID NO: 26, at least 207 amino acids of SEQ ID NO: 27, at least 208 amino acids of SEQ ID NO: 29, at least 208 amino acids of SEQ ID NO: 30, at least 198 amino acids of SEQ ID NO: 32, at least 198 amino acids of SEQ ID NO: 33, at least 198 amino acids of SEQ ID NO: 35, at least 198 amino acids of SEQ ID NO: 37 or at least 198 amino acids of SEQ ID NO: 38.

In another aspect, the fragment comprises at least 98% of the length of the mature polypeptide, such as at least 202 amino acids of SEQ ID NO: 2, at least 202 amino acids of SEQ ID NO: 3, at least 211 amino acids of SEQ ID NO: 5, at least 211 amino acids of SEQ ID NO: 6, at least 199 amino acids of SEQ ID NO: 8, at least 199 amino acids of SEQ ID NO: 9, at least 198 amino acids of SEQ ID NO: 11, at least 198 amino acids of SEQ ID NO: 12, at least 199 amino acids of SEQ ID NO: 14, at least 199 amino acids of SEQ ID NO: 15, at least 203 amino acids of SEQ ID NO: 17, at least 203 amino acids of SEQ ID NO: 18, at least 202 amino acids of SEQ ID NO: 20, at least 202 amino acids of SEQ ID NO: 21, at least 202 amino acids of SEQ ID NO: 23, at least 202 amino acids of SEQ ID NO: 24, at least 211 amino acids of SEQ ID NO: 26, at least 211 amino acids of SEQ ID NO: 27, at least 212 amino acids of SEQ ID NO: 29, at least 212 amino acids of SEQ ID NO: 30, at least 202 amino acids of SEQ ID NO: 32, at least 202 amino acids of SEQ ID NO: 33, at least 202 amino acids of SEQ ID NO: 35, at least 202 amino acids of SEQ ID NO: 37 or at least 202 amino acids of SEQ ID NO: 38.

In another aspect, the fragment comprises at least 99% of the length of the mature polypeptide, such as at least 204 amino acids of SEQ ID NO: 2, at least 204 amino acids of SEQ ID NO: 3, at least 213 amino acids of SEQ ID NO: 5, at least 213 amino acids of SEQ ID NO: 6, at least 201 amino acids of SEQ ID NO: 8, at least 201 amino acids of SEQ ID NO: 9, at least 200 amino acids of SEQ ID NO: 11, at least 200 amino acids of SEQ ID NO: 12, at least 201 amino acids of SEQ ID NO: 14, at least 201 amino acids of SEQ ID NO: 15, at least 205 amino acids of SEQ ID NO: 17, at least 205 amino acids of SEQ ID NO: 18, at least 204 amino acids of SEQ ID NO: 20, at least 204 amino acids of SEQ ID NO: 21, at least 204 amino acids of SEQ ID NO: 23, at least 204 amino acids of SEQ ID NO: 24, at least 213 amino acids of SEQ ID NO: 26, at least 213 amino acids of SEQ ID NO: 27, at least 214 amino acids of SEQ ID NO: 29, at least 214 amino acids of SEQ ID NO: 30, at least 204 amino acids of SEQ ID NO: 32, at least 204 amino acids of SEQ ID NO: 33, at least 204 amino acids of SEQ ID NO: 35, at least 204 amino acids of SEQ ID NO: 37 or at least 204 amino acids of SEQ ID NO: 38.

The term "fusion polypeptide" is a polypeptide in which one polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "hybrid polypeptide" means a polypeptide comprising domains from two or more polypeptides, e.g., a binding domain from one polypeptide and a catalytic domain from another polypeptide. The domains may be fused at the N-terminus or the C-terminus.

The term "isolated" means a substance in a form that does not occur in nature or in an environment in which the substance does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

The term "lysozyme activity" means the hydrolysis of the 1,4-beta-linkages between N-acetylmuramic acid and N-acetyl-D-glucosamine residues in a peptidoglycan or between N-acetyl-D-glucosamine residues in chitodextrins, resulting in bacteriolysis. Lysozyme belongs to the enzyme class EC 3.2.1.17. Lysozyme activity is typically measured by turbidimetric determination, such as the changes in turbidity of a suspension of *Micrococcus luteus* ATCC 4698 induced by the lytic action of the lysozyme. In appropriate experimental conditions these changes are proportional to the amount of lysozyme in the medium (c.f. INS 1105 of the Combined Compendium of Food Additive Specifications of the Food and Agriculture Organisation of the UN (fao.orq)). For the purpose of the present invention, lysozyme activity is determined according to the turbidity assay described in example 1 ("Method for the Determination of Lysozyme Activity Against *Micrococcus lysodeikticus*"). The polypeptide has lysozyme activity if it shows activity against *Micrococcus luteus* ATCC 4698, and specifically the lysozymes of the invention exhibit improved activity compared to the prior art lysozyme of SEQ ID NO: 39 wherein lysozyme activity is determined as described in example 1.

In one aspect, the polypeptides of the present invention have significantly improved lysozyme activity compared to the activity of SEQ ID NO: 39. In an embodiment, the polypeptides of the present invention have significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test. In an embodiment, the polypeptides of the present invention have significantly improved lysozyme activity compared to the activity of SEQ ID NO: 39, wherein the activity is determined by measuring the decrease in optical density of a solution of resuspended *Micrococcus lysodeikticus* cells, preferably *Micrococcus luteus* ATCC 4698 cells.

Dunnetts test is described in Dunnett C. W. (1955.) "A multiple comparison procedure for comparing several treatments with a control", *Journal of the American Statistical Association*, 50:1096-1121. In brief, the Dunnett's test compares a set of means against the mean of a control group. The LSDs that it produces are between the Student's t and Tukey-Kramer LSDs, because they are sized to refrain from an intermediate number of comparisons. Commercial software, such as JMP (SAS Institute Inc, Cary, N.C. 27513), can be used to calculate Dunnetts test.

The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 207 of SEQ ID NO: 2 and amino acids −18 to −1 of SEQ ID NO: 2 are a signal peptide. In another aspect, the mature polypeptide is amino acids 1 to 207 of SEQ ID NO: 3.

In one aspect, the mature polypeptide is amino acids 1 to 216 of SEQ ID NO: 5 and amino acids −17 to −1 of SEQ ID NO: 5 are a signal peptide. In another aspect, the mature polypeptide is amino acids 1 to 216 of SEQ ID NO: 6.

In one aspect, the mature polypeptide is amino acids 1 to 204 of SEQ ID NO: 8 and amino acids −19 to −1 of SEQ ID NO: 8 are a signal peptide. In another aspect, the mature polypeptide is amino acids 1 to 204 of SEQ ID NO: 9.

In one aspect, the mature polypeptide is amino acids 1 to 203 of SEQ ID NO: 11 and amino acids −19 to −1 of SEQ ID NO: 11 are a signal peptide. In another aspect, the mature polypeptide is amino acids 1 to 203 of SEQ ID NO: 12.

In one aspect, the mature polypeptide is amino acids 1 to 204 of SEQ ID NO: 14 and amino acids −16 to −1 of SEQ ID NO: 14 are a signal peptide. In another aspect, the mature polypeptide is amino acids 1 to 204 of SEQ ID NO: 15.

In one aspect, the mature polypeptide is amino acids 1 to 208 of SEQ ID NO: 17 and amino acids −19 to −1 of SEQ ID NO: 17 are a signal peptide. In another aspect, the mature polypeptide is amino acids 1 to 208 of SEQ ID NO: 18.

In one aspect, the mature polypeptide is amino acids 1 to 207 of SEQ ID NO: 20 and amino acids −18 to −1 of SEQ ID NO: 20 are a signal peptide. In another aspect, the mature polypeptide is amino acids 1 to 207 of SEQ ID NO: 21.

In one aspect, the mature polypeptide is amino acids 1 to 207 of SEQ ID NO: 23 and amino acids −19 to −1 of SEQ ID NO: 23 are a signal peptide. In another aspect, the mature polypeptide is amino acids 1 to 207 of SEQ ID NO: 24.

In one aspect, the mature polypeptide is amino acids 1 to 216 of SEQ ID NO: 26 and amino acids −15 to −1 of SEQ ID NO: 26 are a signal peptide. In another aspect, the mature polypeptide is amino acids 1 to 216 of SEQ ID NO: 27.

In one aspect, the mature polypeptide is amino acids 1 to 217 of SEQ ID NO: 29 and amino acids −18 to −1 of SEQ ID NO: 29 are a signal peptide. In another aspect, the mature polypeptide is amino acids 1 to 217 of SEQ ID NO: 30.

In one aspect, the mature polypeptide is amino acids 1 to 207 of SEQ ID NO: 32 and amino acids −20 to −1 of SEQ ID NO: 32 are a signal peptide. In another aspect, the mature polypeptide is amino acids 1 to 207 of SEQ ID NO: 33.

In one aspect, the mature polypeptide is amino acids 1 to 207 of SEQ ID NO: 35 and amino acids −17 to −1 of SEQ ID NO: 35 are a signal peptide. In another aspect, the mature polypeptide is amino acids 1 to 207 of SEQ ID NO: 37.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having lysozyme activity.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "obtained or obtainable from" means that the polypeptide may be found in an organism from a specific taxonomic rank. In one embodiment, the polypeptide is obtained or obtainable from the kingdom Fungi, wherein the term kingdom is the taxonomic rank. In a preferred embodiment, the polypeptide is obtained or obtainable from the phylum Ascomycota, wherein the term phylum is the taxonomic rank. In another preferred embodiment, the polypeptide is obtained or obtainable from the subphylum Pezizomycotina, wherein the term subphylum is the taxonomic rank.

If the taxonomic rank of a polypeptide is not known, it can easily be determined by a person skilled in the art by performing a BLASTP search of the polypeptide (using e.g. the National Center for Biotechnology Information (NCIB) website http://www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

The term "operably linked" means a configuration in which a control sequence is placed at an appropriate position relative to the coding sequence of a polynucleotide such that the control sequence directs expression of the coding sequence.

The term "roughage" means dry plant material with high levels of fiber, such as fiber, bran, husks from seeds and grains and crop residues (such as stover, copra, straw, chaff, sugar beet waste).

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the –nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the –nobrief option) is used as the percent identity and is calculated as follows:

(Identical Deoxyribonucleotides×100)/(Length of
Alignment−Total Number of Gaps in Alignment)

The term "subsequence" means a polynucleotide having one or more (e.g., several) nucleotides absent from the 5' and/or 3' end of a mature polypeptide coding sequence; wherein the subsequence encodes a fragment having lysozyme activity.

The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

For purposes of the present invention, the nomenclature [E/Q] means that the amino acid at this position may be a glutamic acid (Glu, E) or a glutamine (Gln, Q). Likewise the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

Methods of Hydrolysing Peptidoglycan in Bacterial Cell Walls

In one aspect, the invention relates to a method of hydrolysing peptidoglycan in bacterial cell walls comprising treating bacterial cells with one or more GH25 polypeptides having lysozyme activity, wherein the polypeptide is selected from the group consisting of:

(a) a polypeptide having at least 90%, such as at least 95% sequence identity to the polypeptide of SEQ ID NO: 3;
(b) a polypeptide having at least 80%, such as at least 85%, at least 90% or at least 95% sequence identity to the polypeptide of SEQ ID NO: 6;
(c) a polypeptide having at least 80%, such as at least 85%, at least 90% or at least 95% sequence identity to the polypeptide of SEQ ID NO: 9;
(d) a polypeptide having at least 80%, such as at least 85%, at least 90% or at least 95% sequence identity to the polypeptide of SEQ ID NO: 12;
(e) a polypeptide having at least 80%, such as at least 85%, at least 90% or at least 95% sequence identity to the polypeptide of SEQ ID NO: 15;
(f) a polypeptide having at least 80%, such as at least 85%, at least 90% or at least 95% sequence identity to the polypeptide of SEQ ID NO: 18;
(g) a polypeptide having at least 80%, such as at least 85%, at least 90% or at least 95% sequence identity to the polypeptide of SEQ ID NO: 21;
(h) a polypeptide having at least 80%, such as at least 85%, at least 90% or at least 95% sequence identity to the polypeptide of SEQ ID NO: 24;
(i) a polypeptide having at least 80%, such as at least 85%, at least 90% or at least 95% sequence identity to the polypeptide of SEQ ID NO: 27;
(j) a polypeptide having at least 80%, such as at least 85%, at least 90% or at least 95% sequence identity to the polypeptide of SEQ ID NO: 30;
(k) a polypeptide having at least 80%, such as at least 85%, at least 90% or at least 95% sequence identity to the polypeptide of SEQ ID NO: 33;
(l) a polypeptide having at least 83%, such as at least 85%, at least 90% or at least 95% sequence identity to the polypeptide of SEQ ID NO: 38;
(m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(n) a polypeptide comprising the polypeptide of (a), (b), (c), (d), (e), (f), (g), (h), (i), (j), (k), (l) or (m) and a N-terminal and/or C-terminal His-tag and/or HQ-tag;
(o) a polypeptide comprising the polypeptide of (a), (b), (c), (d), (e), (f), (g), (h), (i), (j), (k), (l) or (m) and a N-terminal and/or C-terminal extension of between 1 and 10 amino acids; and
(p) a fragment of the polypeptide of (a), (b), (c), (d), (e), (f), (g), (h), (i), (j), (k), (l) or (m) having lysozyme activity and having at least 90% of the length of the mature polypeptide.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the GH25 polypeptide comprises the motif F[I/L/V][A/S][H/N/S]GGGWS (SEQ ID NO: 43).

In an embodiment, the polypeptide comprises or consists of amino acids 1 to 207 of SEQ ID NO: 3, amino acids 1 to 216 of SEQ ID NO: 6, amino acids 1 to 204 of SEQ ID NO: 9, amino acids 1 to 203 of SEQ ID NO: 12, amino acids 1 to 204 of SEQ ID NO: 15, amino acids 1 to 208 of SEQ ID NO: 18, amino acids 1 to 207 of SEQ ID NO: 21, amino acids 1 to 207 of SEQ ID NO: 24, amino acids 1 to 216 of SEQ ID NO: 27, amino acids 1 to 217 of SEQ ID NO: 30, amino acids 1 to 207 of SEQ ID NO: 33 or amino acids 1 to 207 of SEQ ID NO: 38.

In a preferred embodiment, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test. In an embodiment, the polypeptides of the present invention have significantly improved lysozyme activity compared to the activity of SEQ ID NO: 39, wherein the activity is determined by measuring the decrease in optical density of a solution of resuspended *Micrococcus lysodeikticus* cells, preferably *Micrococcus luteus* ATCC 4698 cells, preferably wherein lysozyme activity is determined as described in example 1.

In an embodiment, the polypeptides of the present invention have significantly improved lysozyme activity compared to the activity of SEQ ID NO: 39, wherein the activity is determined by measuring the decrease in optical density of a solution of resuspended *Micrococcus lysodeikticus* cells, preferably *Micrococcus luteus* ATCC 4698 cells wherein lysozyme activity is determined as follows: the lysozyme sample was diluted to a concentration of 50 mg enzyme protein/L in deionized water; 180 µL buffer (0.1M citric acid-0.2 M disodium hydrogen phosphate buffer pH 4) and 20 µL of the diluted lysozyme sample was added and kept cold (5° C.); 20 µL of the substrate (10 mg cells/mL *Micrococcus lysodeikticus* ATCC 4698 in deionized water) was added to each well; absorbance at 450 nm was initiated for 1 hour at 37° C.; lysozyme activity was determined as A absorbance at 450 nm (start value–end value) of each well after 1 hour.

Granules Comprising Polypeptides Having Lysozyme Activity

In a second aspect, the invention relates to a granule comprising one or more GH25 polypeptides having lysozyme activity, wherein the polypeptide is selected from the group consisting of:
(a) a polypeptide having at least 90%, such as at least 95% sequence identity to the polypeptide of SEQ ID NO: 3;
(b) a polypeptide having at least 80%, such as at least 85%, at least 90% or at least 95% sequence identity to the polypeptide of SEQ ID NO: 6;
(c) a polypeptide having at least 80%, such as at least 85%, at least 90% or at least 95% sequence identity to the polypeptide of SEQ ID NO: 9;
(d) a polypeptide having at least 80%, such as at least 85%, at least 90% or at least 95% sequence identity to the polypeptide of SEQ ID NO: 12;
(e) a polypeptide having at least 80%, such as at least 85%, at least 90% or at least 95% sequence identity to the polypeptide of SEQ ID NO: 15;
(f) a polypeptide having at least 80%, such as at least 85%, at least 90% or at least 95% sequence identity to the polypeptide of SEQ ID NO: 18;
(g) a polypeptide having at least 80%, such as at least 85%, at least 90% or at least 95% sequence identity to the polypeptide of SEQ ID NO: 21;

(h) a polypeptide having at least 80%, such as at least 85%, at least 90% or at least 95% sequence identity to the polypeptide of SEQ ID NO: 24;
(i) a polypeptide having at least 80%, such as at least 85%, at least 90% or at least 95% sequence identity to the polypeptide of SEQ ID NO: 27;
(j) a polypeptide having at least 80%, such as at least 85%, at least 90% or at least 95% sequence identity to the polypeptide of SEQ ID NO: 30;
(k) a polypeptide having at least 80%, such as at least 85%, at least 90% or at least 95% sequence identity to the polypeptide of SEQ ID NO: 33;
(l) a polypeptide having at least 83%, such as at least 85%, at least 90% or at least 95% sequence identity to the polypeptide of SEQ ID NO: 38;
(m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(n) a polypeptide comprising the polypeptide of (a), (b), (c), (d), (e), (f), (g), (h), (i), (j), (k), (l) or (m) and a N-terminal and/or C-terminal His-tag and/or HQ-tag;
(o) a polypeptide comprising the polypeptide of (a), (b), (c), (d), (e), (f), (g), (h), (i), (j), (k), (l) or (m) and a N-terminal and/or C-terminal extension of between 1 and 10 amino acids; and
(p) a fragment of the polypeptide of (a), (b), (c), (d), (e), (f), (g), (h), (i), (j), (k), (l) or (m) having lysozyme activity and having at least 90% of the length of the mature polypeptide.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the GH25 polypeptide comprises the motif F[I/L/V][A/S][H/N/S]GGGWS (SEQ ID NO: 43).

In an embodiment, the polypeptide comprises or consists of amino acids 1 to 207 of SEQ ID NO: 3, amino acids 1 to 216 of SEQ ID NO: 6, amino acids 1 to 204 of SEQ ID NO: 9, amino acids 1 to 203 of SEQ ID NO: 12, amino acids 1 to 204 of SEQ ID NO: 15, amino acids 1 to 208 of SEQ ID NO: 18, amino acids 1 to 207 of SEQ ID NO: 21, amino acids 1 to 207 of SEQ ID NO: 24, amino acids 1 to 216 of SEQ ID NO: 27, amino acids 1 to 217 of SEQ ID NO: 30, amino acids 1 to 207 of SEQ ID NO: 33 or amino acids 1 to 207 of SEQ ID NO: 38.

In a preferred embodiment, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test. In an embodiment, the polypeptides of the present invention have significantly improved lysozyme activity compared to the activity of SEQ ID NO: 39, wherein the activity is determined by measuring the decrease in optical density of a solution of resuspended *Micrococcus lysodeikti-cus* cells, preferably *Micrococcus luteus* ATCC 4698 cells, preferably wherein lysozyme activity is determined as described in example 1.

In an embodiment, the polypeptides of the present invention have significantly improved lysozyme activity compared to the activity of SEQ ID NO: 39, wherein the activity is determined by measuring the decrease in optical density of a solution of resuspended *Micrococcus lysodeikticus* cells, preferably *Micrococcus luteus* ATCC 4698 cells wherein lysozyme activity is determined as follows: the lysozyme sample was diluted to a concentration of 50 mg enzyme protein/L in deionized water; 180 µL buffer (0.1M citric acid-0.2 M disodium hydrogen phosphate buffer pH 4) and 20 µL of the diluted lysozyme sample was added and kept cold (5° C.); 20 µL of the substrate (10 mg cells/mL *Micrococcus lysodeikticus* ATCC 4698 in deionized water) was added to each well; absorbance at 450 nm was initiated for 1 hour at 37° C.; lysozyme activity was determined as A absorbance at 450 nm (start value–end value) of each well after 1 hour.

In an embodiment of the second aspect, the granule comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose, preferably selected from the list consisting of 1, 2-propylene glycol, 1, 3-propylene glycol, sodium sulfate, dextrin, cellulose, sodium thiosulfate, kaolin and calcium carbonate.

In a further embodiment to any part of the second aspect, the granule comprises a core particle and one or more coatings. In a preferred embodiment, the coating comprises salt and/or wax and/or flour.

In an embodiment, the granule comprises one or more additional enzymes. The one or more additional enzymes is preferably selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

In an embodiment, the granule comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

Polypeptides Having Lysozyme Activity

In a further aspect, the polypeptide comprises or consists of amino acids 1 to 207 of SEQ ID NO: 3, amino acids 1 to 216 of SEQ ID NO: 6, amino acids 1 to 204 of SEQ ID NO: 9, amino acids 1 to 203 of SEQ ID NO: 12, amino acids 1 to 208 of SEQ ID NO: 18, amino acids 1 to 207 of SEQ ID NO: 21, amino acids 1 to 207 of SEQ ID NO: 24, amino acids 1 to 207 of SEQ ID NO: 33 or amino acids 1 to 207 of SEQ ID NO: 38.

In a third aspect, the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 2. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from the mature polypeptide of SEQ ID NO: 2.

In a continuation of the third aspect, the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to SEQ ID NO: 3. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from SEQ ID NO: 3.

In one embodiment, the invention relates to polypeptides having lysozyme activity and having a sequence identity to SEQ ID NO: 3 of at least 90% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 3 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 2. In another embodiment, the polypeptide comprises or consists of the mature polypeptide of SEQ ID NO: 2. In another embodiment, the polypeptide comprises or consists of amino acids 1 to 207 of SEQ ID NO: 2. In one embodiment, the polypeptide preferably comprises or consists of the amino acid sequence of SEQ ID NO: 3; comprises the amino acid sequence of SEQ ID NO: 3 and a N-terminal and/or C-terminal His-tag and/or HQ-tag; comprises the amino acid sequence of SEQ ID NO: 3 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 3. In another embodiment, the polypeptide comprises or consists of amino acids 1 to 207 of SEQ ID NO: 3. In an embodiment, the polypeptide has been isolated.

In a continuation of the third aspect, the invention relates to a polypeptide having lysozyme activity encoded by a polynucleotide having a sequence identity to the mature polypeptide coding sequence of SEQ ID NO: 1 of at least 90%, e.g., at least 91%, at least 92%, at least 93%, at least 94%, at least 95%, at least 96%, at least 97%, at least 98%, at least 99%, or 100%. In a further embodiment, the polypeptide has been isolated.

In an embodiment of the third aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the third aspect, the invention relates to variants of SEQ ID NO: 3 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 3 is not more than 20, e.g., 1, 2, 3, 4, 5, 6, 7, 8, 9, 10, 11, 12, 13, 14, 15, 16, 17, 18, 19 or 20. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In another embodiment, the number of substitutions and/or deletions and/or insertions in SEQ ID NO: 3 is not more than 10, e.g., 1, 2, 3, 4, 5, 6, 7, 8, 9 or 10. In a further embodiment, the number of substitutions, preferably conservative substitutions, in SEQ ID NO: 3 is not more than 10, e.g., 1, 2, 3, 4, 5, 6, 7, 8, 9 or 10.

In an embodiment of the third aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

WO 2013/076253 disclosed that amino acid residues D95 and E97 of SEQ ID NO: 8 of WO 2013/076253 are catalytic residues. SEQ ID NO: 8 of WO 2013/076253 corresponds to SEQ ID NO: 39 of the present application. A section of the alignment of the lysozymes of the present invention with SEQ ID NO: 8 of WO 2013/076253 is given below. This alignment can be used to determine the position of the catalytic amino acids for the claimed lysozymes. In one embodiment, no alteration is made to an amino acid corresponding to E97 and D95 when using SEQ ID NO: 39 for numbering.

host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the polypeptide may be a hybrid polypeptide or a fusion polypeptide.

In a fourth aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 5. In one embodiment, the polypeptides differ by up to 32 amino acids, e.g., 1, 2, 3, 4, 5, 6, 7, 8, 9, 10, 11, 12,

| Amino acid number of SEQ ID NO: 8 of WO 2013/076253 | 86 | 87 | 88 | 89 | 90 | 91 | 92 | 93 | 94 | 95 | 96 | 97 | 98 | 99 | 100 | 101 | 102 | 103 | 104 | 105 | 106 |
|---|---|---|---|---|---|---|---|---|---|---|---|---|---|---|---|---|---|---|---|---|---|
| SEQ ID NO: 3 | D | G | I | T | L | P | G | M | L | D | L | E | A | Y | N | A | G | — | E | C | W |
| SEQ ID NO: 6 | D | G | I | T | L | P | G | M | L | D | I | E | Y | N | P | S | G | S | T | C | Y |
| SEQ ID NO: 9 | D | G | I | T | L | P | G | M | I | D | L | E | Y | N | P | S | G | A | T | C | Y |
| SEQ ID NO: 12 | D | G | R | T | L | P | G | A | L | D | L | E | A | G | — | — | — | — | — | C | S |
| SEQ ID NO: 15 | D | G | I | T | L | P | G | A | L | D | L | E | A | G | — | — | — | — | — | C | S |
| SEQ ID NO: 18 | D | G | I | T | L | P | G | M | L | D | M | E | Y | Q | S | S | S | S | A | C | G |
| SEQ ID NO: 21 | D | G | K | T | L | P | G | A | V | D | L | E | Y | G | P | N | G | S | T | C | W |
| SEQ ID NO: 24 | D | G | I | T | L | P | G | M | L | D | L | E | Y | G | P | N | G | N | T | C | Y |
| SEQ ID NO: 27 | D | G | K | T | L | P | G | M | L | D | I | E | Y | N | P | S | G | A | T | C | Y |
| SEQ ID NO: 30 | D | G | I | T | L | P | G | M | L | D | I | E | S | N | P | Y | G | A | Q | C | Y |
| SEQ ID NO: 33 | D | G | I | T | L | P | G | M | L | D | M | E | Y | N | P | N | G | S | A | C | Y |
| SEQ ID NO: 38 | D | G | I | T | L | P | G | A | L | D | I | E | Y | N | P | S | G | A | T | C | Y |
| SEQ ID NO: 8 of WO2013/076253 | D | G | I | T | L | P | G | A | L | D | I | E | Y | N | P | N | G | A | T | C | Y |

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by 13, 14, 15, 16, 17, 18, 19, 20, 21, 22, 23, 24, 25, 26, 27, 28, 29, 30, 31 or 32 amino acids from the mature polypeptide of SEQ ID NO: 5.

In a continuation of the fourth aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 6. In one embodiment, the polypeptides differ by up to 32 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 amino acids from the mature polypeptide of SEQ ID NO: 6.

In one embodiment, the invention relates to polypeptides having lysozyme activity and having a sequence identity to SEQ ID NO: 6 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 6 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 6 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 5. In another embodiment, the polypeptide comprises or consists of the mature polypeptide of SEQ ID NO: 5. In another embodiment, the polypeptide comprises or consists of amino acids 1 to 216 of SEQ ID NO: 5. In one embodiment, the polypeptide preferably comprises or consists of the amino acid sequence of SEQ ID NO: 6; comprises the amino acid sequence of SEQ ID NO: 6 and a N-terminal and/or C-terminal His-tag and/or HQ-tag; comprises the amino acid sequence of SEQ ID NO: 6 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 6. In another embodiment, the polypeptide comprises or consists of amino acids 1 to 216 of SEQ ID NO: 6. In an embodiment, the polypeptide has been isolated.

In a continuation of the fourth aspect, the invention relates to a polypeptide having lysozyme activity encoded by a polynucleotide having a sequence identity to the mature polypeptide coding sequence of SEQ ID NO: 4 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fourth aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the fourth aspect, the invention relates to variants of SEQ ID NO: 6 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 6 is not more than 32, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32. In an embodiment, the number of positions comprising one or more amino acid substitutions, and/or one or more amino acid deletions, and/or one or more amino acid insertions or any combination thereof in SEQ ID NO: 6 is not more than 10, e.g., 1, 2, 3, 4, 5, 6, 7, 8, 9 or 10. In another embodiment, the number of substitutions and/or deletions and/or insertions in SEQ ID NO: 6 is not more than 10, e.g., 1, 2, 3, 4, 5, 6, 7, 8, 9 or 10. In a further embodiment, the number of substitutions, preferably conservative substitutions, in SEQ ID NO: 6 is not more than 10, e.g., 1, 2, 3, 4, 5, 6, 7, 8, 9 or 10. Examples of amino acid changes and conservative substitutions are described in the third aspect of the invention.

In an embodiment of the fourth aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the polypeptide may be a hybrid polypeptide or a fusion polypeptide.

In a fifth aspect the invention relates to polypeptides having lysozyme activity having at least 91%, e.g., at least 92%, at least 93%, at least 94%, at least 95%, at least 96%, at least 97%, at least 98%, at least 99%, or 100% sequence identity to the mature polypeptide of SEQ ID NO: 8. In one embodiment, the polypeptides differ by up to 18 amino acids, e.g., 1, 2, 3, 4, 5, 6, 7, 8, 9, 10, 11, 12, 13, 14, 15, 16, 17 or 18 amino acids from the mature polypeptide of SEQ ID NO: 8.

In a continuation of the fifth aspect, the invention relates to polypeptides having lysozyme activity having at least 91%, e.g., at least 92%, at least 93%, at least 94%, at least 95%, at least 96%, at least 97%, at least 98%, at least 99%, or 100% sequence identity to SEQ ID NO: 9. In one embodiment, the polypeptides differ by up to 18 amino acids, e.g., 1, 2, 3, 4, 5, 6, 7, 8, 9, 10, 11, 12, 13, 14, 15, 16, 17 or 18 amino acids from the mature polypeptide of SEQ ID NO: 9.

In one embodiment, the invention relates to polypeptides having lysozyme activity and having a sequence identity to SEQ ID NO: 9 of at least 91% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 9 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 8. In another embodiment, the polypeptide comprises or consists of the mature polypeptide of SEQ ID NO: 8. In another embodiment, the polypeptide comprises or consists of amino acids 1 to 204 of SEQ ID NO: 8. In one embodiment, the polypeptide preferably comprises or consists of the amino acid sequence of SEQ ID NO: 9; comprises the amino acid sequence of SEQ ID NO: 9 and a N-terminal and/or C-terminal His-tag and/or HQ-tag; comprises the amino acid sequence of SEQ ID NO: 9 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 9. In another embodiment, the polypeptide comprises or consists of amino acids 1 to 204 of SEQ ID NO: 9. In an embodiment, the polypeptide has been isolated.

In a continuation of the fifth aspect, the invention relates to a polypeptide having lysozyme activity encoded by a polynucleotide having a sequence identity to the mature polypeptide coding sequence of SEQ ID NO: 7 of at least 91%, e.g., at least 92%, at least 93%, at least 94%, at least 95%, at least 96%, at least 97%, at least 98%, at least 99%, or 100%. In a further embodiment, the polypeptide has been isolated.

In an embodiment of the fifth aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the fifth aspect, the invention relates to variants of SEQ ID NO: 9 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 9 is not more than 18, e.g., 1, 2, 3, 4, 5, 6, 7, 8, 9, 10, 11, 12, 13, 14, 15, 16, 17 or 18. In an embodiment, the number of positions comprising one or more amino acid substitutions, and/or one or more amino acid deletions, and/or one or more amino acid insertions or any combination thereof in SEQ ID NO: 9 is not more than 10, e.g., 1, 2, 3, 4, 5, 6, 7, 8, 9 or 10. In another embodiment, the number of substitutions and/or deletions and/or insertions in SEQ ID NO: 9 is not more than 10, e.g., 1, 2, 3, 4, 5, 6, 7, 8, 9 or 10. In a further embodiment, the number of substitutions, preferably conservative substitutions, in SEQ ID NO: 9 is not more than 10, e.g., 1, 2, 3, 4, 5, 6, 7, 8, 9 or 10. Examples of amino acid changes and conservative substitutions are described in the third aspect of the invention.

In an embodiment of the fifth aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the GH25 polypeptide comprises the motif F[I/L/V][A/S][H/N/S]GGGWS (SEQ ID NO: 43). In one embodiment, the polypeptide may be a hybrid polypeptide or a fusion polypeptide.

In a sixth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 11. In one embodiment, the polypeptides differ by up to 40 amino acids, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 11.

In a continuation of the sixth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12. In one embodiment, the polypeptides differ by up to 40 amino acids, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 12.

In one embodiment, the invention relates to polypeptides having lysozyme activity and having a sequence identity to SEQ ID NO: 12 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 12 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 12 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 12 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 11. In another embodiment, the polypeptide comprises or consists of the mature polypeptide of SEQ ID NO: 11. In another embodiment, the polypeptide comprises or consists of amino acids 1 to 203 of SEQ ID NO: 11. In one embodiment, the polypeptide preferably comprises or consists of the amino acid sequence of SEQ ID NO: 12; comprises the amino acid sequence of SEQ ID NO: 12 and a N-terminal and/or C-terminal His-tag and/or HQ-tag; comprises the amino acid sequence of SEQ ID NO: 12 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 12. In another embodiment, the polypeptide comprises or consists of amino acids 1 to 203 of SEQ ID NO: 12. In an embodiment, the polypeptide has been isolated.

In a continuation of the sixth aspect, the invention relates to a polypeptide having lysozyme activity encoded by a polynucleotide having a sequence identity to the mature polypeptide coding sequence of SEQ ID NO: 10 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the sixth aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the sixth aspect, the invention relates to variants of SEQ ID NO: 12 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 12 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 12 is not more than 10, e.g., 1, 2, 3, 4, 5, 6, 7, 8, 9 or 10. In another embodiment, the number of substitutions and/or deletions and/or insertions in SEQ ID NO: 12 is not more than 10, e.g., 1, 2, 3, 4, 5, 6, 7, 8, 9 or 10. In a further embodiment, the number of substitutions, preferably conservative substitutions, in SEQ ID NO: 12 is not more than 10, e.g., 1, 2, 3, 4, 5, 6, 7, 8, 9 or 10. Examples of amino acid changes and conservative substitutions are described in the third aspect of the invention.

In an embodiment of the sixth aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the GH25 polypeptide comprises the motif F[I/L/V][A/S][H/N/S]GGGWS (SEQ ID NO: 43). In one embodiment, the polypeptide may be a hybrid polypeptide or a fusion polypeptide.

In a seventh aspect the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 14. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from the mature polypeptide of SEQ ID NO: 14.

In a continuation of the seventh aspect, the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from the mature polypeptide of SEQ ID NO: 15.

In one embodiment, the invention relates to polypeptides having lysozyme activity and having a sequence identity to SEQ ID NO: 15 of at least 86% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 15 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 15 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 14. In another embodiment, the polypeptide comprises or consists of the mature polypeptide of SEQ ID NO: 14. In another embodiment, the polypeptide comprises or consists of amino acids 1 to 204 of SEQ ID NO: 14. In one embodiment, the polypeptide preferably comprises or consists of the amino acid sequence of SEQ ID NO: 15; comprises the amino acid sequence of SEQ ID NO: 15 and a N-terminal and/or C-terminal His-tag and/or HQ-tag; comprises the amino acid sequence of SEQ ID NO: 15 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 15. In another embodiment, the polypeptide comprises or consists of amino acids 1 to 204 of SEQ ID NO: 15. In an embodiment, the polypeptide has been isolated.

In a continuation of the seventh aspect, the invention relates to a polypeptide having lysozyme activity encoded by a polynucleotide having a sequence identity to the mature polypeptide coding sequence of SEQ ID NO: 13 of at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the seventh aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the seventh aspect, the invention relates to variants of SEQ ID NO: 15 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 15 is not more than 28, e.g., 1, 2, 3, 4, 5, 6, 7, 8, 9, 10, 11, 12, 13, 14, 15, 16, 17, 18, 19, 20, 21, 22, 23, 24, 25, 26, 27 or 28. In an embodiment, the number of positions comprising one or more amino acid substitutions, and/or one or more amino acid deletions, and/or one or more amino acid insertions or any combination thereof in SEQ ID NO: 15 is not more than 10, e.g., 1, 2, 3, 4, 5, 6, 7, 8, 9 or 10. In another embodiment, the number of substitutions and/or deletions and/or insertions in SEQ ID NO: 15 is not more than 10, e.g., 1, 2, 3, 4, 5, 6, 7, 8, 9 or 10. In a further embodiment, the number of substitutions, preferably conservative substitutions, in SEQ ID NO: 15 is not more than 10, e.g., 1, 2, 3, 4, 5, 6, 7, 8, 9 or 10. Examples of amino acid changes and conservative substitutions are described in the third aspect of the invention.

In an embodiment of the seventh aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the GH25 polypeptide comprises the motif F[I/L/V][A/S][H/N/S]GGGWS (SEQ ID NO: 43). In one embodiment, the polypeptide may be a hybrid polypeptide or a fusion polypeptide.

In an eighth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 20. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 20.

In a continuation of the eighth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 21.

In one embodiment, the invention relates to polypeptides having lysozyme activity and having a sequence identity to SEQ ID NO: 21 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 21 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 21 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 21 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 20. In another embodiment, the polypeptide comprises or consists of the mature polypeptide of SEQ ID NO: 20. In another embodiment, the polypeptide comprises or consists of amino acids 1 to 207 of SEQ ID NO: 20. In one embodiment, the polypeptide preferably comprises or consists of the amino acid sequence of SEQ ID NO: 21; comprises the amino acid sequence of SEQ ID NO: 21 and a N-terminal and/or C-terminal His-tag and/or HQ-tag; comprises the amino acid sequence of SEQ ID NO: 21 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 21. In another embodiment, the polypeptide comprises or consists of amino acids 1 to 207 of SEQ ID NO: 21. In an embodiment, the polypeptide has been isolated.

In a continuation of the eighth aspect, the invention relates to a polypeptide having lysozyme activity encoded by a polynucleotide having a sequence identity to the mature polypeptide coding sequence of SEQ ID NO: 19 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the eighth aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the eighth aspect, the invention relates to variants of SEQ ID NO: 21 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 21 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 21 is not more than 10, e.g., 1, 2, 3, 4, 5, 6, 7, 8, 9 or 10. In another embodiment, the number of substitutions and/or deletions and/or insertions in SEQ ID NO: 21 is not more than 10, e.g., 1, 2, 3, 4, 5, 6, 7, 8, 9 or 10. In a further embodiment, the number of substitutions, preferably conservative substitutions, in SEQ ID NO: 21 is not more than 10, e.g., 1, 2, 3, 4, 5, 6, 7, 8, 9 or 10. Examples of amino acid changes and conservative substitutions are described in the third aspect of the invention.

In an embodiment of the eighth aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the GH25 polypeptide comprises the motif F[I/L/V][A/S][H/N/S]GGGWS (SEQ ID NO: 43). In one embodiment, the polypeptide may be a hybrid polypeptide or a fusion polypeptide.

In an ninth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 23. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 23.

In a continuation of the ninth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 24. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 24.

In one embodiment, the invention relates to polypeptides having lysozyme activity and having a sequence identity to SEQ ID NO: 24 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 24 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 24 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 24 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 23. In another embodiment, the polypeptide comprises or consists of the mature polypeptide of SEQ ID NO: 23. In another embodiment, the polypeptide comprises or consists of amino acids 1 to 207 of SEQ ID NO: 23. In one embodiment, the polypeptide preferably comprises or consists of the amino acid sequence of SEQ ID NO: 24; comprises the amino acid sequence of SEQ ID NO: 24 and a N-terminal and/or C-terminal His-tag and/or HQ-tag; comprises the amino acid sequence of SEQ ID NO: 24 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 24. In another embodiment, the polypeptide comprises or consists of amino acids 1 to 207 of SEQ ID NO: 24. In an embodiment, the polypeptide has been isolated.

In a continuation of the ninth aspect, the invention relates to a polypeptide having lysozyme activity encoded by a polynucleotide having a sequence identity to the mature polypeptide coding sequence of SEQ ID NO: 22 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the ninth aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the ninth aspect, the invention relates to variants of SEQ ID NO: 24 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 24 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 24 is not more than 10, e.g., 1, 2, 3, 4, 5, 6, 7, 8, 9 or 10. In another embodiment, the number of substitutions and/or deletions and/or insertions in SEQ ID NO: 24 is not more than 10, e.g., 1, 2, 3, 4, 5, 6, 7, 8, 9 or 10. In a further embodiment, the number of substitutions, preferably conservative substitutions, in SEQ ID NO: 24 is not more than 10, e.g., 1, 2, 3, 4, 5, 6, 7, 8, 9 or 10. Examples of amino acid changes and conservative substitutions are described in the third aspect of the invention.

In an embodiment of the ninth aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the GH25 polypeptide comprises the motif F[I/L/V][A/S][H/N/S]GGGWS (SEQ ID NO: 43). In one embodiment, the polypeptide may be a hybrid polypeptide or a fusion polypeptide.

In a tenth aspect the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 26. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from the mature polypeptide of SEQ ID NO: 26.

In a continuation of the tenth aspect, the invention relates to polypeptides having lysozyme activity having at least 87%, e.g., at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from the mature polypeptide of SEQ ID NO: 27.

In one embodiment, the invention relates to polypeptides having lysozyme activity and having a sequence identity to SEQ ID NO: 27 of at least 87% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 27 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 27 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 26. In another embodiment, the polypeptide comprises or consists of the mature polypeptide of SEQ ID NO: 26. In another embodiment, the polypeptide comprises or consists of amino acids 1 to 216 of SEQ ID NO: 26. In one embodiment, the polypeptide preferably comprises or consists of the amino acid sequence of SEQ ID NO: 27; comprises the amino acid sequence of SEQ ID NO: 27 and a N-terminal and/or C-terminal His-tag and/or HQ-tag; comprises the amino acid sequence of SEQ ID NO: 27 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 27. In another embodiment, the polypeptide comprises or consists of amino acids 1 to 216 of SEQ ID NO: 27. In one embodiment, the polypeptide has been isolated.

In a continuation of the tenth aspect, the invention relates to a polypeptide having lysozyme activity encoded by a polynucleotide having a sequence identity to the mature polypeptide coding sequence of SEQ ID NO: 25 of at least 87%, e.g., at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the tenth aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the tenth aspect, the invention relates to variants of SEQ ID NO: 27 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 27 is not more than 28, e.g., 1, 2, 3, 4, 5, 6, 7, 8, 9, 10, 11, 12, 13, 14, 15, 16, 17, 18, 19, 20, 21, 22, 23, 24, 25, 26, 27 or 28. In an embodiment, the number of positions comprising one or more amino acid substitutions, and/or one or more amino acid deletions, and/or one or more amino acid insertions or any combination thereof in SEQ ID NO: 27 is not more than 10, e.g., 1, 2, 3, 4, 5, 6, 7, 8, 9 or 10. In another embodiment, the number of substitutions and/or deletions and/or insertions in SEQ ID NO: 27 is not more than 10, e.g., 1, 2, 3, 4, 5, 6, 7, 8, 9 or 10. In a further embodiment, the number of substitutions, preferably conservative substitutions, in SEQ ID NO: 27 is not more than 10, e.g., 1, 2, 3, 4, 5, 6, 7, 8, 9 or 10. Examples of amino acid changes and conservative substitutions are described in the third aspect of the invention.

In an embodiment of the tenth aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the GH25 polypeptide comprises the motif F[I/L/V][A/S][H/N/S]GGGWS (SEQ ID NO: 43). In one embodiment, the polypeptide may be a hybrid polypeptide or a fusion polypeptide.

In an eleventh aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 29. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 29.

In a continuation of the eleventh aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 30.

In one embodiment, the invention relates to polypeptides having lysozyme activity and having a sequence identity to SEQ ID NO: 30 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 30 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 30 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 30 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 29. In another embodiment, the polypeptide comprises or consists of the mature polypeptide of SEQ ID NO: 29. In another embodiment, the polypeptide comprises or consists of amino acids 1 to 217 of SEQ ID NO: 29. In one embodiment, the polypeptide preferably comprises or consists of the amino acid sequence of SEQ ID NO: 30; comprises the amino acid sequence of SEQ ID NO: 30 and a N-terminal and/or C-terminal His-tag and/or HQ-tag; comprises the amino acid sequence of SEQ ID NO: 30 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 30. In another embodiment, the polypeptide comprises or consists of amino acids 1 to 217 of SEQ ID NO: 30. In an embodiment, the polypeptide has been isolated.

In a continuation of the eleventh aspect, the invention relates to a polypeptide having lysozyme activity encoded by a polynucleotide having a sequence identity to the mature polypeptide coding sequence of SEQ ID NO: 28 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the eleventh aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the eleventh aspect, the invention relates to variants of SEQ ID NO: 30 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 30 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 30 is not more than 10, e.g., 1, 2, 3, 4, 5, 6, 7, 8, 9 or 10. In another embodiment, the number of substitutions and/or deletions and/or insertions in SEQ ID NO: 30 is not more than 10, e.g., 1, 2, 3, 4, 5, 6, 7, 8, 9 or 10. In a further embodiment, the number of substitutions, preferably conservative substitutions, in SEQ ID NO: 30 is not more than 10, e.g., 1, 2, 3, 4, 5, 6, 7, 8, 9 or 10. Examples of amino acid changes and conservative substitutions are described in the third aspect of the invention.

In an embodiment of the eleventh aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX [Q/T]CTG (SEQ ID NO: 42). In one embodiment, the GH25 polypeptide comprises the motif F[I/L/V][A/S][H/N/S]GGGWS (SEQ ID NO: 43). In one embodiment, the polypeptide may be a hybrid polypeptide or a fusion polypeptide.

In a twelfth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 32. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 32.

In a continuation of the twelfth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 33. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 33.

In one embodiment, the invention relates to polypeptides having lysozyme activity and having a sequence identity to SEQ ID NO: 33 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 33 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 33 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 33 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 32. In another embodiment, the polypeptide comprises or consists of the mature polypeptide of SEQ ID NO: 32. In another embodiment, the polypeptide comprises or consists of amino acids 1 to 207 of SEQ ID NO: 32. In one embodiment, the polypeptide preferably comprises or consists of the amino acid sequence of SEQ ID NO: 33; comprises the amino acid sequence of SEQ ID NO: 33 and a N-terminal and/or C-terminal His-tag and/or HQ-tag; comprises the amino acid sequence of SEQ ID NO: 33 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 33. In another embodiment, the polypeptide comprises or consists of amino acids 1 to 207 of SEQ ID NO: 33. In an embodiment, the polypeptide has been isolated.

In a continuation of the twelfth aspect, the invention relates to a polypeptide having lysozyme activity encoded by a polynucleotide having a sequence identity to the mature polypeptide coding sequence of SEQ ID NO: 31 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twelfth aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the twelfth aspect, the invention relates to variants of SEQ ID NO: 33 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 33 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 33 is not more than 10, e.g., 1, 2, 3, 4, 5, 6, 7, 8, 9 or 10. In another embodiment, the number of substitutions and/or deletions and/or insertions in SEQ ID NO: 33 is not more than 10, e.g., 1, 2, 3, 4, 5, 6, 7, 8, 9 or 10. In a further embodiment, the number of substitutions, preferably conservative substitutions, in SEQ ID NO: 33 is not more than 10, e.g., 1, 2, 3, 4, 5, 6, 7, 8, 9 or 10. Examples of amino acid changes and conservative substitutions are described in the third aspect of the invention.

In an embodiment of the twelfth aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO:

40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX [Q/T]CTG (SEQ ID NO: 42). In one embodiment, the GH25 polypeptide comprises the motif F[I/L/V][A/S][H/N/S] GGGWS (SEQ ID NO: 43). In one embodiment, the polypeptide may be a hybrid polypeptide or a fusion polypeptide.

In a thirteenth aspect the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 35. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34 or 35 amino acids from the mature polypeptide of SEQ ID NO: 35.

In a continuation of the thirteenth aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 37. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34 or 35 amino acids from the mature polypeptide of SEQ ID NO: 37.

In a continuation of the thirteenth aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 38. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34 or 35 amino acids from SEQ ID NO: 38.

In one embodiment, the invention relates to polypeptides having lysozyme activity and having a sequence identity to SEQ ID NO: 38 of at least 83% and wherein the polypeptide has at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 38 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 38 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39. In one embodiment, the invention relates to polypeptides having lysozyme activity and having a sequence identity to SEQ ID NO: 38 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 39.

In one embodiment, the polypeptide preferably comprises or consists of the amino acid sequence of SEQ ID NO: 35. In another embodiment, the polypeptide comprises or consists of the mature polypeptide of SEQ ID NO: 35. In another embodiment, the polypeptide comprises or consists of amino acids 1 to 208 of SEQ ID NO: 35. In one embodiment, the polypeptide preferably comprises or consists of the amino acid sequence of SEQ ID NO: 37. In another embodiment, the polypeptide comprises or consists of the mature polypeptide of SEQ ID NO: 37. In another embodiment, the polypeptide comprises or consists of amino acids 1 to 208 of SEQ ID NO: 37. In one embodiment, the polypeptide preferably comprises or consists of the amino acid sequence of SEQ ID NO: 38; comprises the amino acid sequence of SEQ ID NO: 38 and a N-terminal and/or C-terminal His-tag and/or HQ-tag; comprises the amino acid sequence of SEQ ID NO: 38 and a N-terminal and/or C-terminal extension of between 1 and 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 38. In another embodiment, the polypeptide comprises or consists of amino acids 1 to 208 of SEQ ID NO: 38. In an embodiment, the polypeptide has been isolated.

In a continuation of the thirteenth aspect, the invention relates to a polypeptide having lysozyme activity encoded by a polynucleotide having a sequence identity to the mature polypeptide coding sequence of SEQ ID NO: 34 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirteenth aspect, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In a continuation of the thirteenth aspect, the invention relates to variants of SEQ ID NO: 38 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 38 is not more than 35, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35. In an embodiment, the number of positions comprising one or more amino acid substitutions, and/or one or more amino acid deletions, and/or one or more amino acid insertions or any combination thereof in SEQ ID NO: 38 is not more than 10, e.g., 1, 2, 3, 4, 5, 6, 7, 8, 9 or 10. In another embodiment, the number of substitutions and/or deletions and/or insertions in SEQ ID NO: 38 is not more than 10, e.g., 1, 2, 3, 4, 5, 6, 7, 8, 9 or 10. In a further embodiment, the number of substitutions, preferably conservative substitutions, in SEQ ID NO: 38 is not more than 10, e.g., 1, 2, 3, 4, 5, 6, 7, 8, 9 or 10. Examples of amino acid changes and conservative substitutions are described in the third aspect of the invention.

In an embodiment of the thirteenth aspect, the variant has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In one embodiment, the GH25 polypeptide comprises the motif F[I/L/V][A/S/K][H/N/S]GGGW[S/T] (SEQ ID NO: 40) and/or the motif DGXTLPG (SEQ ID NO: 41) and/or the motif WWX[Q/T]CTG (SEQ ID NO: 42). In one embodiment, the GH25 polypeptide comprises the motif F[I/L/V][A/S/K][H/N/S]GGGWS (SEQ ID NO: 40), the motif DGXTLPG (SEQ ID NO: 41) and the motif WWX[Q/T]CTG (SEQ ID NO: 42). In one embodiment, the GH25 polypeptide comprises the motif F[I/L/V][A/S][H/N/S]GGGWS (SEQ ID NO: 43). In one embodiment, the polypeptide may be a hybrid polypeptide or a fusion polypeptide.

Lysozyme Activity

The polypeptides of the invention have lysozyme activity. The polypeptides of the invention have improved lysozyme activity, as measured by conventional methods, compared to hen eggwhite lysozyme. Furthermore, as shown in the Examples, the polypeptides of the invention have improved lysozyme activity compared to a known active lysozyme, the lysozyme of SEQ ID NO 39. Accordingly, one embodiment of the invention relates to the polypeptides of the invention wherein the polypeptide has improved lysozyme activity a) compared to the lysozyme activity of hen eggwhite lysozyme (HEWL) or b) compared to the lysozyme activity of SEQ ID NO: 39 as determined by the Method for the Determination of Lysozyme Activity Against *Micrococcus lysodeikticus* (the Method for the Determination of Lysozyme Activity Against *Micrococcus lysodeikticus* is described in detail in Example 1 and the comparative results are shown in Example 16).

A further embodiment relates to a polypeptide of the invention having improved lysozyme activity a) compared to the lysozyme activity of hen eggwhite lysozyme (HEWL) or b) compared to the lysozyme activity of SEQ ID NO: 39 as determined by any one of i) Method for the Determination of Lysozyme Activity Against *Micrococcus lysodeikticus* and ii) Method for the Determination of Lysozyme Activity Against *Lactobacillus johnsonii*. As can be seen in the Examples, the lysozyme activity of hen eggwhite lysozyme (HEWL) increases optical density (OD) measurement at 405 nm by an average of 0.180 at a concentration of 5 mg enzyme protein/L in the Method for the Determination of Lysozyme Activity Against *Micrococcus lysodeikticus*. Using the known SEQ ID NO 39, the lysozyme activity of SEQ ID NO 39 was found to increase optical density (OD) measurements at 405 nm by an average of 0.186 at a concentration of 5 mg enzyme protein/L in the Method for the Determination of Lysozyme Activity Against *Micrococcus lysodeikticus*.

An alternative measurement of the lysozyme activity is the reducing end method as performed according to the Method for the Determination of Lysozyme Activity Against *Lactobacillus johnsonii*. In an embodiment of the invention, the polypeptide of the invention has a lysozyme activity against *Lactobacillus johnsonii* at 5 ppm that increases optical density (OD) measurement at 405 nm of at least 0.20 as determined by Method for the Determination of Lysozyme Activity Against *Lactobacillus johnsonii*.

Sources of Polypeptides Having Lysozyme Activity

A polypeptide having lysozyme activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In another aspect, the polypeptide may be a fungal polypeptide. In one aspect, the polypeptide is a polypeptide having lysozyme activity from a fungus of the class Sordariomycetes, such as from the order Hypocreales, or from the family Clavicipitaceae, or from the genus *Paecilomyces* or from the species *Paecilomyces* sp. XZ2658.

In another aspect, the polypeptide may be a fungal polypeptide. In one aspect, the polypeptide is a polypeptide having lysozyme activity from a fungus of the class Eurotiomycetes, such as from the order Onygenales, or from the genus *Malbranchea* or from the species *Malbranchea flava*.

In another aspect, the polypeptide may be a fungal polypeptide. In one aspect, the polypeptide is a polypeptide having lysozyme activity from a fungus of the phylum Ascomycota, such as from the genus *Engyodontium* or from the species *Engyodontium* album.

In another aspect, the polypeptide may be a fungal polypeptide. In one aspect, the polypeptide is a polypeptide having lysozyme activity from a fungus of the class Agaricomycetes, such as from the order Agaricales, or from the genus *Flammulina* or from the species *Flammulina velutipes* KACC42780.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Penicillium* or from the species *Penicillium* sp. 'qii' or *Penicillium atrovenetum*.

In another aspect, the polypeptide may be a fungal polypeptide. In one aspect, the polypeptide is a polypeptide having lysozyme activity from a fungus of the class Eurotiomycetes, such as from the order Onygenales, or from the family Onygenaceae, or from the genus *Onygena* or from the species *Onygena equina*.

In another aspect, the polypeptide may be a fungal polypeptide. In one aspect, the polypeptide is a polypeptide having lysozyme activity from a fungus of the class Sordariomycetes, such as from the order Hypocreales, or from the family Cordycipitaceae, or from the genus *Lecanicillium* or from the species *Lecanicillium* sp. WMM742.

In another aspect, the polypeptide may be a fungal polypeptide. In one aspect, the polypeptide is a polypeptide having lysozyme activity from a fungus of the subphylum Mortierellomycotina, such as from the order Mortierellales, or from the family Mortierellaceae, or from the genus *Mortierella* or from the species *Mortierella alpina*.

In another aspect, the polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Myceliophthora* or from the species *Myceliophthora fergusii*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of Trichophaea or a strain of Trichoderma, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the Bacillus amyloliquefaciens alpha-amylase gene (amyQ), Bacillus licheniformis alpha-amylase gene (amyL), Bacillus licheniformis penicillinase gene (penP), Bacillus stearothermophilus maltogenic amylase gene (amyM), Bacillus subtilis levansucrase gene (sacB), Bacillus subtilis xylA and xylB genes, Bacillus thuringiensis cryIIIA gene (Agaisse and Lereclus, 1994, Molecular Microbiology 13: 97-107), E. coli lac operon, E. coli trc promoter (Egon et al., 1988, Gene 69: 301-315), Streptomyces coelicolor agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for Aspergillus nidulans acetamidase, Aspergillus niger neutral alpha-amylase, Aspergillus niger acid stable alpha-amylase, Aspergillus niger or Aspergillus awamori glucoamylase (glaA), Aspergillus oryzae TAKA amylase, Aspergillus oryzae alkaline protease, Aspergillus oryzae triose phosphate isomerase, Fusarium oxysporum trypsin-like protease (WO 96/00787), Fusarium venenatum amyloglucosidase (WO 00/56900), Fusarium venenatum Dania (WO 00/56900), Fusarium venenatum Quinn (WO 00/56900), Rhizomucor miehei lipase, Rhizomucor miehei aspartic proteinase, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor, as well as the NA2-tpi promoter (a modified promoter from an Aspergillus neutral alpha-amylase gene in which the untranslated leader has been replaced by an untranslated leader from an Aspergillus triose phosphate isomerase gene; non-limiting examples include modified promoters from an Aspergillus niger neutral alpha-amylase gene in which the untranslated leader has been replaced by an untranslated leader from an Aspergillus nidulans or Aspergillus oryzae triose phosphate isomerase gene); and mutant, truncated, and hybrid promoters thereof. Other promoters are described in U.S. Pat. No. 6,011,147.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoim idazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

In some embodiments, the polypeptide is heterologous to the recombinant host cell.

In some embodiments, at least one of the one or more control sequences is heterologous to the polynucleotide encoding the polypeptide.

In some embodiments, the recombinant host cell comprises at least two copies, e.g., three, four, or five, of the polynucleotide of the present invention.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta,*

*Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide In one aspect, the cell is a *Paecilomyces* sp. XZ2658 cell. In one aspect, the cell is a *Malbranchea flava* cell. In one aspect, the cell is a *Engyodontium* album cell. In one aspect, the cell is a *Flammulina velutipes* KACC42780 cell. In one aspect, the cell is a *Penicillium* sp. 'qii' cell. In one aspect, the cell is a *Penicillium atrovenetum* cell. In one aspect, the cell is a *Onygena equina* cell. In one aspect, the cell is a *Lecanicillium* sp. WMM742 cell. In one aspect, the cell is a *Mortierella alpina* cell. In one aspect, the cell is a *Myceliophthora fergusii* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the fermentation medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor. The transgenic plant can be dicotyledonous (a dicot) or monocotyledonous (a monocot).

Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In some embodiments, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In some embodiments, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in the polypeptide of the invention. The term "enriched" indicates that the lysozyme activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In a preferred embodiment, the composition comprises one or more lysozymes selected from the list consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33 and SEQ ID NO: 38.

In an embodiment, the composition comprises the polypeptide of the invention and one or more formulating agents, as described below.

The compositions may further comprise multiple enzymatic activities, such as one or more (e.g., several) enzymes selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

The compositions may further comprise one or more probiotics. In an embodiment, the probiotic is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

In an embodiment, the composition comprises one or more formulating agents as disclosed herein, preferably one or more of the compounds selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

In an embodiment, the composition comprises one or more components selected from the list consisting of vitamins, minerals and amino acids.

Formulation

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the lysozyme of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the lysozyme of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments the thickness of the coating is below 100 µm, such as below 60 µm, or below 40 µm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 µm, such as less than 10 µm or less than 5 µm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)2HPO4 (CH20° C.=93.0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H20), zinc sulfate heptahydrate (ZnSO4.7H20), sodium phosphate dibasic heptahydrate (Na2HPO4.7H20), magnesium nitrate hexahydrate (Mg(NO3)2(6H20)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the lysozyme of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:
(a) a core comprising a lysozyme according to the invention, and
(b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

Animal Feed Additives

The present invention also relates to animal feed additives comprising one or more lysozymes of the invention. Thus in one embodiment, the invention relates to an animal feed additive comprising one or more GH25 polypeptides having lysozyme activity, wherein the polypeptide is selected from the group consisting of:
(a) a polypeptide having at least 90%, such as at least 95% sequence identity to the polypeptide of SEQ ID NO: 3;
(b) a polypeptide having at least 80%, such as at least 85%, at least 90% or at least 95% sequence identity to the polypeptide of SEQ ID NO: 6;
(c) a polypeptide having at least 80%, such as at least 85%, at least 90% or at least 95% sequence identity to the polypeptide of SEQ ID NO: 9;
(d) a polypeptide having at least 80%, such as at least 85%, at least 90% or at least 95% sequence identity to the polypeptide of SEQ ID NO: 12;
(e) a polypeptide having at least 80%, such as at least 85%, at least 90% or at least 95% sequence identity to the polypeptide of SEQ ID NO: 15;
(f) a polypeptide having at least 80%, such as at least 85%, at least 90% or at least 95% sequence identity to the polypeptide of SEQ ID NO: 18;
(g) a polypeptide having at least 80%, such as at least 85%, at least 90% or at least 95% sequence identity to the polypeptide of SEQ ID NO: 21;
(h) a polypeptide having at least 80%, such as at least 85%, at least 90% or at least 95% sequence identity to the polypeptide of SEQ ID NO: 24;
(i) a polypeptide having at least 80%, such as at least 85%, at least 90% or at least 95% sequence identity to the polypeptide of SEQ ID NO: 27;
(j) a polypeptide having at least 80%, such as at least 85%, at least 90% or at least 95% sequence identity to the polypeptide of SEQ ID NO: 30;
(k) a polypeptide having at least 80%, such as at least 85%, at least 90% or at least 95% sequence identity to the polypeptide of SEQ ID NO: 33;
(l) a polypeptide having at least 83%, such as at least 85%, at least 90% or at least 95% sequence identity to the polypeptide of SEQ ID NO: 38;
(m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(n) a polypeptide comprising the polypeptide of (a), (b), (c), (d), (e), (f), (g), (h), (i), (j), (k), (l) or (m) and a N-terminal and/or C-terminal His-tag and/or HQ-tag;
(o) a polypeptide comprising the polypeptide of (a), (b), (c), (d), (e), (f), (g), (h), (i), (j), (k), (l) or (m) and a N-terminal and/or C-terminal extension of between 1 and 10 amino acids; and
(p) a fragment of the polypeptide of (a), (b), (c), (d), (e), (f), (g), (h), (i), (j), (k), (l) or (m) having lysozyme activity and having at least 90% of the length of the mature polypeptide.

In one embodiment, the one or more GH25 polypeptides comprises the motif F[I/L/V][A/S/K][H/N/S]GGGW (SEQ ID NO: 40).

In an embodiment, the polypeptide comprises or consists of amino acids 1 to 207 of SEQ ID NO: 3, amino acids 1 to 216 of SEQ ID NO: 6, amino acids 1 to 204 of SEQ ID NO: 9, amino acids 1 to 203 of SEQ ID NO: 12, amino acids 1 to 204 of SEQ ID NO: 15, amino acids 1 to 208 of SEQ ID NO: 18, amino acids 1 to 207 of SEQ ID NO: 21, amino acids 1 to 207 of SEQ ID NO: 24, amino acids 1 to 216 of SEQ ID NO: 27, amino acids 1 to 217 of SEQ ID NO: 30, amino acids 1 to 207 of SEQ ID NO: 33 or amino acids 1 to 207 of SEQ ID NO: 38.

In a preferred embodiment, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In an embodiment, the animal feed additive comprises one or more formulating agents, preferably as described herein above.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

Animal Feed

The present invention also relates to animal feed compositions comprising one or more lysozymes of the invention. In one embodiment, the invention relates to an animal feed comprising the granule as described herein and plant based material. In one embodiment, the invention relates to an animal feed comprising the animal feed additive as described herein and plant based material.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one lysozyme as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 D A Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or *quinoa*. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) lysozyme/enzyme preparation may also be added before or during the feed ingredient step. Typically a liquid lysozyme/enzyme preparation comprises the lysozyme of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the lysozyme can be prepared by freezing a mixture of liquid enzyme solution with a bulking agent such as ground soybean meal, and then lyophilizing the mixture.

The final enzyme concentration in the diet is within the range of 0.01-200 mg enzyme protein per kg diet, preferably between 0.05-100 mg/kg diet, more preferably 0.1-50 mg, even more preferably 0.2-20 mg enzyme protein per kg animal diet.

It is at present contemplated that the enzyme is administered in one or more of the following amounts (dosage ranges): 0.01-200; 0.05-100; 0.1-50; 0.2-20; 0.1-1; 0.2-2; 0.5-5; or 1-10;—all these ranges being in mg lysozyme protein per kg feed (ppm).

For determining mg lysozyme protein per kg feed, the lysozyme is purified from the feed composition, and the specific activity of the purified lysozyme is determined using a relevant assay (see under lysozyme activity). The lysozyme activity of the feed composition as such is also determined using the same assay, and on the basis of these two determinations, the dosage in mg lysozyme protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg lysozyme protein in feed additives. Of course, if a sample is available of the lysozyme used for preparing the feed additive or the feed, the specific activity is determined from this sample (no need to purify the lysozyme from the feed composition or the additive).

Thus in a further aspect, the present invention also relates to an animal feed comprising one or more lysozymes of the invention and plant based material. In another aspect, the present invention also relates to an animal feed comprising the animal feed additive of the invention (as described herein above) and plant based material.

Thus in one embodiment, the invention relates to an animal feed additive comprising plant based material and one or more GH25 polypeptides having lysozyme activity, wherein the polypeptide is selected from the group consisting of:
  (a) a polypeptide having at least 90%, such as at least 95% sequence identity to the polypeptide of SEQ ID NO: 3;
  (b) a polypeptide having at least 80%, such as at least 85%, at least 90% or at least 95% sequence identity to the polypeptide of SEQ ID NO: 6;
  (c) a polypeptide having at least 80%, such as at least 85%, at least 90% or at least 95% sequence identity to the polypeptide of SEQ ID NO: 9;
  (d) a polypeptide having at least 80%, such as at least 85%, at least 90% or at least 95% sequence identity to the polypeptide of SEQ ID NO: 12;
  (e) a polypeptide having at least 80%, such as at least 85%, at least 90% or at least 95% sequence identity to the polypeptide of SEQ ID NO: 15;
  (f) a polypeptide having at least 80%, such as at least 85%, at least 90% or at least 95% sequence identity to the polypeptide of SEQ ID NO: 18;
  (g) a polypeptide having at least 80%, such as at least 85%, at least 90% or at least 95% sequence identity to the polypeptide of SEQ ID NO: 21;
  (h) a polypeptide having at least 80%, such as at least 85%, at least 90% or at least 95% sequence identity to the polypeptide of SEQ ID NO: 24;
  (i) a polypeptide having at least 80%, such as at least 85%, at least 90% or at least 95% sequence identity to the polypeptide of SEQ ID NO: 27;
  (j) a polypeptide having at least 80%, such as at least 85%, at least 90% or at least 95% sequence identity to the polypeptide of SEQ ID NO: 30;
  (k) a polypeptide having at least 80%, such as at least 85%, at least 90% or at least 95% sequence identity to the polypeptide of SEQ ID NO: 33;
  (l) a polypeptide having at least 83%, such as at least 85%, at least 90% or at least 95% sequence identity to the polypeptide of SEQ ID NO: 38;
  (m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
  (n) a polypeptide comprising the polypeptide of (a), (b), (c), (d), (e), (f), (g), (h), (i), (j), (k), (l) or (m) and a N-terminal and/or C-terminal His-tag and/or HQ-tag;
  (o) a polypeptide comprising the polypeptide of (a), (b), (c), (d), (e), (f), (g), (h), (i), (j), (k), (l) or (m) and a N-terminal and/or C-terminal extension of between 1 and 10 amino acids; and
  (p) a fragment of the polypeptide of (a), (b), (c), (d), (e), (f), (g), (h), (i), (j), (k), (l) or (m) having lysozyme activity and having at least 90% of the length of the mature polypeptide.

In one embodiment, the one or more GH25 polypeptides comprises the motif F[I/L/V][A/S/K][H/N/S]GGGW (SEQ ID NO: 40).

In an embodiment, the polypeptide comprises or consists of amino acids 1 to 207 of SEQ ID NO: 3, amino acids 1 to 216 of SEQ ID NO: 6, amino acids 1 to 204 of SEQ ID NO: 9, amino acids 1 to 203 of SEQ ID NO: 12, amino acids 1 to 204 of SEQ ID NO: 15, amino acids 1 to 208 of SEQ ID NO: 18, amino acids 1 to 207 of SEQ ID NO: 21, amino acids 1 to 207 of SEQ ID NO: 24, amino acids 1 to 216 of SEQ ID NO: 27, amino acids 1 to 217 of SEQ ID NO: 30, amino acids 1 to 207 of SEQ ID NO: 33 or amino acids 1 to 207 of SEQ ID NO: 38.

In a preferred embodiment, the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test wherein lysozyme activity is determined as described in example 1.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.

In a further embodiment, the animal feed has been pelleted.

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: expasy.ch/enzyme. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al, "The carbohydrate-active enzymes database (CAZy) in 2013", *Nucl. Acids Res*. (1 Jan. 2014) 42 (D1): D490-D495; see also cazy.org.

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41), alpha-mannosidase (EC 3.2.1.24), mannanase (EC 3.2.1.25) and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis:* 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains in the animal feed composition is between $1\times10^9$ and $1\times10^{11}$ CFU/animal/day.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Syncra® (mix enzyme+probiotic, DuPont Animal Nutrition), Ecobiol® and Fecinor® (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and *curcuma* extract.

Examples of commercial products are Crina® (DSM Nutritional Products); Cinergy™' Biacid™, ProHacid™ Classic and ProHacid™ Advance™ (all Promivi/Cargill) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate or sodium butyrate). Examples of commercial products are VevoVitall® (DSM Nutritional Products), Amasil®, Luprisil®, Lupro-Grain®, Lupro-Cid®, Lupro-Mix® (BASF), n-Butyric Acid AF (OXEA) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin C, vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, iodine, selenium and zinc.

Non-limiting examples of macro minerals include calcium, magnesium, phosphorus, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antioxidants, anti-microbial peptides, anti-fungal polypeptides and mycotoxin management compounds.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Antioxidants can be used to limit the number of reactive oxygen species which can be generated such that the level of reactive oxygen species is in balance with antioxidants.

Mycotoxins, such as deoxynivalenol, aflatoxin, zearalenone and fumonisin can be found in animal feed and can result in negative animal performance or illness. Compounds which can manage the levels of mycotoxin, such as via deactivation of the mycotoxin or via binding of the mycotoxin, can be added to the feed to ameliorate these negative effects. Examples of mycotoxin management compounds are Vitafix®, Vitafix Ultra (Nuscience), Mycofix®, Mycofix® Secure, FUMzyme®, Biomin® BBSH, Biomin® MTV (Biomin), Mold-Nil®, Toxy-Nil® and Unike® Plus (Nutriad).

Use in Animal Feed

A lysozyme of the invention may also be used in animal feed, wherein the term "animal" refers to all animals except humans. Examples of animals are mono-gastric animals, e.g. pigs or swine (including, but not limited to, piglets, growing pigs, and sows); poultry (including but not limited to poultry, turkey, duck, quail, guinea fowl, goose, pigeon, squab, chicken, broiler, layer, pullet and chick); fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

In the use according to the invention the lysozymes can be fed to the animal before, after, or simultaneously with the diet. The latter is preferred.

In a particular embodiment, the lysozyme, in the form in which it is added to the feed, or when being included in a feed additive, is well-defined. Well-defined means that the lysozyme preparation is at least 50% pure as determined by Size-exclusion chromatography (see Example 12 of WO 01/58275). In other particular embodiments the lysozyme preparation is at least 60, 70, 80, 85, 88, 90, 92, 94, or at least 95% pure as determined by this method.

A well-defined lysozyme preparation is advantageous. For instance, it is much easier to dose correctly to the feed a lysozyme that is essentially free from interfering or contaminating other lysozymes. The term dose correctly refers in particular to the objective of obtaining consistent and constant results, and the capability of optimizing dosage based upon the desired effect.

For the use in animal feed, however, the lysozyme need not be pure; it may e.g. include other enzymes, in which case it could be termed a lysozyme preparation.

The lysozyme preparation can be (a) added directly to the feed, or (b) it can be used in the production of one or more intermediate compositions such as feed additives or premixes that is subsequently added to the feed (or used in a treatment process). The degree of purity described above refers to the purity of the original lysozyme preparation, whether used according to (a) or (b) above.

The lysozyme of the present invention could also be used in the treatment of necrotic enteritis and/or *Clostridium perfringens*.

Uses

Methods of Improving Animal Performance

In an embodiment, the present invention also relates to a method of improving the performance of an animal comprising administering to the animal the animal feed or the animal feed additive of the invention.

In a preferred embodiment, the method of improving the performance of an animal comprises administering to the animal the animal feed or the animal feed additive comprising the lysozyme selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33 and SEQ ID NO: 38.

In an embodiment, the present invention also relates to the use of the animal feed or an animal feed additive of the invention for improving the performance of an animal. In another embodiment, the invention relates to the use of one or more lysozymes of the invention for improving the performance of an animal.

In one embodiment, 'improving the performance of an animal' means that there is an increase in body weight gain. In another embodiment, 'improving the performance of an animal' means that there is an improved feed conversion ratio. In a further embodiment, 'improving the performance of an animal' means that there is an increased feed efficiency. In a further embodiment, 'improving the performance of an animal' means that there is an increase in body weight gain and/or an improved feed conversion ratio and/or an increased feed efficiency.

In an embodiment, the animal feed comprises plant based material selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.

Methods of Preparing an Animal Feed

In an embodiment, the present invention provides a method for preparing an animal feed comprising adding one or more lysozymes of the present invention to one or more animal feed ingredients. Animal feed ingredients include, but are not limited to concentrates (as defined herein), forage (as defined herein), enzymes, probiotic, vitamins, minerals and amino acids.

In a preferred embodiment, the method of preparing an animal feed comprises mixing plant based material with the lysozyme selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33 and SEQ ID NO: 38.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.

Embodiments of the Invention

Herein follows a list of preferred embodiments of the invention.

1. A method of hydrolysing peptidoglycan in bacterial cell walls comprising treating bacterial cells with one or more GH25 polypeptides having lysozyme activity, wherein the polypeptide is selected from the group consisting of:
   (a) a polypeptide having at least 90% sequence identity to the polypeptide of SEQ ID NO: 3;
   (b) a polypeptide having at least 80% sequence identity to the polypeptide of SEQ ID NO: 6;
   (C) a polypeptide having at least 80% sequence identity to the polypeptide of SEQ ID NO: 9;
   (d) a polypeptide having at least 80% sequence identity to the polypeptide of SEQ ID NO: 12;
   (e) a polypeptide having at least 80% sequence identity to the polypeptide of SEQ ID NO: 15;
   (f) a polypeptide having at least 80% sequence identity to the polypeptide of SEQ ID NO: 18;
   (g) a polypeptide having at least 80% sequence identity to the polypeptide of SEQ ID NO: 21;
   (h) a polypeptide having at least 80% sequence identity to the polypeptide of SEQ ID NO: 24;
   (i) a polypeptide having at least 80% sequence identity to the polypeptide of SEQ ID NO: 27;
   (j) a polypeptide having at least 80% sequence identity to the polypeptide of SEQ ID NO: 30;
   (k) a polypeptide having at least 80% sequence identity to the polypeptide of SEQ ID NO: 33;
   (l) a polypeptide having at least 83% sequence identity to the polypeptide of SEQ ID NO: 38;
   (m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
   (n) a polypeptide comprising the polypeptide of (a), (b), (c), (d), (e), (f), (g), (h), (i), (j), (k), (l) or (m) and a N-terminal and/or C-terminal His-tag and/or HQ-tag;
   (o) a polypeptide comprising the polypeptide of (a), (b), (c), (d), (e), (f), (g), (h), (i), (j), (k), (l) or (m) and a N-terminal and/or C-terminal extension of between 1 and 10 amino acids; and
   (p) a fragment of the polypeptide of (a), (b), (c), (d), (e), (f), (g), (h), (i), (j), (k), (l) or (m) having lysozyme activity and having at least 90% of the length of the mature polypeptide.

2. The method of item 1, wherein the polypeptide is selected from the group consisting of:
   (a) a polypeptide having at least 90% sequence identity to the polypeptide of SEQ ID NO: 3;
   (b) a polypeptide having at least 85% sequence identity to the polypeptide of SEQ ID NO: 6;
   (c) a polypeptide having at least 85% sequence identity to the polypeptide of SEQ ID NO: 9;
   (d) a polypeptide having at least 85% sequence identity to the polypeptide of SEQ ID NO: 12;
   (e) a polypeptide having at least 85% sequence identity to the polypeptide of SEQ ID NO: 15;

(f) a polypeptide having at least 85% sequence identity to the polypeptide of SEQ ID NO: 18;
(g) a polypeptide having at least 85% sequence identity to the polypeptide of SEQ ID NO: 21;
(h) a polypeptide having at least 85% sequence identity to the polypeptide of SEQ ID NO: 24;
(i) a polypeptide having at least 85% sequence identity to the polypeptide of SEQ ID NO: 27;
(j) a polypeptide having at least 85% sequence identity to the polypeptide of SEQ ID NO: 30;
(k) a polypeptide having at least 85% sequence identity to the polypeptide of SEQ ID NO: 33; and
(l) a polypeptide having at least 85% sequence identity to the polypeptide of SEQ ID NO: 38.

3. The method of item 1, wherein the polypeptide is selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 6;
(c) a polypeptide having at least 90% sequence identity to the polypeptide of SEQ ID NO: 9;
(d) a polypeptide having at least 90% sequence identity to the polypeptide of SEQ ID NO: 12;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(i) a polypeptide having at least 90% sequence identity to the polypeptide of SEQ ID NO: 27;
(j) a polypeptide having at least 90% sequence identity to the polypeptide of SEQ ID NO: 30;
(k) a polypeptide having at least 90% sequence identity to the polypeptide of SEQ ID NO: 33; and
(l) a polypeptide having at least 90% sequence identity to the polypeptide of SEQ ID NO: 38.

4. The method of item 1, wherein the polypeptide is selected from the group consisting of:
(a) a polypeptide having at least 95% sequence identity to the polypeptide of SEQ ID NO: 3;
(b) a polypeptide having at least 95% sequence identity to the polypeptide of SEQ ID NO: 6;
(c) a polypeptide having at least 95% sequence identity to the polypeptide of SEQ ID NO: 9;
(d) a polypeptide having at least 95% sequence identity to the polypeptide of SEQ ID NO: 12;
(e) a polypeptide having at least 95% sequence identity to the polypeptide of SEQ ID NO: 15;
(f) a polypeptide having at least 95% sequence identity to the polypeptide of SEQ ID NO: 18;
(g) a polypeptide having at least 95% sequence identity to the polypeptide of SEQ ID NO: 21;
(h) a polypeptide having at least 95% sequence identity to the polypeptide of SEQ ID NO: 24;
(i) a polypeptide having at least 95% sequence identity to the polypeptide of SEQ ID NO: 27;
(j) a polypeptide having at least 95% sequence identity to the polypeptide of SEQ ID NO: 30;
(k) a polypeptide having at least 95% sequence identity to the polypeptide of SEQ ID NO: 33; and
(l) a polypeptide having at least 95% sequence identity to the polypeptide of SEQ ID NO: 38; and (m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9 or 10 positions;

5. The method of any of items 1 to 4, wherein the polypeptide comprises the motif F[I/L/V][A/S/K][H/N/S]GGGW (SEQ ID NO: 40).

6. The method of any of items 1 to 5, wherein the polypeptide comprises or consists of amino acids 1 to 207 of SEQ ID NO: 3, amino acids 1 to 216 of SEQ ID NO: 6, amino acids 1 to 204 of SEQ ID NO: 9, amino acids 1 to 203 of SEQ ID NO: 12, amino acids 1 to 204 of SEQ ID NO: 15, amino acids 1 to 208 of SEQ ID NO: 18, amino acids 1 to 207 of SEQ ID NO: 21, amino acids 1 to 207 of SEQ ID NO: 24, amino acids 1 to 216 of SEQ ID NO: 27, amino acids 1 to 217 of SEQ ID NO: 30, amino acids 1 to 207 of SEQ ID NO: 33 or amino acids 1 to 207 of SEQ ID NO: 38.

7. The method of any of items 1 to 6 wherein the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test.

8. The method of any of items 1 to 6, wherein lysozyme activity is determined by measuring the decrease in optical density of a solution of resuspended *Micrococcus lysodeikticus* cells, preferably *Micrococcus luteus* ATCC 4698 cells.

9. A granule comprising one or more GH25 polypeptides having lysozyme activity, wherein the polypeptide is selected from the group consisting of:
(a) a polypeptide having at least 90% sequence identity to the polypeptide of SEQ ID NO: 3;
(b) a polypeptide having at least 80% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 80% sequence identity to the polypeptide of SEQ ID NO: 30;
(k) a polypeptide having at least 80% sequence identity to the polypeptide of SEQ ID NO: 33;
(l) a polypeptide having at least 83% sequence identity to the polypeptide of SEQ ID NO: 38;
(m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO:

33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
  (n) a polypeptide comprising the polypeptide of (a), (b), (c), (d), (e), (f), (g), (h), (i), (j), (k), (l) or (m) and a N-terminal and/or C-terminal His-tag and/or HQ-tag;
  (o) a polypeptide comprising the polypeptide of (a), (b), (c), (d), (e), (f), (g), (h), (i), (j), (k), (l) or (m) and a N-terminal and/or C-terminal extension of between 1 and 10 amino acids; and
  (p) a fragment of the polypeptide of (a), (b), (c), (d), (e), (f), (g), (h), (i), (j), (k), (l) or (m) having lysozyme activity and having at least 90% of the length of the mature polypeptide.
10. The granule of item 9, wherein the polypeptide is selected from the group consisting of:
  (a) a polypeptide having at least 90% sequence identity to the polypeptide of SEQ ID NO: 3;
  (b) a polypeptide having at least 85% sequence identity to the polypeptide of SEQ ID NO: 6;
  (c) a polypeptide having at least 85% sequence identity to the polypeptide of SEQ ID NO: 9;
  (d) a polypeptide having at least 85% sequence identity to the polypeptide of SEQ ID NO: 12;
  (e) a polypeptide having at least 85% sequence identity to the polypeptide of SEQ ID NO: 15;
  (f) a polypeptide having at least 85% sequence identity to the polypeptide of SEQ ID NO: 18;
  (g) a polypeptide having at least 85% sequence identity to the polypeptide of SEQ ID NO: 21;
  (h) a polypeptide having at least 85% sequence identity to the polypeptide of SEQ ID NO: 24;
  (i) a polypeptide having at least 85% sequence identity to the polypeptide of SEQ ID NO: 27;
  (j) a polypeptide having at least 85% sequence identity to the polypeptide of SEQ ID NO: 30;
  (k) a polypeptide having at least 85% sequence identity to the polypeptide of SEQ ID NO: 33; and
  (l) a polypeptide having at least 85% sequence identity to the polypeptide of SEQ ID NO: 38.
11. The granule of item 9, wherein the polypeptide is selected from the group consisting of:
  (a) a polypeptide having at least 90% sequence identity to the polypeptide of SEQ ID NO: 3;
  (b) a polypeptide having at least 90% sequence identity to the polypeptide of SEQ ID NO: 6;
  (c) a polypeptide having at least 90% sequence identity to the polypeptide of SEQ ID NO: 9;
  (d) a polypeptide having at least 90% sequence identity to the polypeptide of SEQ ID NO: 12;
  (e) a polypeptide having at least 90% sequence identity to the polypeptide of SEQ ID NO: 15;
  (f) a polypeptide having at least 90% sequence identity to the polypeptide of SEQ ID NO: 18;
  (g) a polypeptide having at least 90% sequence identity to the polypeptide of SEQ ID NO: 21;
  (h) a polypeptide having at least 90% sequence identity to the polypeptide of SEQ ID NO: 24;
  (i) a polypeptide having at least 90% sequence identity to the polypeptide of SEQ ID NO: 27;
  (j) a polypeptide having at least 90% sequence identity to the polypeptide of SEQ ID NO: 30;
  (k) a polypeptide having at least 90% sequence identity to the polypeptide of SEQ ID NO: 33; and
  (l) a polypeptide having at least 90% sequence identity to the polypeptide of SEQ ID NO: 38.
12. The granule of item 9, wherein the polypeptide is selected from the group consisting of:
  (a) a polypeptide having at least 95% sequence identity to the polypeptide of SEQ ID NO: 3;
  (b) a polypeptide having at least 95% sequence identity to the polypeptide of SEQ ID NO: 6;
  (c) a polypeptide having at least 95% sequence identity to the polypeptide of SEQ ID NO: 9;
  (d) a polypeptide having at least 95% sequence identity to the polypeptide of SEQ ID NO: 12;
  (e) a polypeptide having at least 95% sequence identity to the polypeptide of SEQ ID NO: 15;
  (f) a polypeptide having at least 95% sequence identity to the polypeptide of SEQ ID NO: 18;
  (g) a polypeptide having at least 95% sequence identity to the polypeptide of SEQ ID NO: 21;
  (h) a polypeptide having at least 95% sequence identity to the polypeptide of SEQ ID NO: 24;
  (i) a polypeptide having at least 95% sequence identity to the polypeptide of SEQ ID NO: 27;
  (j) a polypeptide having at least 95% sequence identity to the polypeptide of SEQ ID NO: 30;
  (k) a polypeptide having at least 95% sequence identity to the polypeptide of SEQ ID NO: 33; and
  (l) a polypeptide having at least 95% sequence identity to the polypeptide of SEQ ID NO: 38; and
  (m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9 or 10 positions;
13. The granule of any of items 9 to 12, wherein the polypeptide comprises the motif F[I/L/V][A/S/K][H/N/S]GGGW (SEQ ID NO: 40).
14. The granule of any of items 9 to 13, wherein the polypeptide comprises or consists of amino acids 1 to 207 of SEQ ID NO: 3, amino acids 1 to 216 of SEQ ID NO: 6, amino acids 1 to 204 of SEQ ID NO: 9, amino acids 1 to 203 of SEQ ID NO: 12, amino acids 1 to 204 of SEQ ID NO: 15, amino acids 1 to 208 of SEQ ID NO: 18, amino acids 1 to 207 of SEQ ID NO: 21, amino acids 1 to 207 of SEQ ID NO: 24, amino acids 1 to 216 of SEQ ID NO: 27, amino acids 1 to 217 of SEQ ID NO: 30, amino acids 1 to 207 of SEQ ID NO: 33 or amino acids 1 to 207 of SEQ ID NO: 38.
15. The granule of any of items 9 to 14, wherein the polypeptide has significantly improved lysozyme activity compared to the activity of SEQ ID NO: 39, wherein the significance is <0.05, preferably <0.04, more preferably <0.03, even preferably <0.02 or most preferably <0.01 as determined using Dunnett's test.
16. The granule of item 15, wherein lysozyme activity is determined by measuring the decrease in optical density of a solution of resuspended *Micrococcus lysodeikticus* cells, preferably *Micrococcus luteus* ATCC 4698 cells.
17. The granule of any of items 9 to 16, wherein the granule comprises one or more formulating agents.
18. The granule of item 17, wherein the formulating agent is selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose, preferably selected from the list consisting of 1, 2-propylene glycol, 1, 3-propylene glycol, sodium sulfate, dextrin, cellulose, sodium thiosulfate, kaolin and calcium carbonate.

19. The granule of any of items 9 to 18, wherein the granule comprises a core particle and one or more coatings.
20. The granule of item 19, wherein the coating comprises salt and/or wax and/or flour.
21. The granule of any of items 9 to 20 further comprising one or more additional enzymes.
22. The granule of item 21, wherein the one or more additional enzymes is selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.
23. The granule of any of items 9 to 22 further comprising one or more probiotics.
24. The granule of item 23, wherein the one or more probiotics is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium sp., Carnobacterium sp., Clostridium butyricum, Clostridium sp., Enterococcus faecium, Enterococcus sp., Lactobacillus sp., Lactobacillus acidophilus, Lactobacillus farciminus, Lactobacillus rhamnosus, Lactobacillus reuteri, Lactobacillus salivarius, Lactococcus lactis, Lactococcus sp., Leuconostoc sp., Megasphaera elsdenii, Megasphaera sp., Pediococcus acidilactici, Pediococcus sp., Propionibacterium thoenii, Propionibacterium sp.* and *Streptococcus* sp. or any combination thereof.
25. An isolated polypeptide having lysozyme activity, selected from the group consisting of:
    (a) a polypeptide having at least 90% sequence identity to the polypeptide of SEQ ID NO: 3;
    (b) a polypeptide having at least 85% sequence identity to the polypeptide of SEQ ID NO: 6;
    (c) a polypeptide having at least 91% sequence identity to the polypeptide of SEQ ID NO: 9;
    (d) a polypeptide having at least 80% sequence identity to the polypeptide of SEQ ID NO: 12;
    (e) a polypeptide having at least 86% sequence identity to the polypeptide of SEQ ID NO: 15;
    (f) a polypeptide having at least 80% sequence identity to the polypeptide of SEQ ID NO: 21;
    (g) a polypeptide having at least 80% sequence identity to the polypeptide of SEQ ID NO: 24;
    (h) a polypeptide having at least 87% sequence identity to the polypeptide of SEQ ID NO: 27;
    (i) a polypeptide having at least 80% sequence identity to the polypeptide of SEQ ID NO: 30;
    (j) a polypeptide having at least 80% sequence identity to the polypeptide of SEQ ID NO: 33;
    (k) a polypeptide having at least 83% sequence identity to the polypeptide of SEQ ID NO: 38;
    (l) a variant of the polypeptide of SEQ ID NO: 3, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
    (m) a variant of the polypeptide of SEQ ID NO: 6, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 positions;
    (n) a variant of the polypeptide of SEQ ID NO: 9, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17 or 18 positions;
    (o) a variant of the polypeptide selected from the group consisting of SEQ ID NO: 12, SEQ ID NO: 21, SEQ ID NO: 24, SEQ ID NO: 30 and SEQ ID NO: 33, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 positions;
    (p) a variant of the polypeptide selected from the group consisting of SEQ ID NO: 15 and SEQ ID NO: 27, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
    (q) a variant of the polypeptide of SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 positions;
    (r) a polypeptide comprising the polypeptide of (a), (b), (c), (d), (e), (f), (g), (h), (i), (j), (k), (l), (m), (n), (o), (p) or (q) and a N-terminal and/or C-terminal His-tag and/or HQ-tag;
    (s) a polypeptide comprising the polypeptide of (a), (b), (c), (d), (e), (f), (g), (h), (i), (j), (k), (l), (m), (n), (o), (p) or (q) and a N-terminal and/or C-terminal extension of between 1 and 10 amino acids; and
    (t) a fragment of the polypeptide of (a), (b), (c), (d), (e), (f), (g), (h), (i), (j), (k), (l), (m), (n), (o), (p) or (q) having lysozyme activity and having at least 90% of the length of the mature polypeptide.
26. The polypeptide of item 25, wherein the polypeptide comprises the motif F[I/L/V][A/S/K][H/N/S]GGGW (SEQ ID NO: 40).
27. The polypeptide of any of items 25 to 26, wherein the polypeptide comprises or consists of amino acids 1 to 207 of SEQ ID NO: 3, amino acids 1 to 216 of SEQ ID NO: 6, amino acids 1 to 204 of SEQ ID NO: 9, amino acids 1 to 203 of SEQ ID NO: 12, amino acids 1 to 204 of SEQ ID NO: 15, amino acids 1 to 208 of SEQ ID NO: 18, amino acids 1 to 207 of SEQ ID NO: 21, amino acids 1 to 207 of SEQ ID NO: 24, amino acids 1 to 216 of SEQ ID NO: 27, amino acids 1 to 217 of SEQ ID NO: 30, amino acids 1 to 207 of SEQ ID NO: 33 or amino acids 1 to 207 of SEQ ID NO: 38.
28. The polypeptide of any of items 25 to 27, wherein the significance is <0.05 as determined using Dunnett's test.
29. The polypeptide of any of items 25 to 28, wherein the activity is determined by measuring the decrease in optical density of a solution of resuspended *Micrococcus lysodeikticus* cells.
30. A composition comprising the polypeptide of any of items 25 to 29.
31. The composition of item 30 further comprising one or more formulating agents.
32. The composition of item 31 wherein the formulating agent comprises one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.
33. An animal feed additive comprising the lysozyme as disclosed in any of items 1 to 8, the granule of any of items 9 to 24, the polypeptide of any of items 25 to 29 or the composition of any of items 30 to 32.
34. The animal feed additive of item 33 further comprising one or more components selected from the list consisting of:
one or more vitamins;
one or more minerals;
one or more amino acids;
one or more prebiotics;
one or more organic acids; and
one or more other feed ingredients.
35. The animal feed additive of any of items 33 to 34 further comprising one or more additional enzymes.
36. The animal feed additive of item 35, wherein the one or more additional enzymes is selected from the group consisting of phytase, lysozyme, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.
37. The animal feed additive of any of items 33 to 36 further comprising one or more probiotics.
38. The animal feed additive of item 37, wherein the one or more probiotics is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.
39. The animal feed additive of any of items 33 to 38 further comprising one or more phytogenics.
40. The animal feed additive of item 39, wherein the phytogenic is selected from the group consisting of rosemary, sage, oregano, thyme, clove, lemongrass, essential oils, thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and *curcuma* extract or any combination thereof.
41. An animal feed comprising the lysozyme as disclosed in any of items 1 to 8, the granule of any of items 9 to 24, the polypeptide of any of items 25 to 29, the composition of any of items 30 to 32 or the animal feed additive of any of items 33 to 40 and plant based material.
42. The animal feed of item 41, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.
43. A pelleted animal feed comprising the lysozyme as disclosed in any of items 1 to 8, the granule of any of items 9 to 24, the polypeptide of any of items 25 to 29, the composition of any of items 30 to 32 or the animal feed additive of any of items 33 to 40 and plant based material.
44. The pelleted animal feed of item 43, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.
45. A method of improving one or more performance parameters of an animal comprising administering to one or more animals the lysozyme as disclosed in any of items 1 to 8, the granule of any of items 9 to 24, the polypeptide of any of items 25 to 29, the composition of any of items 30 to 32, the animal feed additive of any of items 33 to 40, the animal feed of any of items 41 to 42 or the pelleted animal feed of any of items 43 to 44.
46. The method of item 45, wherein improving the performance of an animal means improved body weight gain, improved European Production Efficiency Factor (EPEF) and/or improved FCR.
47. A method of preparing an animal feed comprising mixing the lysozyme as disclosed in any of items 1 to 8, the granule of any of items 9 to 24, the polypeptide of any of items 25 to 29, the composition of any of items 30 to 32 or the animal feed additive of any of items 33 to 40 with plant based material.
48. The method of item 47, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.

49. A method for improving the nutritional value of an animal feed, comprising adding to the feed the lysozyme as disclosed in any of items 1 to 8, the granule of any of items 9 to 24, the polypeptide of any of items 25 to 29, the composition of any of items 30 to 32 or the animal feed additive of any of items 33 to 40.

50. The method of item 49, wherein the feed is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.

51. A polynucleotide encoding the polypeptide of any of items 25 to 29.

52. A nucleic acid construct or expression vector comprising the polynucleotide of item 51 operably linked to one or more control sequences that direct the production of the polypeptide in an expression host.

53. A recombinant host cell comprising the polynucleotide of item 51 operably linked to one or more control sequences that direct the production of the polypeptide.

54. A method of producing the polypeptide of any of items 25 to 29, comprising:
    (a) cultivating a cell, which in its wild-type form produces the polypeptide, under conditions conductive for production of the polypeptide; and
    (b) recovering the polypeptide.

55. A method of producing the polypeptide of any of items 25 to 29, comprising:
    (a) cultivating a host cell of item 53 under conditions conducive for production of the polypeptide; and
    (b) recovering the polypeptide.

56. A transgenic plant, plant part or plant cell transformed with a polynucleotide encoding the polypeptide of any of items 25 to 29.

57. A whole broth formulation or cell culture composition comprising a polypeptide of any of items 25 to 29.

58. Use of the lysozyme as disclosed in any of items 1 to 8, the granule of any of items 9 to 24, the polypeptide of any of items 25 to 29, the composition of any of items 30 to 32 or the animal feed additive of any of items 33 to 40:
    in animal feed;
    in animal feed additives;
    in the preparation of a composition for use in animal feed;
    for improving the nutritional value of an animal feed; and/or
    for improving one or more performance parameters in an animal.

59. An isolated GH25 polypeptide having lysozyme activity selected from the group consisting of:
    (a) a polypeptide having at least 90% sequence identity to the polypeptide of SEQ ID NO: 3;
    (b) a polypeptide having at least 80% sequence identity to the polypeptide of SEQ ID NO: 6;
    (c) a polypeptide having at least 80% sequence identity to the polypeptide of SEQ ID NO: 9;
    (d) a polypeptide having at least 80% sequence identity to the polypeptide of SEQ ID NO: 12;
    (f) a polypeptide having at least 80% sequence identity to the polypeptide of SEQ ID NO: 18;
    (g) a polypeptide having at least 80% sequence identity to the polypeptide of SEQ ID NO: 21;
    (h) a polypeptide having at least 80% sequence identity to the polypeptide of SEQ ID NO: 24;
    (k) a polypeptide having at least 80% sequence identity to the polypeptide of SEQ ID NO: 33;
    (l) a polypeptide having at least 83% sequence identity to the polypeptide of SEQ ID NO: 38;
    (m) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33 and SEQ ID NO: 38, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
    (n) a polypeptide comprising the polypeptide of (a), (b), (c), (d), (e), (f), (g), (h), (i), (j), (k), (l) or (m) and a N-terminal and/or C-terminal His-tag and/or HQ-tag;
    (o) a polypeptide comprising the polypeptide of (a), (b), (c), (d), (e), (f), (g), (h), (i), (j), (k), (l) or (m) and a N-terminal and/or C-terminal extension of between 1 and 10 amino acids; and
    (p) a fragment of the polypeptide of (a), (b), (c), (d), (e), (f), (g), (h), (i), (j), (k), (l) or (m) having lysozyme activity and having at least 90% of the length of the mature polypeptide.

60. The polypeptide according to the invention having improved lysozyme activity a) compared to the lysozyme activity of hen eggwhite lysozyme (HEWL) or b) compared to the lysozyme activity of SEQ ID NO: 39 as determined by the Method for the Determination of Lysozyme Activity Against *Micrococcus lysodeikticus*.

61. The polypeptide according to the invention having improved lysozyme activity a) compared to the lysozyme activity of hen eggwhite lysozyme (HEWL) and b) compared to the lysozyme activity of SEQ ID NO: 39 as determined by any one of i) Method for the Determination of Lysozyme Activity Against *Micrococcus lysodeikticus* and ii) Method for the Determination of Lysozyme Activity Against *Lactobacillus johnsonii*.

62. A zootechnical additive for use in feed for poultry or swine, said additive comprising the polypeptide as defined by the invention.

63. A method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide as defined by the invention.

64. A method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 39.

65. A method of promoting the elimination of dead *Lactobacillus johnsonii* cells, or cell wall debris therefrom, from the digestive tract of an animal comprising feeding said animal a source of a polypeptide as defined by the invention.

66. A method of promoting the elimination of dead *Lactobacillus johnsonii* cells from the digestive tract of an animal comprising feeding said animal a source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 39.

67. The method according to any one of the embodiments wherein the polypeptide has a lysozyme activity against *Lactobacillus johnsonii* at 5 ppm that increases optical density (OD) measurement at 405 nm of at least 0.20 as determined by Method for the Determination of Lysozyme Activity Against *Lactobacillus johnsonii*.

The present invention is further described by the following examples that should not be construed as limiting the scope of the invention.

EXAMPLES

Strains

*Escherichia coli* Top-10 strain was purchased from Invitrogen (Life Technologies, Carlsbad, Calif., USA) and was used to propagate the expression vectors encoding for lysozyme polypeptides.

*Aspergillus oryzae* strain MT3568 was used for heterologous expression of the lysozyme polypeptide encoding sequences. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene.

*Aspergillus* nigerMBin118 is disclosed in WO 2004/090155.

The fungal strain NN000308 was purchased from Centraalbureau voor Schimmelcultures named as CBS174.70. The strain NN000308 was identified as *Myceliophthora fergusii* (previously identified as *Thielavia thermophila,—* syn. *Corynascus thermophilus*), based on both morphological characteristics and ITS rDNA sequence.

The fungal strain NN044232 was isolated from soil samples collected from China, in 1998 by the dilution plate method with PDA medium, pH7, 25 C. It was then purified by transferring a single conidium onto a PDA agar plate. The strain NN044232 was identified as *Penicillium* sp. 'qii', based on both morphological characteristics and ITS rDNA sequence.

The fungal strain NN058101 was isolated from soil samples collected from Guizhou Province, China, in 2014 by the dilution plate method with PDA medium pH3, 25 C. It was then purified by transferring a single conidium onto a PDA agar plate. The strain NN058101 was identified as *Paecilomyces* sp. XZ2658, based on both morphological characteristics and ITS rDNA sequence.

According to Yokoyama et at, IFO Res Commun 14, 118-142, 1989, the strain *Mortierella* alpine was isolated from soils in the Xinjiang Uighur autonomous region, China on or before 1989.

Strain *Purpureocillium lilacinum* NN070261 was isolated from a soil sample from the United States, and inoculated onto a PDA plate and incubated for 8 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Onygena equina* NN056731 was isolated on Gotland, Sweden. The strain was inoculated onto a PDA plate and incubated for 18 days at 20° C. in the darkness. Mycelia and spores from the plate were inoculated into 500 ml shake flasks containing 100 mls of YPG medium. The flasks were incubated for 18 days at 20° C. with shaking at 100 rpm.

The fungal strain NN054002 was isolated from soil samples collected from Tibet, China, in 2011 by the dilution plate method with PDA medium, 10 C. It was then purified by transferring a single conidium onto a PDA agar plate. The strain NN054002 was identified as *Lecanicillium* sp., based on both morphological characteristics and ITS rDNA sequence.

Strain *Penicillium atrovenetum* NN056836 was purchased from the Technical University of Denmark. The strain was inoculated onto a PDA plate and incubated for 5 days at 26° C. in the darkness. Mycelia and spores from the plate were inoculated into 500 ml shake flasks containing 100 mls of YPG medium. The flasks were incubated for 2 days at 26° C. with shaking at 100 rpm.

Strain *Malbranchea flava* CBS132.77 was purchased CBS-KNAW Fungal Biodiversity Centre, and inoculated onto a PDA plate and incubated for 14 days at 26° C. in the darkness. Mycelia and spores from the plate were inoculated into 500 ml shake flasks containing 100 mls of YPG medium. The flasks were incubated for 20 days at 26° C. with shaking at 100 rpm.

Strain *Engyodontium* album NN042720 was isolated in Denmark. The strain was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Media and Solutions

DAP4C-1 medium was composed of 0.5 g yeast extract, 10 g maltose, 20 g dextrose, 11 g magnesium sulphate heptahydrate, 1 g dipotassium phosphate, 2 g citric acid monohydrate, 5.2 g potassium phosphate tribasic monohydrate, 1 mL Dowfax 63N10 (antifoaming agent), 2.5 g calcium carbonate, supplemented with 1 mL KU6 metal solution, and deionised water to 1000 mL.

KU6 metal solution was composed of 6.8 g $ZnCl_2$, 2.5 g $CuSO_4.5H_2O$, 0.13 g $NiCl_2$, 13.9 g $FeSO_4.7H_2O$, 8.45 g $MnSO_4.H_2O$, 3 g $C_6H_3O_7.H_2O$, and deionised water to 1000 mL.

YP 2% glucose medium was composed of 10 g yeast extract, 20 g Bacto-peptone, 20 g glucose, and deionised water to 1000 mL.

LB plates were composed of 10 g of Bacto-tryptone, 5 g of yeast extract, 10 g of sodium chloride, 15 g of Bacto-agar, and deionised water to 1000 mL.

LB medium was composed of 10 g of Bacto-tryptone, 5 g of yeast extract, and 10 g of sodium chloride, and deionised water to 1000 mL.

COVE-Sucrose-T plates were composed of 342 g of sucrose, 20 g of agar powder, 20 mL of COVE salt solution, and deionised water to 1000 mL. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 µL/500 mL) were added.

COVE-N-Agar tubes were composed of 218 g Sorbitol, 10 g Dextrose, 2.02 g KNO$_3$, 25 g agar, 50 mL Cove salt solution, and deionised water up to 1000 mL.

COVE salt solution was composed of 26 g of MgSO$_4$.7H$_2$O, 26 g of KCL, 26 g of KH$_2$PO$_4$, 50 mL of COVE trace metal solution, and deionised water to 1000 mL.

COVE trace metal solution was composed of 0.04 g of Na$_2$B$_4$O$_7$.10H$_2$O, 0.4 g of CuSO$_4$.5H$_2$O, 1.2 g of FeSO$_4$.7H$_2$O, 0.7 g of MnSO$_4$.H$_2$O, 0.8 g of Na$_2$MoO$_4$.2H$_2$O, 10 g of ZnSO$_4$.7H$_2$O, and deionised water to 1000 mL.

YPM medium contained 1% of Yeast extract, 2% of Peptone and 2% of Maltose.

Example 1: Determination of Lysozyme Activity Against *Micrococcus lysodeikticus*

The activity of lysozyme was determined by measuring the decrease (drop) in absorbance/optical density of a solution of suspended *Micrococcus lysodeikticus* ATTC No. 4698 (Sigma-Aldrich M3770) measured in a microplate reader (Tecan Infinite M200) at 450 nm. The concentration of enzyme in the plate wells was 5 mg of protein/L.
Preparation of *Micrococcus lysodeikticus* Substrate Before use the cells were suspended in deionized water to a concentration of 10 mg cells/mL and the absorbance/optical density (OD) at 450 nm was measured. The cell suspension was then adjusted so that the cell concentration in the turbidity assay (180 µL buffer+20 µL sample+20 µL substrate) equaled an OD450=1 0.0. The adjusted cell suspension was then stored at ambient temperature before use. Suspended cells were used within 3 hours.
Preparation of Citric Acid-Phosphate Buffer pH 4

61.45 mL 0.1 M citric acid was mixed with 38.55 mL 0.2 M disodium hydrogen phosphate, and the pH was adjusted with hydrochloric acid or sodium hydroxide to pH 4.
Measurement of Lysozyme Antimicrobial Activity in the Turbidity Assay The lysozyme sample to be measured was diluted to a concentration of 50 mg enzyme protein/L in deionized water, and kept on ice until use. In a 96 well microtiter plate (Nunc) 180 µL citric acid-phosphate buffer pH 4 and 20 µL of the diluted lysozyme sample was added and kept cold (5° C.). To start the activity measurement 20 µL of the substrate (*Micrococcus lysodeikticus*) was added to each well, and kinetic measurement of absorbance at 450 nm was initiated for 1 hour at 37° C. in a microplate reader. The measured absorbance at 450 nm was monitored for each well and over time a drop in absorbance was seen if the lysozyme has lysozyme activity.

Following incubation, the lysozyme activity against *Micrococcus lysodeikticus* was determined as Δ absorbance at 450 nm (start value–end value) of each well after 1 hour. Significance was calculated using Dunnett's with control test p level 0.05 in JMP® version 12.1.0 statistical software package from SAS Institute Inc. SEQ ID NO: 39 was included in all experimental runs and compared to new candidates within each run to avoid influence of day to day variation.

Example 2: Genomic DNA Extraction from Strains of *Myceliophthora fergusii* and *Lecanicillium* sp

*Myceliophthora fergusii* strain was inoculated onto a PDA plate and incubated for 3 days at 45° C. in the darkness. Several mycelia-PDA plugs were inoculated into 500 ml shake flasks containing 100 ml of YPG medium. The flasks were incubated for 4 days at 45° C. with shaking at 160 rpm.

Strain *Penicillium* sp. 'qii' NN044232 was inoculated onto a PDA plate and incubated for 5 days at 25° C. in the darkness. Mycelia and spores from the plate were inoculated into 500 ml shake flasks containing 100 ml of YPG medium. The flasks were incubated for 4 days at 25° C. with shaking at 100 rpm.

Strain *Paecilomyces* sp. XZ2658 NN058101 was inoculated onto a PDA plate and incubated for 5 days at 25° C. in the darkness. Mycelia and spores from the plate were inoculated into 500 ml shake flasks containing 100 mls of YPG medium. The flasks were incubated for 5 days at 25° C. with shaking at 100 rpm.

Strain *Purpureocillium lilacinum* NN070261 was isolated from a soil sample from the United States, and inoculated onto a PDA plate and incubated for 8 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Onygena equina* NN056731 was inoculated onto a PDA plate and incubated for 18 days at 20° C. in the darkness. Mycelia and spores from the plate were inoculated into 500 ml shake flasks containing 100 mls of YPG medium. The flasks were incubated for 18 days at 20° C. with shaking at 100 rpm.

*Lecanicillium* sp. WMM742 was inoculated onto a PDA plate and incubated for 7 days at 15° C. in the darkness. Several mycelia-PDA plugs were inoculated into 500 ml shake flasks containing 100 ml of YPG medium. The flasks were incubated for 5 days at 20° C. with shaking at 160 rpm.

Strain *Penicillium atrovenetum* NN056836 was inoculated onto a PDA plate and incubated for 5 days at 26° C. in the darkness. Mycelia and spores from the plate were inoculated into 500 ml shake flasks containing 100 mls of YPG medium. The flasks were incubated for 2 days at 26° C. with shaking at 100 rpm.

Strain *Malbranchea flava* NN070411 was inoculated onto a PDA plate and incubated for 14 days at 26° C. in the darkness. Mycelia and spores from the plate were inoculated into 500 ml shake flasks containing 100 mls of YPG medium. The flasks were incubated for 20 days at 26° C. with shaking at 100 rpm.

Strain *Engyodontium album* NN042720 was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using a DNeasy® Plant Maxi Kit (QIAGEN GmbH, Hilden, Germany).

Example 3: Genome Sequencing, Assembly and Annotation of *Myceliophthora fergusii* (SEQ ID NO: 1)

The extracted genomic DNA sample of *Myceliophthora fergusii* to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene identification and functional prediction. GeneID (Parra et al., 2000, *Genome Research* 10(4):511-515) was used for gene prediction. Blastall version 2.2.10 (Altschul et al., 1990, *J. Mol. Biol.* 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The GH25 family lysozyme polypeptide, GH25_Myfer, was identified directly by analysis of the Blast results. The Agene program (Munch and Krogh, 2006, *BMC Bioinformatics* 7:263) and SignalP program (Nielsen et al., 1997, *Protein Engineering* 10: 1-6) were used to identify starting codons. The SignalP program was further used to predict signal peptides. Pepstats (Rice et al., 2000, *Trends Genet.* 16(6): 276-277) was used to predict isoelectric point of proteins, and molecular weight of the deduced amino acid sequences.

Example 4: Genome Sequencing, Assembly and Annotation of *Penicillium* sp. 'Qii' (SEQ ID NO: 4), *Paecilomyces* sp. XZ2658 (SEQ ID NO: 7 and 10), *Purpureocillium lilacinum* (SEQ ID NO: 16), *Onygena equina* (SEQ ID NO: 19), *Penicillium atrovenetum* (SEQ ID NO: 25), *Malbranchea flava* (SEQ ID NO: 28) and *Engyodontium* Album (SEQ ID NO: 31)

The extracted genomic DNA samples of *Penicillium* sp. 'qii', *Paecilomyces* sp. XZ2658, *Purpureocillium lilacinum*, *Onygena equina*, *Penicillium atrovenetum*, *Malbranchea flava* and *Engyodontium* album were genome sequenced using an ILLUMINA® HiSeq 2000 System (Illumina, Inc., San Diego, Calif., USA).

The raw reads of *Penicillium* sp. 'qii', *Paecilomyces* sp. XZ2658, *Penicillium atrovenetum* and *Malbranchea flava* were assembled using program Spades (Anton Bankevich et al., 2012, Journal of Computational Biology, 19(5): 455-477). The raw reads of *Purpureocillium lilacinum*, *Onygena equina*, and *Engyodontium* album were assembled using program Idba (Peng Yu et al., 2010, Research in Computational Molecular Biology. 6044:426-440. Springer Berlin Heidelberg). The assembled sequences were analyzed using standard bioinformatics methods for gene identification and function prediction. GeneMark-ES fungal version (Ter-Hovhannisyan V et al., 2008, Genome Research 18(12): 1979-1990) was used for gene prediction. Blastall version 2.2.10 (Altschul et al., 1990, Journal of Molecular Biology. 215(3): 403-410, ftp://ftp.ncbi.nlm.nih.gov/blast/executables/release/2.2.10/) and HMMER version 2.1.1 (National Center for Biotechnology Information (NCBI), Bethesda, Md., USA) were used to predict function based on structural homology. The GH25 family lysozyme polypeptides were identified directly by analysis of the Blast results. The Agene program (Munch and Krogh, 2006, BMC Bioinformatics 7: 263) and SignalP program (Nielsen et al., 1997, Protein Engineering 10: 1-6) were used to identify start codons. SignalP program was further used to predict signal peptides. Pepstats (Rice et al., 2000, Trends in Genetics. 16(6): 276-277) was used to predict isoelectric points and molecular weights.

Example 5: Genome Sequencing, Assembly and Annotation of *Mortierella alpina* (SEQ ID NO: 13)

Genomic DNA of *Mortierella alpina* was sequenced at Fasteris (Plan-les-Ouates, Switzerland) using an ILLUMINA® HiSeq 2000 System (Illumina, Inc., San Diego, Calif., USA). The assembled reads received from Fasteris, were analyzed using standard bioinformatics methods for gene identification and function prediction. GeneMark-ES fungal version (Ter-Hovhannisyan V et al., 2008, Genome Research 18(12): 1979-1990) was used for gene prediction. Blastall version 2.2.10 (Altschul et al., 1990, Journal of Molecular Biology. 215(3): 403-410, ftp://ftp.ncbi.nlm.nih.gov/blast/executables/release/2.2.10/) and HMMER version 2.1.1 (National Center for Biotechnology Information (NCBI), Bethesda, Md., USA) were used to predict function based on structural homology. The GH25 family lysozyme polypeptide was identified directly by analysis of the Blast results. The Agene program (Munch and Krogh, 2006, BMC Bioinformatics 7: 263) and SignalP program (Nielsen et al., 1997, Protein Engineering 10: 1-6) were used to identify start codons. SignalP program was further used to predict signal peptides. Pepstats (Rice et al., 2000, Trends in Genetics. 16(6): 276-277) was used to predict the isoelectric point and molecular weight.

Example 6: Genome Sequencing, Assembly and Annotation of *Lecanicillium* sp (SEQ ID NO: 22)

The extracted genomic DNA samples of *Lecanicillium* sp. was delivered to Fasteris (Switzerland) for genome sequencing using an ILLUMINA® HiSeq 2000 System (Illumina, Inc., San Diego, Calif., USA). The raw reads were assembled at Novozymes Denmark using program Idba (Peng, Yu et al., 2010, *Research in Computational Molecular Biology*, 6044:426-440. Springer Berlin Heidelberg). The assembled sequences were analyzed using standard bioinformatics methods for gene identification and function prediction. GeneMark-ES fungal version (Ter-Hovhannisyan V et al., 2008, *Genome Research* 18(12): 1979-1990) was used for gene prediction. Blastall version 2.2.10 (Altschul et al., 1990, *Journal of Molecular Biology*, 215(3): 403-410, ftp://ftp.ncbi.nlm.nih.gov/blast/executables/release/2.2.10/) and HMM ER version 2.1.1 (National Center for Biotechnology Information (NCBI), Bethesda, Md., USA) were used to predict function based on structural homology. The GH25 family lysozyme, GH25_Lecan2, was identified directly by analysis of the Blast results. The Agene program (Munch and Krogh, 2006, *BMC Bioinformatics*, 7:263) and SignalP program (Nielsen et al., 1997, *Protein Engineering*, 10: 1-6) were used to identify start codons. SignalP program was further used to predict signal peptides. Pepstats (Rice et al., 2000, *Trends Genet*, 16(6): 276-277) was used to predict isoelectric points and molecular weights.

Example 7: Cloning and Expression of GH25 Lysozymes (SEQ ID NO: 1 and 22)

Two fungal GH25 lysozyme wild type sequences (SEQ ID NO: 1 and 22) were cloned from *Myceliophthora fergusii* and *Lecanicillium* sp. respectively.

The fungal GH25 lysozymes were cloned into an *Aspergillus oryzae* expression vector pCaHj505 as described in WO2013029496. The transcription of the GH25 lysozyme coding sequence with the native secretion signal was under the control of an *Aspergillus oryzae* alpha-amylase gene promoter.

The final expression plasmids were individually transformed into an *Aspergillus oryzae* expression host. The GH25 lysozyme genes were integrated by homologous recombination into the *Aspergillus oryzae* host genome upon transformation. Four transformants of each transformation were selected from the selective media agar plate and inoculated to 3 ml of YPM medium in 24-well plate and incubated at 30° C., 150 rpm. After 3 days incubation, 20 µl of supernatant from each transformant were analyzed on NuPAGE Novex 4-12% Bis-Tris Gel w/MES according to the manufacturer's instructions. The resulting gel was stained with Instant Blue. SDS-PAGE profiles of the cultures showed that both genes were expressed with 1 protein band detected at 25KD. The recombinant *Aspergillus oryzae* strains with the strongest protein band were selected for shaking flask culturing and were inoculated on slant made of slant medium and incubated at 37C for 6-7 days. When strains were well grown to fully sporulated, they were inoculated to 2 L shaking flasks each containing 400 ml of YPM, 5-6 flasks for each strain. Flasks were shaking at 80 rpm, 30 C. Cultures were harvested on day 3 and filtered using a 0.45 µm DURAPORE Membrane and were purified as described in examples 13 and 14 respectively.

Example 8: PCR Amplification and InFusion Cloning of Lysozyme Encoding Sequences SEQ ID NO: 4, 7, 10 and 13

BamHI-XhoI based cloning from *Penicillium* sp. 'qii' (SEQ ID NO: 4), *Paecilomyces* sp. XZ2658 (SEQ ID NO: 7), *Aspergillus* sp. nov. XZ2609 (SEQ ID NO: 10) and *Mortierella* alpine (SEQ ID NO: 13).

The forward and reverse PCR primers shown in table 2 were used to generate an EcoRI-XhoI flanked cloning cassette from the genomic DNA prepared above for the following samples:

TABLE 2

PCR primers

| Primer* | Primer SEQ ID NO: | Primer to lysozyme SEQ ID NO: | Sequence |
|---|---|---|---|
| WIN1054-F | 44 | 4 | 5'-ACACAACTGGGGATCCACC ATGAAGACTACGGGTGTC |
| WIN1054-R | 45 | 4 | 5'-CCCTCTAGATCTCGAGTTA AGAACCCTTGGCAAAG |
| WIN1057-F | 46 | 7 | 5'-ACACAACTGGGGATCCACC ATGAAGTCTGTTGCTGTCT |
| WIN1057-R | 47 | 7 | 5'-CCCTCTAGATCTCGAGCTA AGAAGCATTCGCAATGC |
| WIN1058-F | 48 | 10 | 5'-ACACAACTGGGGATCCACC ATGAAGCTCACGAGTGTG |
| WIN1058-R | 49 | 10 | 5'-CCCTCTAGATCTCGAGTTA CGAACCTCTAGCAAGC |
| WIN1068-F | 50 | 13 | 5'-ACACAACTGGGGATCCACC ATGATCAGGGCAGTTGCT |
| WIN1068-R | 51 | 13 | 5'-CCCTCTAGATCTCGAGTCA GGAACCTTTAGCGAA |

*-F-forward primer; -R-reverse primer

Bold letters represent coding sequence. The underlined sequence is homologous to the insertion sites of pDau109.

The PCR reaction (25 µl) was composed of 12.5 µl of 2×IPROOF™ HF Master Mix, 0.5 µl of appropriate forward primer (100 µM), 0.5 µl of the appropriate reverse primer (100 µM), 0.5 µl of genomic (100 ng/µl), and 11 µl of deionized water. The PCR reaction was incubated in a DYAD® Dual-Block Thermal Cycler (MJ Research Inc., Waltham, Mass., USA) programmed for 1 cycle at 98° C. for 30 seconds; 30 cycles each at 98° C. for 10 seconds, 55° C. for 10 seconds, and 72° C. for 60 seconds; and 1 cycle at 72° C. for 10 minutes. Samples were cooled to 10° C. before removal and further processing.

Five µl of the PCR reaction were analyzed by 1% agarose gel electrophoresis using TAE buffer where an DNA band of the appropriate size was observed. In the case of WIN1054 for example, an approximately 700 base pair band was observed. The remaining PCR reactions were purified using an ILLUSTRA™ GFX™ PCR DNA and Gel Band Purification Kit according to the manufacturer's instructions.

The fragments were then cloned into BamHI and XhoI digested pDau109 using an IN-FUSION™ Cloning Kit resulting in plasmids containing the inserts. Cloning of the GH25 lysozyme PCR inserts into Bam HI-XhoI digested pDau109 resulted in the transcription of the cloned genes under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase. Isolated plasmids were sequenced with vector primers in order to determine a representative plasmid expression clone that was free of PCR errors.

Example 9: PCR Amplification and InFusion Cloning of Lysozyme Encoding Sequences SEQ ID NO: 16, 19, 25, 28 and 31

Based on the lysozyme gene sequences identified by genome mining in *Onygena equina*, *Purpureocillium lilacinum*, *Penicillium atrovenetum*, *Malbranchea flava* and *Engyodontium* album, InFusion cloning primers were designed and ordered (Sigma Aldrich, Darmstadt, Germany) (see list in table 3 below).

TABLE 3

InFusion cloning primers

| Primer* | Primer SEQ ID NO: | Primer to lysozyme SEQ ID NO: | Sequence |
|---|---|---|---|
| C8VRQ-F | 52 | 16 | ACACAACTGGGGATCCACCATGAAG TTCGCATCCGTCGCC |
| C8VRQ-R | 53 | 16 | AGATCTCGAGAAGCTTAACCGGCGT TGGCAATCTTCTT |
| C8VRJ-F | 54 | 19 | ACACAACTGGGGATCCACCATGTTG AAAACAATTATCTATACCACCCTTG CC |
| C8VRJ-R | 55 | 19 | AGATCTCGAGAAGCTTAGCCCTTTG CAAATCGTTGCAATCC |
| C8VRZ-F | 56 | 25 | ACACAACTGGGGATCCACCATGAAG ATCACTGCCTTCCCGCT |
| C8VRZ-R | 57 | 25 | AGATCTCGAGAAGCTTAAGCACCCT TGGCGAAGGTCT |
| C8VRT-F | 58 | 28 | ACACAACTGGGGATCCACCATGAAG CTGTCTCTCCTCCTTATTGTTGC |
| C8VRT-R | 59 | 28 | AGATCTCGAGAAGCTTAACCTAGGG CCATTCTCTTCAACCC |

TABLE 3-continued

InFusion cloning primers

| Primer* | Primer SEQ ID NO: | Primer to lysozyme SEQ ID NO: | Sequence |
|---|---|---|---|
| C8VS8-F | 60 | 31 | ACACAACTGGGGATCCACCATGAAG TCTTTTGGTGTTATTGCTACCGG |
| C8VS8-R | 61 | 31 | AGATCTCGAGAAGCTTAGCCTCTGG CGATTCTCTGAAGC |

*-F-forward primer; -R-reverse primer

PCR amplifications of SEQ ID NO: 16, 19, 25, 28 and 31 encoding for lysozyme polypeptides were carried out using Phusion High-Fidelity DNA polymerase (New England Biolabs, BioNordika Denmark A/S, Herlev, Denmark) in a 50 μL volume reaction. The PCR reaction mixes were consisting of 10 μL Phusion reaction buffer HF (5×); 1 μL of PCR nucleotide Mix (10 mM); 2 μL forward cloning primers (2.5 mM); 2 μL reverse cloning primers (2.5 mM); 1 μL Phusion High-Fidelity DNA Polymerase #M0530 L (2000 U/mL); and PCR grade water up to 50 μL. PCR reactions were incubated on a thermocycler T100 (Biorad, Hercules, Calif., USA) using the following program: initial denaturation of 2 min at 98° C. followed by 30 cycles of 10 sec at 98° C., 2 min at 72° C. and ending up by a final elongation of 10 min at 72° C. PCR amplicons were purified using AMPure XP beads system kit (Agencourt, Beverly, Mass., USA) adapted on a Biomek FXp Liquid handler (Beckman Coulter, Brea, Calif., USA).

InFusion cloning was made using InFusion HD Plus EcoDry Cloning system kit (Takara, Kusatsu, Japan) in expression vector pDAu109 (WO 2005042735) previously digested with BamHI and HindIII restriction enzymes and following manufacturer's instructions.

A 2.5 μL volume of the five time diluted ligation mixtures was used to transform E. coli TOP10 (see strain chapter) chemically competent cells (Life Technologies, Carlsbad, Calif., USA). Three colonies were selected from LB agar plates containing 100 μg of ampicillin per ml and cultivated overnight in 3 mL of LB medium supplemented with 100 μg of ampicillin per ml. Plasmids DNA were purified using a Qiagen Spin Miniprep kit (Cat. 27106) (QIAGEN GmbH, Hilden, Germany) according to the manufacturer's instructions.

Lysozyme sequences cloned by InFusion were scrutinized for errors by Sanger DNA sequencing.

Forward and reverse oligonucleotide primers shown below were designed to PCR amplify the GH25 open reading frame from the genomic DNA samples. An IN-FUSION™ Cloning Kit (Clontech, Mountain View, Calif., USA) was used to clone the fragment directly into the expression vector pDau109 (WO 2005/042735).

Example 10: PCR Amplification and Cloning of Lysozyme Encoding Sequence SEQ ID NO: 34

The genomic sequence SEQ ID NO: 34 contains seven introns and eight exons. In order to facilitate expression in Aspergillus oryzae, an intronless version of the gene which was codon optimized was created (sequence SEQ ID NO: 36). The synthetic gene SEQ ID NO: 36 was ordered from GeneArt (Thermofisher Scientific) as a BamHI-HindIII flanked open reading frame and cloned directly into the pDau109 vector as described in Example 8.

Example 11: Expression of GH25 Lysozymes in Aspergillus oryzae (SEQ ID NO: 4, 7, 10, 13 and 36)

Protoplasts of Aspergillus oryzae MT3568 were prepared according to WO 95/002043. One hundred μl of protoplasts were mixed with 1-3 μg of one of the following Aspergillus expression vectors: SEQ ID NO: 4, 7, 10, 13 or 36.

Six ul containing about 3.0 μg total DNA was used for the transformation. The DNA was gently added to 100 μl of A. oryzae MT3568 protoplasts and 250 μl of 60% PEG 4000 (Sigma-Aldrich cat. No. 95904). The 60% (W/V) PEG 4000 was prepared in the following manner: PEG 4000 powder was dissolved in double distilled $H_2O$ and then heated for 10-20 seconds in a microwave oven at 800 watt until dissolved. The dissolved solution was cooled down to room temperature and then adjusted with $CaCl_2$) solution and Tris-HCl solution (pH 7.5) for a final concentration of 10 mM of each. After adding the 60% PEG 4000 solution, the tube was gently mixed and incubated at 37° C. for 30 minutes. The mix was added to 6 ml of top agar with 10 mM acetamide and plated onto COVE-sorbitol plates with 10 mM acetamide.

The plates were incubated at 37° C. for 3 or more days and then moved to 26° C. for two days. Spores from 4 to 8 individual colonies were picked by first dipping a white 10 μl inoculation pin (Nunc A/S, Denmark) in a 0.1% TWEEN® 80 solution, contacting the sporulating colony on the selection plate, and restreaking with the pin onto fresh COVE sorbitol plates containing 10 mM acetamide. After 5 days at 26° C., spores from the restreaked colonies were used to inoculate a 96 well deep dish plate (NUNC, cat. no. 260251, Thermoscientific, USA). The wells of the deep dish plate contained 500 uls of either YP+2% glucose or DAP4C media. The inoculated plate was sealed with gas permeable tape (89009-656, VWR.com). Plates were incubated stationary at 30 C for 5 days. Expression was verified by analysis of 20 uls of harvested culture fluid on SDS-PAGE using a NUPAGE® 10% Bis-Tris gel (Invitrogen, Carlsbad, Calif., USA) and Coomassie blue staining. One transformant for each transformation experiment was selected for further work.

Spores of each designated transformant were inoculated into both YP+2% glucose medium and DAP-4C-1 medium (100 mls in 500 ml Erlenmeyer shake flask with baffles). The cultures were incubated at 26° C. and 150 rpm, 3 days and if necessary 4 days. An SDS gel was run as above to test protein amount.

After incubation for 4-7 days at 37° C. spores of four transformants were inoculated into 0.2 mL of YP+2% glucose or DAP4C-1 medium in 96 well microtiter plates. After 4 days cultivation at 30° C., the culture broths were analysed by SDS-PAGE to identify transformants producing the highest amounts of lysozyme enzymes.

The culture broths for SEQ ID NO: 4, 7, 10, 13 and 36 were purified as described in Example 15.

Example 12: Preparation and Expression of Aspergillus Protoplasts (SEQ ID NO: 16, 19, 25, 28 and 31)

Protoplasts of Aspergillus oryzae MT3568 were prepared according to WO 95/002043. One hundred μl of protoplasts were mixed with 1-3 μg of the Aspergillus expression vectors or OE PCRs (for SEQ ID NO: 16, 19, 25, 28 and 31) and 250 μL of 60% PEG 4000 (Applichem, Darmstadt, Germany) (polyethylene glycol, molecular weight 4,000), 10 mM CaCl$_2$, and 10 mM Tris-HCl pH 7.5 and gently mixed. The mixtures were incubated at 37° C. for 30 minutes and the protoplasts were spread onto COVE plates for selection. After incubation for 4-7 days at 37° C. spores of four transformants were inoculated into 0.2 mL of YP+2% glucose or DAP4C-1 medium in 96 well microtiter plates. After 4 days cultivation at 30° C., the culture broths were analysed by SDS-PAGE to identify transformants producing the highest amounts of lysozyme enzymes.

Spores of the best transformants for each transformation were spread onto COVE plates containing 0.01% TRITON® X-100 in order to isolate single colonies. The spreading was repeated twice in total on COVE plates containing 10 mM sodium nitrate. Spores were then inoculated into 500 mL shake flasks containing 100 mL of YP+2% glucose and incubated for 4 days at 30° C. with shaking at 100 rpm.

Previously selected strains were inoculated in 250 mL shake flasks with baffle containing 100 to 150 mL of DAP4C-1 supplemented lactic acid and with diammonium phosphate or YP2% glucose medium and fermented during 4 days at a temperature of 30° C. under 150 rpm agitation. Culture broths were harvested by filtration using a 0.2 μm filter device. The culture broths can be purified as described in Example 15.

Example 13: Purification of the GH25 Lysozyme from *Myceliophthora fergusii* (SEQ ID NO: 3)

The culture supernatant was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then the elution fractions and flow-through fraction were collected to detect lysozyme activity. The fractions with lysozyme activity were analyzed by SDS-PAGE, and then concentrated for further evaluation. The protein concentration was determined by Qubit® Protein Assay Kit (Invitrogen, cat Q33212).

Example 14: Purification of the GH25 Lysozyme from *Lecanicillium* sp. WMM742 (SEQ ID NO: 24)

The culture supernatant was firstly precipitated with ammonium sulfate (80% saturation), then the precipitation was added water to adjust conductance to about 160 mS/cm. The solution was filtered with 0.45 um filter and then loaded into Phenyl Sepharose 6 Fast Flow column (GE Healthcare) equilibrated with 20 mM NaAc at pH4.5 with 1.5M (NH4)2SO4 added. A gradient decrease of (NH4)2SO4 concentration was applied as elution buffer from 1.8M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH4.5 for further evaluation. The protein concentration was determined by Qubit® Protein Assay Kit (Invitrogen, cat Q33212).

Example 15: Purification of GH25 Lysozymes

General Purification Procedure

The fermentation supernatant with the lysozyme was filtered through a Fast PES Bottle top filter with a 0.22 μm cut-off. pH was adjusted to 4.5 with 10% acetic acid. After the pH-adjustment the solution became a little cloudy and this was removed by filtration through a Fast PES Bottle top filter with a 0.22 μm cut-off.

After pretreatment about 650 ml of the lysozyme containing solution was purified by chromatography on SP Sepharose, approximately 50 ml in a XK26 column, using as buffer A 50 mM Na-acetate pH 4.5, and as buffer B 50 mM Na-acetate+1 M NaCl pH 4.5. The fractions from the column were pooled based on the chromatogram (absorption at 280 and 254 nm) and SDS-PAGE analysis. The pooled fractions were buffer-changed into 50 mM Na-acetate, pH 5.5 and concentrated using Amicon spin filters with a 10 kDa cut-off.

Purification of SEQ ID NO: 6, 9, 12 and 15

The fermentation broth biomass was separated by centrifugation. The sample filtration was then carried out by tangential flow filtration using hollow fiber 0.2μ cartridges mounted on a QuixStand® system and then loaded into a Hydrophobic column (TOYOPEARL® Phenyl-650M) equilibrated with 50 mM HEPES pH 8+1.5M Ammonium Sulphate at pH8.0. Step gradient decrease of ammonium sulphate concentration was applied as elution buffer from 1.5M to zero. The pooled elution peak fractions, wash and flow-through were collected and analysed on SDS gel. The peak with lysozyme band on gel was then buffer exchanged by 50 mM HEPES pH 8 and the protein concentration was determined by spectrophotometer (Agilent 8453 UV-visible Spectroscopy System).

The molecular weight was estimated from SDS-PAGE and the purity was >90%.

Purification of SEQ ID NO: 18, 21, 27, 30, 33 and 38

The fermentation supernatant with the lysozyme was filtered through a Fast PES Bottle top filter with a 0.22 μm cut-off.

Pretreatment of the filtered broth may be necessary if the expression level is low and/or conductivity is high (in general >10 S/m). Pretreatment can be performed using ultrafiltration on a 3-5 kDa cutoff membrane, buffer exchange on a G25 gel filtration column or dialysis. SEQ ID NO: 38 was pretreated using a G25 gel filtration column using 50 mM acetate pH4.5 whilst SEQ ID NO: 18 and 21 were pretreated in a dialysis membrane (6-8 KDa) overnight in 50 mM scetate 4.5.

pH was adjusted to 4.5. If the solution became cloudy after the pH-adjustment, this was removed by filtration through a Fast PES Bottle top filter with a 0.22 μm cut-off. The lysozyme containing solution was purified by chromatography on SP Sepharose, approximately 50 ml in a XK26 column, using as buffer A 50 mM Na-acetate pH 4.5, and as buffer B 50 mM Na-acetate+1 M NaCl pH 4.5 using a 0-100% gradient over ca. 10CV. The fractions from the column were pooled based on the chromatogram (absorption at 280 and 254 nm) and SDS-PAGE analysis.

The molecular weight was estimated from SDS-PAGE and the purity was >90%.

Example 16: Determination of Lysozyme Activity

Method for the Determination of Lysozyme Activity Against *Micrococcus lysodeikticus*.

The activity of lysozyme was determined by measuring the decrease (drop) in absorbance/optical density of a solution of suspended *Micrococcus lysodeikticus* ATTC No. 4698 (Sigma-Aldrich M3770) measured in a microplate reader (Tecan Infinite M200) at 450 nm as described in example 1, using a concentration of enzyme in the plate wells of 5 mg of protein/L. Significance was calculated using Dunnett's with control test p level 0.05 in JMP® version 12.1.0 statistical software package from SAS Institute Inc. SEQ ID NO: 39 was included in all experimental runs and compared to new candidates within each run to avoid influence of day to day variation.

The results of the lysozymes of the application are presented in tables 4 to 9 below.

TABLE 4

OD Drop of SEQ ID NO: 3

| Lysozyme | Average ΔOD drop | St. dev. | P-value |
| --- | --- | --- | --- |
| SEQ ID NO: 3 | 0.248 | 0.009 | 0.004 |
| SEQ ID NO: 39 | 0.148 | 0.013 | 1.000 |

TABLE 5

OD Drop of SEQ ID NO: 6, 9, 12 and 15

| Lysozyme | Average ΔOD drop | St. dev. | P-value |
| --- | --- | --- | --- |
| SEQ ID NO: 6 | 0.287 | 0.024 | <0.001 |
| SEQ ID NO: 9 | 0.263 | 0.007 | 0.005 |
| SEQ ID NO: 12 | 0.257 | 0.013 | 0.008 |
| SEQ ID NO: 15 | 0.253 | 0.040 | 0.013 |
| SEQ ID NO: 39 | 0.183 | 0.010 | 1.000 |

TABLE 6

OD Drop of SEQ ID NO: 18 and 21

| Lysozyme | Average ΔOD drop | St. dev. | P-value |
| --- | --- | --- | --- |
| SEQ ID NO: 18 | 0.244 | 0.029 | 0.023 |
| SEQ ID NO: 21 | 0.239 | 0.054 | 0.034 |
| SEQ ID NO: 39 | 0.188 | 0.010 | 1.000 |

TABLE 7

OD Drop of SEQ ID NO: 24

| Lysozyme | Average ΔOD drop | St. dev. | P-value |
| --- | --- | --- | --- |
| SEQ ID NO: 24 | 0.235 | 0.022 | 0.021 |
| SEQ ID NO: 39 | 0.181 | 0.005 | 1.000 |

TABLE 8

OD Drop of SEQ ID NO: 27, 30 and 33

| Lysozyme | Average ΔOD drop | St. dev. | P-value |
| --- | --- | --- | --- |
| SEQ ID NO: 27 | 0.290 | 0.024 | <0.001 |
| SEQ ID NO: 30 | 0.281 | 0.037 | <0.001 |
| SEQ ID NO: 33 | 0.244 | 0.004 | 0.044 |
| SEQ ID NO: 39 | 0.205 | 0.021 | 1.000 |

TABLE 9

OD Drop of SEQ ID NO: 38

| Lysozyme | Average ΔOD drop | St. dev. | P-value |
| --- | --- | --- | --- |
| SEQ ID NO: 38 | 0.264 | 0.026 | 0.030 |
| SEQ ID NO: 39 | 0.216 | 0.039 | 1.000 |

The results show that all of the lysozymes of the invention have significantly increased activity (p<0.05) compared to this prior art lysozyme as determined using the OD drop method.

TABLE 10

Average OD drop

| Lysozyme | Average ΔOD drop |
| --- | --- |
| Average for Hen Egg White Lysozyme | 0.180 |
| Average for SEQ ID NO: 39 | 0.187 |

Example 17: Method for the Determination of Lysozyme Activity Against *Lactobacillus johnsonii*

Pgn Extraction:
Cultivation of *Lactobacillus johnsonii*:
Materials
　MRS broth, product number BD 288130, pH 6.3-6.7.
　MRS agar plates, BD 288130; Agar Oxoid LP0011; pH 6.3-6.7.
　0.9% NaCl, Merck 106404, Cas no. 7647145
　jars, supplier Merck 116387, Anaerocult anaerobic jar 2.5 L
　Anaerogen 2.5 L, ThermoScientific, catalogue no. AN0025A *Lactobacillus johnsonii*, DSM10533
Procedure
　*L. johnsonii* was streaked from freeze stock to MRS agar plate and incubated under anaerobic conditions for 2 days, anaerobic jar with Anaerogen 2.5 L, 30° C. Some colonies were inoculated into 500 mL MRS broth in a 500 mL blue cap bottle and placed in an anaerobic jar with Anaerogen 2.5 L for 72 hours at 30° C.

The culture was spun down (6000 rpm, 10 minutes) and the supernatant was poured off before another round of centrifugation was performed. The pellet was washed in 100 mlL 0.9% NaCl and the suspension was mixed well and centrifuged at 6000 rpm for 10 minutes. The supernatant was poured off and the washing procedure in 0.9% NaCl was repeated to a total of three washes. Approximately 40 mL 0.9% NaCl was added to the pellet and the solution was transferred to a 50 mL falcon tube. The solution was centrifuged at 6000 rpm for 10 minutes and the supernatant was poured off. The pellet was stored at −18° C. until the extraction of the peptidoglycan was conducted.

Extraction Procedure:
Materials
　Protease from *Streptomyces griseus*, Sigma-Aldrich P5147, CAS 9036-06-0
　PBS pH 7.3:
NaCl: 8 g, Sigma-Aldrich 31434, CAS 7647-14-5
KCl: 0.2 g, Sigma-Aldrich P9333, CAS 7447-40-7
$KH_2PO_4$: 0.24 g, Sigma-Aldrich P5655, CAS 7778-77-0
$Na_2HPO_4$. 2 $H_2O$: 1.44 g, Sigma-Aldrich 30412, CAS 10028-24-7
Add Milli-Q water to 1000 mL
　1% Triton-X 100 solution:
1 mL Triton X100, Sigma-Aldrich X100, CAS 9002-93-1
Add Milli Q water to 100 mL
　500 mM sodium carbonate buffer, pH 9.3:
500 mM sodium carbonate is made from 21 g $Na_2CO_3$ (Sigma-Aldrich S7795, CAS 497-19-8) in
500 mL MQ water 500 mM sodium bicarbonate is made from 72 g NaHCO$_3$ (Sigma-Aldrich S6014, CAS 144-55-8) in 500 mL MW water The pH 9.3 buffer is made from 320 mL NaHCO$_3$ and 80 mL Na$_2$CO$_3$ and adjusting pH with HCl Phenol solution with 10 mM Tris HCl, pH 8.0, 1 mM EDTA, Sigma-Aldrich P4557, CAS 108-95-2

Acetone, Sigma-Aldrich 32201-M, CAS 67-64-1

Ethanol, 96%, CCS Healthcare 1680643, CAS 64-17-5

Procedure

L. johnsonii cell material was freeze dried. The freeze dried material (525 mg) was suspended in PBS (40 mL) in a 50 mL Falcon tube. The suspension was shaken for 2 h @ 700 rpm in a thermoshaker at room temperature. Streptomyces griseus protease (55 mg) was then added and the suspension was incubated 6 h @ 37 C in the thermoshaker. It was then centrifuged 20 min @ 1900 g at room temperature, and the supernatant was decanted. The pellet was re-suspended in 1% Triton X-100 (40 mL) and shaken overnight @ 37 C. After another centrifugation and decantation, the pellet was re-suspended in PBS (40 mL) and protease (55 mg) added again. The suspension was again incubated 6 h @ 37 C, centrifuged and decanted. The pellet was re-suspended in PBS (40 mL) and shaken overnight @ 37 C. This washing procedure was repeated once more with PBS (40 mL, 30 min agitation), then with 50% ethanol/water (40 mL, 30 min agitation). The pellet was then split into two Falcon tubes. To each tube was added phenol solution (15 mL) pre-heated to 40 C. The suspensions were shaken 10 min @ 40 C, and then added 96% ethanol (25 mL to each tube), centrifuged and decanted. The pellets were further washed with acetone (40 mL in each tube) and 96% ethanol (40 mL in each tube), before being freeze dried. Combining the pellets from the two tubes yielded 80 mg purified peptidoglycan as a white powder.

Reducing End Assay

The lysozyme was diluted in phosphate dilution buffer (5 mM citrate, 5 mM K$_2$HPO$_4$, 0.01% TritonX-100, pH 5.0) to 50 µg/mL in polypropylene tubes. The diluted lysozyme was further diluted in a 96-well polypropylene microtiter plate by preparing a two-fold dilution series down to a concentration of 6.25 µg/mL in phosphate dilution buffer (5 mM citrate, 5 mM K$_2$HPO$_4$, 0.01% TritonX-100, pH 5.0). A 50 mg/ml stock solution of L. johnsonii substrate in MillQ was prepared and diluted in phosphate buffer (50 mM citrate, 50 mM K$_2$HPO$_4$, pH 5.0) to 250 µg/ml. In a polypropylene deepwell plate 50 µL of the lysozyme dilution was mixed with 450 µL L. johnsonii solution and incubated at 40° C. with shaking (500 rpm) for 45 min. After incubation, the deepwell plate was centrifuged (3200 rpm, 7 min) to pellet insoluble material and 100 µL of the supernatant was mixed with 50 µL 3.2M HCl in a 96-well PCR plate and incubated at 95° C. for 80 min. 50 µL of 3.5 M NaOH was added to each well of the PCR plate, and 150 µL of each sample was transferred to a new PCR plate containing 75 µL/well 4-hydroxybenzhydrazide (PAHBAH) solution in K-Na tartrate/NaOH buffer (50 g/L K-Na tartrate+20 g/L NaOH). The plate was incubated at 95° C. for 10 min before 100 µL/sample was transferred to a clear flat-bottomed microtiter plate for optical density (OD) measurement at 405 nm. OD measurements were performed on three times diluted samples (50 µL sample diluted in 100 µL in Milli-Q water). The OD measurement values represent the difference after the original (background) reading was subtracted and represent the average of two OD measurement values. Results are shown in Table 11 and in FIG. 1.

TABLE 11

Average OD405 measurements (background corrected) in Reducing End Assay

| Lysozyme | Concentration of lysozyme in µg/mL | | | |
|---|---|---|---|---|
| | 5 | 2.5 | 1.25 | 0.63 |
| SEQ ID NO: 3 | 0.51 | 0.30 | 0.22 | 0.12 |
| SEQ ID NO: 9 | 0.43 | 0.24 | 0.15 | 0.08 |
| SEQ ID NO: 6 | 0.49 | 0.31 | 0.20 | 0.10 |
| SEQ ID NO: 12 | 0.33 | 0.13 | 0.11 | 0.04 |
| SEQ ID NO: 15 | 0.04 | 0.01 | 0.00 | 0.00 |
| SEQ ID NO: 21 | 0.62 | 0.42 | 0.24 | 0.16 |
| SEQ ID NO: 24 | 0.22 | 0.15 | 0.08 | 0.03 |
| SEQ ID NO: 27 | 0.05 | 0.02 | 0.01 | 0.00 |
| SEQ ID NO: 30 | 0.20 | 0.12 | 0.06 | 0.03 |
| SEQ ID NO: 33 | 0.86 | 0.55 | 0.37 | 0.32 |
| SEQ ID NO: 18 | 0.32 | 0.18 | 0.14 | 0.11 |
| SEQ ID NO: 38 | 0.34 | 0.24 | 0.14 | 0.14 |
| SEQ ID NO: 39 | 0.88 | 0.73 | 0.46 | 0.31 |
| HEWL | 0.00 | −0.01 | 0.00 | −0.02 |

Example 18: Animal Feed and Animal Feed Additives Comprising a Lysozyme of the Invention Animal Feed Additive A formulation of a lysozyme of the invention (e.g. SEQ ID NO: 3, 6, 9, 12, 15, 18, 21, 24, 27, 30, 33, 38 or 39) containing 0.01 g to 10 g enzyme protein is added to the following premix (per kilo of premix):

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |
| 25 | % | Sodium |

Animal Feed

This is an example of an animal feed (broiler feed) comprising the animal feed additive as described above:

62.55% Maize 33.8% Soybean meal (50% crude protein)

1.0% Soybean oil 0.2% DL-Methionine 0.22% DCP (dicalcium phosphate)

0.76% CaCO$_3$ (calcium carbonate)

0.32% Sand 0.15% NaCl (sodium chloride)

1% of the above Premix

The ingredients are mixed, and the feed is pelleted at the desired temperature, e.g. 60, 65, 75, 80, 85, 90 or even 95° C.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A recombinant host cell comprising a polynucleotide encoding a polypeptide of Glycoside Hydrolase Family 25 (GH25) having lysozyme activity and at least 90% sequence identity to the polypeptide of SEQ ID NO: 3 operably linked to one or more control sequences that direct the production of the polypeptide.

2. The recombinant host cell of claim 1, wherein the GH25 polypeptide has at least 95% sequence identity to the polypeptide of SEQ ID NO: 3.

3. The recombinant host cell of claim 1, wherein the GH25 polypeptide has at least 97% sequence identity to the polypeptide of SEQ ID NO: 3.

4. The recombinant host cell of claim 1, wherein the GH25 polypeptide has at least 99% sequence identity to the polypeptide of SEQ ID NO: 3.

5. A method of producing a polypeptide having lysozyme activity, comprising:
   (a) cultivating the recombinant host cell of claim 1 under conditions conducive for production of the polypeptide; and
   (b) recovering the polypeptide.

6. The method of claim 5, wherein the GH25 polypeptide has at least 95% sequence identity to the polypeptide of SEQ ID NO: 3.

7. The method of claim 5, wherein the GH25 polypeptide has at least 97% sequence identity to the polypeptide of SEQ ID NO: 3.

8. The method of claim 5, wherein the GH25 polypeptide has at least 99% sequence identity to the polypeptide of SEQ ID NO: 3.

9. The method of claim 5, wherein the GH25 polypeptide comprises the amino acid sequence of SEQ ID NO: 3.

10. The method of claim 5, wherein the GH25 polypeptide is a fragment of SEQ ID NO:
    3, wherein the fragment has at least 90% of the length of SEQ ID NO: 3 and has lysozyme activity.

11. The method of claim 5, wherein the GH25 polypeptide has an N-terminal and/or C-terminal His-tag and/or His-Gln-tag.

12. The method of claim 5, wherein the GH25 polypeptide has an N-terminal and/or C-terminal extension of between 1 and 10 amino acids.

13. The method of claim 5, wherein the host cell is a Gram-positive or Gram-negative bacterium selected from the group consisting of *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

14. The method of claim 13, wherein host cell may is a *Bacillus* cell selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

15. The method of claim 5, wherein the host cell is a filamentous fungal cell selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cells.

16. The method of claim 6, wherein the host cell is a Gram-positive or Gram-negative bacterium selected from the group consisting of *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

17. The method of claim 16, wherein host cell may is a *Bacillus* cell selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

18. The method of claim 6, wherein the host cell is a filamentous fungal cell selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cells.

\* \* \* \* \*

UNITED STATES PATENT AND TRADEMARK OFFICE
CERTIFICATE OF CORRECTION

PATENT NO. : 10,986,850 B2
APPLICATION NO. : 16/463205
DATED : April 27, 2021
INVENTOR(S) : Klausen et al.

Page 1 of 2

It is certified that error appears in the above-identified patent and that said Letters Patent is hereby corrected as shown below:

In the Claims

Please amend Claims 13, 14, 16 and 17 as follows:

Column 169, Line 44:
13. The method of claim 5, wherein the host cell is a Gram-positive or Gram-negative bacterium selected from the group consisting of *Bacillus, Clostridium, Enterococcus, Geobacillus, Lactobacillus, Lactococcus, Oceanobacillus, Staphylococcus, Streptococcus, Streptomyces, Campylobacter, E. coli, Flavobacterium, Fusobacterium, Helicobacter, Ilyobacter, Neisseria, Pseudomonas, Salmonella*, and *Ureaplasma*.

Column 170, Line 4:
14. The method of claim 13, wherein host cell is a *Bacillus* cell selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

Column 170, Line 22:
16. The method of claim 15 wherein the host cell is a Gram-positive or Gram-negative bacterium selected from the group consisting of *Bacillus, Clostridium, Enterococcus, Geobacillus, Lactobacillus, Lactococcus, Oceanobacillus, Staphylococcus, Streptococcus, Streptomyces, Campylobacter, E. coli, Flavobacterium, Fusobacterium, Helicobacter, Ilyobacter, Neisseria, Pseudomonas, Salmonella*, and *Ureaplasma*.

Column 170, Line 31:
17. The method of claim 16 wherein host cell is a *Bacillus* cell selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus*

Signed and Sealed this
Third Day of August, 2021

Drew Hirshfeld
*Performing the Functions and Duties of the
Under Secretary of Commerce for Intellectual Property and
Director of the United States Patent and Trademark Office*

*megaterium, Bacillus pumilus, Bacillus stearothermophilus, Bacillus subtilis*, and *Bacillus thuringiensis* cells.

```
                           SEQUENCE LISTING

<160> NUMBER OF SEQ ID NOS: 61

<210> SEQ ID NO 1
<211> LENGTH: 909
<212> TYPE: DNA
<213> ORGANISM: Myceliophthora fergusii
<220> FEATURE:
<221> NAME/KEY: CDS
<222> LOCATION: (1)..(144)
<220> FEATURE:
<221> NAME/KEY: sig_peptide
<222> LOCATION: (1)..(54)
<220> FEATURE:
<221> NAME/KEY: mat_peptide
<222> LOCATION: (55)..(906)
<220> FEATURE:
<221> NAME/KEY: CDS
<222> LOCATION: (376)..(906)

<400> SEQUENCE: 1 atg aaa gct gct ctc ctc gct acc gtc tcc gcc ctc gcg gcc ggc gtg     48
Met Lys Ala Ala Leu Leu Ala Thr Val Ser Ala Leu Ala Ala Gly Val
        -15                 -10                  -5 caa gcc gcc gtc caa ggc ttt gac att tcc cac tgg cag tcc agc gtg     96
Gln Ala Ala Val Gln Gly Phe Asp Ile Ser His Trp Gln Ser Ser Val
    -1  1               5                  10 gac ttt aag gcg gcc tac aac tcg ggc gcc cgc ttc gtc atc atc aag    144
Asp Phe Lys Ala Ala Tyr Asn Ser Gly Ala Arg Phe Val Ile Ile Lys
15                 20                  25                  30 gtaggtatta aggcctctct gtcgagcgag gcggcgtgtt tcaaccatca ttggattctc    204
ctgccttaaa tttgctccct ctgtccaaag aggaggaaag aggaggggag aataacggaa    264
gatgcataat gggcaaaaaa aaaagaaaaa ccaagaaaaa aaaaacactg ggaactactg    324
atgaatagtc tcgtgagaga gccgacgtgc taaccccaac acctctatta g gcg acc    381
                                                         Ala Thr gag ggc acg tcg ttc atc gac ccc aag ttc tcg tcg cac tac acg ggc    429
Glu Gly Thr Ser Phe Ile Asp Pro Lys Phe Ser Ser His Tyr Thr Gly
        35                  40                  45 gcg acc aac gcc ggc ttc atc cgg ggc gcg tac cac ttc gcg cac ccg    477
Ala Thr Asn Ala Gly Phe Ile Arg Gly Ala Tyr His Phe Ala His Pro
    50                  55                  60 ggc cag tcg tcg ggc gag gcg cag gcc gac tac ttc ctc gcg cac ggc    525
Gly Gln Ser Ser Gly Glu Ala Gln Ala Asp Tyr Phe Leu Ala His Gly
65                  70                  75                  80 ggc ggc tgg acg ccc gac ggc atc acg ctg ccc ggc atg ctg gac ctc    573
Gly Gly Trp Thr Pro Asp Gly Ile Thr Leu Pro Gly Met Leu Asp Leu
                85                  90                  95 gag gcc tac aac gcg ggc gag tgc tgg ggc ctg tcc cag agc gcc atg    621
Glu Ala Tyr Asn Ala Gly Glu Cys Trp Gly Leu Ser Gln Ser Ala Met
            100                 105                 110 gtc gcg tgg atc aag gcc ttc agc gac cgc tac cac gcc cgc acc ggc    669
Val Ala Trp Ile Lys Ala Phe Ser Asp Arg Tyr His Ala Arg Thr Gly
        115                 120                 125 gtg tac ccg atg ctc tac acc aac ctg tcg tgg tgg aag acc tgc acc    717
Val Tyr Pro Met Leu Tyr Thr Asn Leu Ser Trp Trp Lys Thr Cys Thr
    130                 135                 140 ggc aac tcc aag gcc ttc gtc aac acc aac ccg ctc gtc ctc gcc cgc    765
Gly Asn Ser Lys Ala Phe Val Asn Thr Asn Pro Leu Val Leu Ala Arg
```

```
                145                 150                 155                 160
tgg gcc agc tcg ccc ggc gag atc ccc ggc ggc tgg ccg tgg cag acc      813
Trp Ala Ser Ser Pro Gly Glu Ile Pro Gly Gly Trp Pro Trp Gln Thr
                165                 170                 175 atc tgg cag aac tcg gac tcg tac cgc tac ggc ggc gac tcg gac atc      861
Ile Trp Gln Asn Ser Asp Ser Tyr Arg Tyr Gly Gly Asp Ser Asp Ile
        180                 185                 190 ttc aac ggc gac atg aac cag ctc agg agg ctg gcc acc gcc gcc taa      909
Phe Asn Gly Asp Met Asn Gln Leu Arg Arg Leu Ala Thr Ala Ala
        195                 200                 205

<210> SEQ ID NO 2
<211> LENGTH: 225
<212> TYPE: PRT
<213> ORGANISM: Myceliophthora fergusii

<400> SEQUENCE: 2

Met Lys Ala Ala Leu Leu Ala Thr Val Ser Ala Leu Ala Ala Gly Val
                -15                 -10                  -5

Gln Ala Ala Val Gln Gly Phe Asp Ile Ser His Trp Gln Ser Ser Val
 -1   1               5                  10

Asp Phe Lys Ala Ala Tyr Asn Ser Gly Ala Arg Phe Val Ile Ile Lys
 15                  20                  25                  30

Ala Thr Glu Gly Thr Ser Phe Ile Asp Pro Lys Phe Ser Ser His Tyr
                 35                  40                  45

Thr Gly Ala Thr Asn Ala Gly Phe Ile Arg Gly Ala Tyr His Phe Ala
             50                  55                  60

His Pro Gly Gln Ser Ser Gly Glu Ala Gln Ala Asp Tyr Phe Leu Ala
         65                  70                  75

His Gly Gly Gly Trp Thr Pro Asp Gly Ile Thr Leu Pro Gly Met Leu
 80                  85                  90

Asp Leu Glu Ala Tyr Asn Ala Gly Glu Cys Trp Gly Leu Ser Gln Ser
 95                 100                 105                 110

Ala Met Val Ala Trp Ile Lys Ala Phe Ser Asp Arg Tyr His Ala Arg
                115                 120                 125

Thr Gly Val Tyr Pro Met Leu Tyr Thr Asn Leu Ser Trp Trp Lys Thr
                130                 135                 140

Cys Thr Gly Asn Ser Lys Ala Phe Val Asn Thr Asn Pro Leu Val Leu
            145                 150                 155

Ala Arg Trp Ala Ser Ser Pro Gly Glu Ile Pro Gly Gly Trp Pro Trp
        160                 165                 170

Gln Thr Ile Trp Gln Asn Ser Asp Ser Tyr Arg Tyr Gly Gly Asp Ser
175                 180                 185                 190

Asp Ile Phe Asn Gly Asp Met Asn Gln Leu Arg Arg Leu Ala Thr Ala
                195                 200                 205

Ala

<210> SEQ ID NO 3
<211> LENGTH: 207
<212> TYPE: PRT
<213> ORGANISM: Myceliophthora fergusii
<220> FEATURE:
<221> NAME/KEY: mat_peptide
<222> LOCATION: (1)..(207)

<400> SEQUENCE: 3

Ala Val Gln Gly Phe Asp Ile Ser His Trp Gln Ser Ser Val Asp Phe
 1                   5                  10                  15
```

```
Lys Ala Ala Tyr Asn Ser Gly Ala Arg Phe Val Ile Ile Lys Ala Thr
             20                  25                  30

Glu Gly Thr Ser Phe Ile Asp Pro Lys Phe Ser Ser His Tyr Thr Gly
         35                  40                  45

Ala Thr Asn Ala Gly Phe Ile Arg Gly Ala Tyr His Phe Ala His Pro
 50                  55                  60

Gly Gln Ser Ser Gly Glu Ala Gln Ala Asp Tyr Phe Leu Ala His Gly
 65                  70                  75                  80

Gly Gly Trp Thr Pro Asp Gly Ile Thr Leu Pro Gly Met Leu Asp Leu
             85                  90                  95

Glu Ala Tyr Asn Ala Gly Glu Cys Trp Gly Leu Ser Gln Ser Ala Met
            100                 105                 110

Val Ala Trp Ile Lys Ala Phe Ser Asp Arg Tyr His Ala Arg Thr Gly
            115                 120                 125

Val Tyr Pro Met Leu Tyr Thr Asn Leu Ser Trp Trp Lys Thr Cys Thr
130                 135                 140

Gly Asn Ser Lys Ala Phe Val Asn Thr Asn Pro Leu Val Leu Ala Arg
145                 150                 155                 160

Trp Ala Ser Ser Pro Gly Glu Ile Pro Gly Trp Pro Trp Gln Thr
            165                 170                 175

Ile Trp Gln Asn Ser Asp Ser Tyr Arg Tyr Gly Gly Asp Ser Asp Ile
            180                 185                 190

Phe Asn Gly Asp Met Asn Gln Leu Arg Arg Leu Ala Thr Ala Ala
            195                 200                 205

<210> SEQ ID NO 4
<211> LENGTH: 761
<212> TYPE: DNA
<213> ORGANISM: Penicillium sp. 'qii'
<220> FEATURE:
<221> NAME/KEY: CDS
<222> LOCATION: (1)..(165)
<220> FEATURE:
<221> NAME/KEY: sig_peptide
<222> LOCATION: (1)..(51)
<220> FEATURE:
<221> NAME/KEY: mat_peptide
<222> LOCATION: (52)..(758)
<220> FEATURE:
<221> NAME/KEY: CDS
<222> LOCATION: (225)..(758)

<400> SEQUENCE: 4 atg aag act acg ggt gtc tct ctt ctg ctt gca gca ggt act gcc tac    48
Met Lys Thr Thr Gly Val Ser Leu Leu Leu Ala Ala Gly Thr Ala Tyr
    -15                 -10                  -5 gca tcg aca atc cag cct cgg gca agc ggc gtc cag gga ttc gat atc    96
Ala Ser Thr Ile Gln Pro Arg Ala Ser Gly Val Gln Gly Phe Asp Ile
 -1  1               5                  10                  15 tca agc tac caa ggc acc gtc aac ttt gcc ggc gcc tac gga gcc ggt   144
Ser Ser Tyr Gln Gly Thr Val Asn Phe Ala Gly Ala Tyr Gly Ala Gly
             20                  25                  30 gca cga ttc gtc atg atc aag gtgagcctcg gcataaactt gtgaccggcg      195
Ala Arg Phe Val Met Ile Lys
             35 agttgtttgg actaactgaa acgcgctag gcg act gaa ggc acc acc tac ata   248
                                Ala Thr Glu Gly Thr Thr Tyr Ile
                                            40                  45 gat tcc acc ttc tcc agc cac tat gac ggt gct acc agc gcc ggc ttg   296
Asp Ser Thr Phe Ser Ser His Tyr Asp Gly Ala Thr Ser Ala Gly Leu
```

```
                    50                  55                  60
atc cgc ggg gct tac cac ttc gcc cac ccg gac tcc agc tct ggc gct      344
Ile Arg Gly Ala Tyr His Phe Ala His Pro Asp Ser Ser Ser Gly Ala
        65                  70                  75 acc cag gcc gag tac ttc ctg gct cac gga ggt ggc tgg acc aac gat      392
Thr Gln Ala Glu Tyr Phe Leu Ala His Gly Gly Gly Trp Thr Asn Asp
80                  85                  90 ggc atc acc ttg ccc ggc atg ctg gac atc gaa tac aac ccc tcg ggc      440
Gly Ile Thr Leu Pro Gly Met Leu Asp Ile Glu Tyr Asn Pro Ser Gly
95                  100                 105                 110 tct acc tgc tac ggt ctg agt gct tcc gcc atg gtc tcc tgg atc aag      488
Ser Thr Cys Tyr Gly Leu Ser Ala Ser Ala Met Val Ser Trp Ile Lys
            115                 120                 125 gac ttc gga gag acc tac aac agc aag act ggt cgg tac cct atg atc      536
Asp Phe Gly Glu Thr Tyr Asn Ser Lys Thr Gly Arg Tyr Pro Met Ile
        130                 135                 140 tac agc acg gcc gat tgg tgg agc acc tgc aca gga gac agc aca tcc      584
Tyr Ser Thr Ala Asp Trp Trp Ser Thr Cys Thr Gly Asp Ser Thr Ser
    145                 150                 155 ttc agt agt gac tac cct ctg gtg ctt gct cag tat gct agc tcc att      632
Phe Ser Ser Asp Tyr Pro Leu Val Leu Ala Gln Tyr Ala Ser Ser Ile
160                 165                 170 agc acc gtc ccc gga ggc tgg cct tac cag agc ttc tgg cag aac gcg      680
Ser Thr Val Pro Gly Gly Trp Pro Tyr Gln Ser Phe Trp Gln Asn Ala
175                 180                 185                 190 gac tca tac agc tat ggc ggt gat tct gat ctg tgg aat ggt agc gag      728
Asp Ser Tyr Ser Tyr Gly Gly Asp Ser Asp Leu Trp Asn Gly Ser Glu
            195                 200                 205 gac tct ctg aag acc ttt gcc aag ggt tct taa                          761
Asp Ser Leu Lys Thr Phe Ala Lys Gly Ser
        210                 215
```

<210> SEQ ID NO 5
<211> LENGTH: 233
<212> TYPE: PRT
<213> ORGANISM: Penicillium sp. 'qii'

<400> SEQUENCE: 5

```
Met Lys Thr Thr Gly Val Ser Leu Leu Leu Ala Ala Gly Thr Ala Tyr
        -15                 -10                  -5

Ala Ser Thr Ile Gln Pro Arg Ala Ser Gly Val Gln Gly Phe Asp Ile
-1   1               5                  10                  15

Ser Ser Tyr Gln Gly Thr Val Asn Phe Ala Gly Ala Tyr Gly Ala Gly
                20                  25                  30

Ala Arg Phe Val Met Ile Lys Ala Thr Glu Gly Thr Thr Tyr Ile Asp
            35                  40                  45

Ser Thr Phe Ser Ser His Tyr Asp Gly Ala Thr Ser Ala Gly Leu Ile
        50                  55                  60

Arg Gly Ala Tyr His Phe Ala His Pro Asp Ser Ser Gly Ala Thr
    65                  70                  75

Gln Ala Glu Tyr Phe Leu Ala His Gly Gly Gly Trp Thr Asn Asp Gly
80                  85                  90                  95

Ile Thr Leu Pro Gly Met Leu Asp Ile Glu Tyr Asn Pro Ser Gly Ser
                100                 105                 110

Thr Cys Tyr Gly Leu Ser Ala Ser Ala Met Val Ser Trp Ile Lys Asp
            115                 120                 125

Phe Gly Glu Thr Tyr Asn Ser Lys Thr Gly Arg Tyr Pro Met Ile Tyr
        130                 135                 140
```

Ser Thr Ala Asp Trp Trp Ser Thr Cys Thr Gly Asp Ser Thr Ser Phe
            145                 150                 155

Ser Ser Asp Tyr Pro Leu Val Leu Ala Gln Tyr Ala Ser Ser Ile Ser
160                 165                 170                 175

Thr Val Pro Gly Gly Trp Pro Tyr Gln Ser Phe Trp Gln Asn Ala Asp
                180                 185                 190

Ser Tyr Ser Tyr Gly Gly Asp Ser Asp Leu Trp Asn Gly Ser Glu Asp
            195                 200                 205

Ser Leu Lys Thr Phe Ala Lys Gly Ser
            210                 215

<210> SEQ ID NO 6
<211> LENGTH: 216
<212> TYPE: PRT
<213> ORGANISM: Penicillium sp. 'qii'
<220> FEATURE:
<221> NAME/KEY: mat_peptide
<222> LOCATION: (1)..(216)

<400> SEQUENCE: 6

Ser Thr Ile Gln Pro Arg Ala Ser Gly Val Gln Gly Phe Asp Ile Ser
1               5                   10                  15

Ser Tyr Gln Gly Thr Val Asn Phe Ala Gly Ala Tyr Gly Ala Gly Ala
            20                  25                  30

Arg Phe Val Met Ile Lys Ala Thr Glu Gly Thr Thr Tyr Ile Asp Ser
        35                  40                  45

Thr Phe Ser Ser His Tyr Asp Gly Ala Thr Ser Ala Gly Leu Ile Arg
50                  55                  60

Gly Ala Tyr His Phe Ala His Pro Asp Ser Ser Ser Gly Ala Thr Gln
65                  70                  75                  80

Ala Glu Tyr Phe Leu Ala His Gly Gly Gly Trp Thr Asn Asp Gly Ile
                85                  90                  95

Thr Leu Pro Gly Met Leu Asp Ile Glu Tyr Asn Pro Ser Gly Ser Thr
            100                 105                 110

Cys Tyr Gly Leu Ser Ala Ser Ala Met Val Ser Trp Ile Lys Asp Phe
        115                 120                 125

Gly Glu Thr Tyr Asn Ser Lys Thr Gly Arg Tyr Pro Met Ile Tyr Ser
130                 135                 140

Thr Ala Asp Trp Trp Ser Thr Cys Thr Gly Asp Ser Thr Ser Phe Ser
145                 150                 155                 160

Ser Asp Tyr Pro Leu Val Leu Ala Gln Tyr Ala Ser Ser Ile Ser Thr
            165                 170                 175

Val Pro Gly Gly Trp Pro Tyr Gln Ser Phe Trp Gln Asn Ala Asp Ser
        180                 185                 190

Tyr Ser Tyr Gly Gly Asp Ser Asp Leu Trp Asn Gly Ser Glu Asp Ser
            195                 200                 205

Leu Lys Thr Phe Ala Lys Gly Ser
            210                 215

<210> SEQ ID NO 7
<211> LENGTH: 747
<212> TYPE: DNA
<213> ORGANISM: Paecilomyces sp. XZ2658
<220> FEATURE:
<221> NAME/KEY: CDS
<222> LOCATION: (1)..(135)
<220> FEATURE:
<221> NAME/KEY: sig_peptide

```
<222> LOCATION: (1)..(57)
<220> FEATURE:
<221> NAME/KEY: mat_peptide
<222> LOCATION: (58)..(744)
<220> FEATURE:
<221> NAME/KEY: CDS
<222> LOCATION: (211)..(744)

<400> SEQUENCE: 7 atg aag tct gtt gct gtc ttt gcc ggt ctg gcc tcc atg gtc agc att        48
Met Lys Ser Val Ala Val Phe Ala Gly Leu Ala Ser Met Val Ser Ile
        -15                 -10                  -5 gcc aca gcc acc gtt gca ggc ttc gat att tcc aac tac caa cct tcg        96
Ala Thr Ala Thr Val Ala Gly Phe Asp Ile Ser Asn Tyr Gln Pro Ser
         -1   1               5                  10 gtc aac ttt gca aaa gca tac gcg gac ggt gca cgc ttc gtcattatca        145
Val Asn Phe Ala Lys Ala Tyr Ala Asp Gly Ala Arg Phe
        15                  20                  25 aggcaagcag gccagaccag cgcctgccag ctcaaacaag accagattgc taactctctt    205 ctcag gcc acc gaa ggc acc acc tac atc gac ccc agt ttc agc tcc cat    255
      Ala Thr Glu Gly Thr Thr Tyr Ile Asp Pro Ser Phe Ser Ser His
              30                  35                  40 tac acc ggg gcc act aac gcc ggt ctc atc cgc gga ggc tac cat ttt       303
Tyr Thr Gly Ala Thr Asn Ala Gly Leu Ile Arg Gly Gly Tyr His Phe
            45                  50                  55 gcc cat ccg gga tcc agc acc ggc gcc gct cag gcc acc tac ttc ctt       351
Ala His Pro Gly Ser Ser Thr Gly Ala Ala Gln Ala Thr Tyr Phe Leu
        60                  65                  70 gcc cac ggc ggc ggc tgg tcc aag gac ggc atc acg ctc cct ggc atg       399
Ala His Gly Gly Gly Trp Ser Lys Asp Gly Ile Thr Leu Pro Gly Met
    75                  80                  85 atc gac ctc gag tac aac ccc agt ggc gcg acc tgc tat ggc ctc tcg       447
Ile Asp Leu Glu Tyr Asn Pro Ser Gly Ala Thr Cys Tyr Gly Leu Ser
 90                  95                 100                 105 acc agc gcc atg gtc agc tgg atc tcc gac ttt gtc gag acg tac cac       495
Thr Ser Ala Met Val Ser Trp Ile Ser Asp Phe Val Glu Thr Tyr His
                110                 115                 120 agc aag acg ggc gtc tac ccg ctc att tat acc tcg aca agc tgg tgg       543
Ser Lys Thr Gly Val Tyr Pro Leu Ile Tyr Thr Ser Thr Ser Trp Trp
            125                 130                 135 aac cag tgt acc ggc agc agc acc gcc ttt gcc agc aag tgt cct ctt       591
Asn Gln Cys Thr Gly Ser Ser Thr Ala Phe Ala Ser Lys Cys Pro Leu
        140                 145                 150 gtg gtt gct cgc tac gcc agc agc gtt ggc act ctt cct gcc ggt tgg       639
Val Val Ala Arg Tyr Ala Ser Ser Val Gly Thr Leu Pro Ala Gly Trp
    155                 160                 165 ggc tac cag acc atc tgg cag aat agc gat agc tcg ccc tgg ggc ggt       687
Gly Tyr Gln Thr Ile Trp Gln Asn Ser Asp Ser Ser Pro Trp Gly Gly
170                 175                 180                 185 gac aat gat att ttc aac ggc agt ctg gac cag ctc aag cgc att gcg       735
Asp Asn Asp Ile Phe Asn Gly Ser Leu Asp Gln Leu Lys Arg Ile Ala
                190                 195                 200 aat gct tct tag                                                       747
Asn Ala Ser <210> SEQ ID NO 8
<211> LENGTH: 223
<212> TYPE: PRT
<213> ORGANISM: Paecilomyces sp. XZ2658

<400> SEQUENCE: 8
```

Met Lys Ser Val Ala Val Phe Ala Gly Leu Ala Ser Met Val Ser Ile
            -15                 -10                  -5

Ala Thr Ala Thr Val Ala Gly Phe Asp Ile Ser Asn Tyr Gln Pro Ser
         -1   1              5                  10

Val Asn Phe Ala Lys Ala Tyr Ala Asp Gly Ala Arg Phe Ala Thr Glu
 15               20                  25

Gly Thr Thr Tyr Ile Asp Pro Ser Phe Ser Ser His Tyr Thr Gly Ala
 30               35                  40                  45

Thr Asn Ala Gly Leu Ile Arg Gly Gly Tyr His Phe Ala His Pro Gly
              50                  55                  60

Ser Ser Thr Gly Ala Ala Gln Ala Thr Tyr Phe Leu Ala His Gly Gly
              65                  70                  75

Gly Trp Ser Lys Asp Gly Ile Thr Leu Pro Gly Met Ile Asp Leu Glu
              80                  85                  90

Tyr Asn Pro Ser Gly Ala Thr Cys Tyr Gly Leu Ser Thr Ser Ala Met
             95                  100                 105

Val Ser Trp Ile Ser Asp Phe Val Glu Thr Tyr His Ser Lys Thr Gly
110                 115                 120                 125

Val Tyr Pro Leu Ile Tyr Thr Ser Thr Ser Trp Trp Asn Gln Cys Thr
                130                 135                 140

Gly Ser Ser Thr Ala Phe Ala Ser Lys Cys Pro Leu Val Val Ala Arg
                145                 150                 155

Tyr Ala Ser Ser Val Gly Thr Leu Pro Ala Gly Trp Gly Tyr Gln Thr
                160                 165                 170

Ile Trp Gln Asn Ser Asp Ser Ser Pro Trp Gly Asp Asn Asp Ile
175                 180                 185

Phe Asn Gly Ser Leu Asp Gln Leu Lys Arg Ile Ala Asn Ala Ser
190                 195                 200

<210> SEQ ID NO 9
<211> LENGTH: 204
<212> TYPE: PRT
<213> ORGANISM: Paecilomyces sp. XZ2658
<220> FEATURE:
<221> NAME/KEY: mat_peptide
<222> LOCATION: (1)..(204)

<400> SEQUENCE: 9

Thr Val Ala Gly Phe Asp Ile Ser Asn Tyr Gln Pro Ser Val Asn Phe
 1               5                   10                  15

Ala Lys Ala Tyr Ala Asp Gly Ala Arg Phe Ala Thr Glu Gly Thr Thr
             20                  25                  30

Tyr Ile Asp Pro Ser Phe Ser Ser His Tyr Thr Gly Ala Thr Asn Ala
         35                  40                  45

Gly Leu Ile Arg Gly Gly Tyr His Phe Ala His Pro Gly Ser Ser Thr
     50                  55                  60

Gly Ala Ala Gln Ala Thr Tyr Phe Leu Ala His Gly Gly Gly Trp Ser
65                  70                  75                  80

Lys Asp Gly Ile Thr Leu Pro Gly Met Ile Asp Leu Glu Tyr Asn Pro
             85                  90                  95

Ser Gly Ala Thr Cys Tyr Gly Leu Ser Thr Ser Ala Met Val Ser Trp
            100                 105                 110

Ile Ser Asp Phe Val Glu Thr Tyr His Ser Lys Thr Gly Val Tyr Pro
        115                 120                 125

Leu Ile Tyr Thr Ser Thr Ser Trp Trp Asn Gln Cys Thr Gly Ser Ser
    130                 135                 140

```
            Thr Ala Phe Ala Ser Lys Cys Pro Leu Val Val Ala Arg Tyr Ala Ser
            145                 150                 155                 160

Ser Val Gly Thr Leu Pro Ala Gly Trp Gly Tyr Gln Thr Ile Trp Gln
                            165                 170                 175

Asn Ser Asp Ser Ser Pro Trp Gly Gly Asp Asn Asp Ile Phe Asn Gly
                        180                 185                 190

Ser Leu Asp Gln Leu Lys Arg Ile Ala Asn Ala Ser
                    195                 200

<210> SEQ ID NO 10
<211> LENGTH: 669
<212> TYPE: DNA
<213> ORGANISM: Paecilomyces sp. XZ2658
<220> FEATURE:
<221> NAME/KEY: CDS
<222> LOCATION: (1)..(666)
<220> FEATURE:
<221> NAME/KEY: sig_peptide
<222> LOCATION: (1)..(57)
<220> FEATURE:
<221> NAME/KEY: mat_peptide
<222> LOCATION: (58)..(666)

<400> SEQUENCE: 10 atg aag ctc acg agt gtg ttg acc ctg gtt ggc tgt gcc gtc aca ggc      48
Met Lys Leu Thr Ser Val Leu Thr Leu Val Gly Cys Ala Val Thr Gly
            -15                 -10                  -5 aca tct gcc gcc gtg caa gga cac gac gtc agc cat tgg cag ggt aac      96
Thr Ser Ala Ala Val Gln Gly His Asp Val Ser His Trp Gln Gly Asn
        -1  1               5                  10 atc aac tgg ggc gcg gtc aag gca gcc ggc gtc aag ttt aca tac att     144
Ile Asn Trp Gly Ala Val Lys Ala Ala Gly Val Lys Phe Thr Tyr Ile
            15                  20                  25 aaa gca aca gag tca acc aac tac atc gac ccc agc ttc aac gca aat     192
Lys Ala Thr Glu Ser Thr Asn Tyr Ile Asp Pro Ser Phe Asn Ala Asn
 30                 35                  40                  45 tat gtc ggc gcc acc aat acc gga ctg ata cgc ggc gca tac cac ttt     240
Tyr Val Gly Ala Thr Asn Thr Gly Leu Ile Arg Gly Ala Tyr His Phe
                50                  55                  60 gcc cgg cca ggg gat tca tca ggt gcc gcg cag gca aat tat ttt gtc     288
Ala Arg Pro Gly Asp Ser Ser Gly Ala Ala Gln Ala Asn Tyr Phe Val
            65                  70                  75 agc cat ggt ggt ggg tgg tcc gca gac ggg aga act ttg cct ggc gct     336
Ser His Gly Gly Gly Trp Ser Ala Asp Gly Arg Thr Leu Pro Gly Ala
        80                  85                  90 ctt gat ctt gag gcg ggc tgt agc gga ttg tcg caa tca gca atg acg     384
Leu Asp Leu Glu Ala Gly Cys Ser Gly Leu Ser Gln Ser Ala Met Thr
 95                 100                 105 gcc tgg atc cgg gac ttc agc aac acc tat cac gcg cgg act ggt cgg     432
Ala Trp Ile Arg Asp Phe Ser Asn Thr Tyr His Ala Arg Thr Gly Arg
110                 115                 120                 125 ttc ccc gtc att tac aca act acc agc tgg tgg aag act tgc acc ggc     480
Phe Pro Val Ile Tyr Thr Thr Thr Ser Trp Trp Lys Thr Cys Thr Gly
                130                 135                 140 aat gcg tcc gga ttt cag aac gac cat ccg ctt tgg att gcg cga tgg     528
Asn Ala Ser Gly Phe Gln Asn Asp His Pro Leu Trp Ile Ala Arg Trp
            145                 150                 155 ggc cct tca cct ggg gag ttg ccg gca gga tat ggc ttt cac acc ttt     576
Gly Pro Ser Pro Gly Glu Leu Pro Ala Gly Tyr Gly Phe His Thr Phe
        160                 165                 170 tgg cag tat gcg gac aag gga cct ctt cca ggc gac cag gac aac ttt     624
Trp Gln Tyr Ala Asp Lys Gly Pro Leu Pro Gly Asp Gln Asp Asn Phe
```

-continued

```
Trp Gln Tyr Ala Asp Lys Gly Pro Leu Pro Gly Asp Gln Asp Asn Phe
    175                 180                 185 aat ggc gat gag gcc ggt ctt gca agg ctt gct aga ggt tcg taa              669
Asn Gly Asp Glu Ala Gly Leu Ala Arg Leu Ala Arg Gly Ser
    190                 195                 200

<210> SEQ ID NO 11
<211> LENGTH: 222
<212> TYPE: PRT
<213> ORGANISM: Paecilomyces sp. XZ2658

<400> SEQUENCE: 11

Met Lys Leu Thr Ser Val Leu Thr Leu Val Gly Cys Ala Val Thr Gly
                -15                 -10                  -5

Thr Ser Ala Ala Val Gln Gly His Asp Val Ser His Trp Gln Gly Asn
         -1   1               5                  10

Ile Asn Trp Gly Ala Val Lys Ala Ala Gly Val Lys Phe Thr Tyr Ile
 15                  20                  25

Lys Ala Thr Glu Ser Thr Asn Tyr Ile Asp Pro Ser Phe Asn Ala Asn
 30                  35                  40                  45

Tyr Val Gly Ala Thr Asn Thr Gly Leu Ile Arg Gly Ala Tyr His Phe
                 50                  55                  60

Ala Arg Pro Gly Asp Ser Ser Gly Ala Ala Gln Ala Asn Tyr Phe Val
             65                  70                  75

Ser His Gly Gly Gly Trp Ser Ala Asp Gly Arg Thr Leu Pro Gly Ala
         80                  85                  90

Leu Asp Leu Glu Ala Gly Cys Ser Gly Leu Ser Gln Ser Ala Met Thr
 95                 100                 105

Ala Trp Ile Arg Asp Phe Ser Asn Thr Tyr His Ala Arg Thr Gly Arg
110                 115                 120                 125

Phe Pro Val Ile Tyr Thr Thr Thr Ser Trp Trp Lys Thr Cys Thr Gly
                130                 135                 140

Asn Ala Ser Gly Phe Gln Asn Asp His Pro Leu Trp Ile Ala Arg Trp
            145                 150                 155

Gly Pro Ser Pro Gly Glu Leu Pro Ala Gly Tyr Gly Phe His Thr Phe
        160                 165                 170

Trp Gln Tyr Ala Asp Lys Gly Pro Leu Pro Gly Asp Gln Asp Asn Phe
    175                 180                 185

Asn Gly Asp Glu Ala Gly Leu Ala Arg Leu Ala Arg Gly Ser
190                 195                 200

<210> SEQ ID NO 12
<211> LENGTH: 203
<212> TYPE: PRT
<213> ORGANISM: Paecilomyces sp. XZ2658
<220> FEATURE:
<221> NAME/KEY: mat_peptide
<222> LOCATION: (1)..(203)

<400> SEQUENCE: 12

Ala Val Gln Gly His Asp Val Ser His Trp Gln Gly Asn Ile Asn Trp
 1               5                  10                  15

Gly Ala Val Lys Ala Ala Gly Val Lys Phe Thr Tyr Ile Lys Ala Thr
                 20                  25                  30

Glu Ser Thr Asn Tyr Ile Asp Pro Ser Phe Asn Ala Asn Tyr Val Gly
             35                  40                  45

Ala Thr Asn Thr Gly Leu Ile Arg Gly Ala Tyr His Phe Ala Arg Pro
         50                  55                  60
```

```
Gly Asp Ser Ser Gly Ala Ala Gln Ala Asn Tyr Phe Val Ser His Gly
 65                  70                  75                  80

Gly Gly Trp Ser Ala Asp Gly Arg Thr Leu Pro Gly Ala Leu Asp Leu
                 85                  90                  95

Glu Ala Gly Cys Ser Gly Leu Ser Gln Ser Ala Met Thr Ala Trp Ile
            100                 105                 110

Arg Asp Phe Ser Asn Thr Tyr His Ala Arg Thr Gly Arg Phe Pro Val
        115                 120                 125

Ile Tyr Thr Thr Thr Ser Trp Trp Lys Thr Cys Thr Gly Asn Ala Ser
130                 135                 140

Gly Phe Gln Asn Asp His Pro Leu Trp Ile Ala Arg Trp Gly Pro Ser
145                 150                 155                 160

Pro Gly Glu Leu Pro Ala Gly Tyr Gly Phe His Thr Phe Trp Gln Tyr
                165                 170                 175

Ala Asp Lys Gly Pro Leu Pro Gly Asp Gln Asp Asn Phe Asn Gly Asp
            180                 185                 190

Glu Ala Gly Leu Ala Arg Leu Ala Arg Gly Ser
        195                 200
```

```
<210> SEQ ID NO 13
<211> LENGTH: 663
<212> TYPE: DNA
<213> ORGANISM: Mortierella alpina
<220> FEATURE:
<221> NAME/KEY: CDS
<222> LOCATION: (1)..(660)
<220> FEATURE:
<221> NAME/KEY: sig_peptide
<222> LOCATION: (1)..(48)
<220> FEATURE:
<221> NAME/KEY: mat_peptide
<222> LOCATION: (49)..(660)

<400> SEQUENCE: 13
```

```
atg atc agg gca gtt gct att ctt tta tgt gcc tct gtc gca tac tgc      48
Met Ile Arg Ala Val Ala Ile Leu Leu Cys Ala Ser Val Ala Tyr Cys
    -15                 -10                  -5                  -1 gca ctg ccc aaa ggc att gat gta tct cat tgg caa gga gat gtg aac      96
Ala Leu Pro Lys Gly Ile Asp Val Ser His Trp Gln Gly Asp Val Asn
  1               5                  10                  15 tgg aat tcg gtg aaa gct gct gga att gaa ttt gtc tat atc aag gcg     144
Trp Asn Ser Val Lys Ala Ala Gly Ile Glu Phe Val Tyr Ile Lys Ala
                 20                  25                  30 act gag agt atc aac tac atc gat tcc aag ttc gac gca aat tac gtc     192
Thr Glu Ser Ile Asn Tyr Ile Asp Ser Lys Phe Asp Ala Asn Tyr Val
         35                  40                  45 ggc gcc act aac gca ggc tta att cgt gga ggc tac cat ttt gca cgt     240
Gly Ala Thr Asn Ala Gly Leu Ile Arg Gly Gly Tyr His Phe Ala Arg
 50                  55                  60 cca gct gct tcg agt ggt gcc gta caa gcc aac tat ttt ctt gct aat     288
Pro Ala Ala Ser Ser Gly Ala Val Gln Ala Asn Tyr Phe Leu Ala Asn
 65                  70                  75                  80 gga ggc gga tgg agt tcc gat ggt ata acc ctt cca ggt gct ctt gat     336
Gly Gly Gly Trp Ser Ser Asp Gly Ile Thr Leu Pro Gly Ala Leu Asp
                 85                  90                  95 ctt gag gct ggc tgc agt ggc cta agt caa gct gct atg acg gct tgg     384
Leu Glu Ala Gly Cys Ser Gly Leu Ser Gln Ala Ala Met Thr Ala Trp
            100                 105                 110 gtt cgc gat ttt tcg gac acg tac cac gcc agg act ggc cgc tac cct     432
Val Arg Asp Phe Ser Asp Thr Tyr His Ala Arg Thr Gly Arg Tyr Pro
```

-continued

```
                        115                 120                 125
gtc atc tat acc aca acc agt tgg tgg aaa caa tgt acc ggc aac gct    480
Val Ile Tyr Thr Thr Thr Ser Trp Trp Lys Gln Cys Thr Gly Asn Ala
    130                 135                 140 tcc ggc ttt caa aac aat aat ccg cta tgg att gct cgc tgg gct tct    528
Ser Gly Phe Gln Asn Asn Asn Pro Leu Trp Ile Ala Arg Trp Ala Ser
145                 150                 155                 160 tca gct ggc gag ctt cct gca ggg tat gcc ttc cat acc ttc tgg cag    576
Ser Ala Gly Glu Leu Pro Ala Gly Tyr Ala Phe His Thr Phe Trp Gln
                165                 170                 175 tac gcg gat aag ggg cct aat cca ggt gat caa gat tat ttc aac ggt    624
Tyr Ala Asp Lys Gly Pro Asn Pro Gly Asp Gln Asp Tyr Phe Asn Gly
            180                 185                 190 gac tct gct ggc ctc cga cgt ttc gct aaa ggt tcc tga                663
Asp Ser Ala Gly Leu Arg Arg Phe Ala Lys Gly Ser
                195                 200
```

<210> SEQ ID NO 14
<211> LENGTH: 220
<212> TYPE: PRT
<213> ORGANISM: Mortierella alpina

<400> SEQUENCE: 14

```
Met Ile Arg Ala Val Ala Ile Leu Leu Cys Ala Ser Val Ala Tyr Cys
    -15                 -10                  -5                  -1

Ala Leu Pro Lys Gly Ile Asp Val Ser His Trp Gln Gly Asp Val Asn
  1               5                  10                  15

Trp Asn Ser Val Lys Ala Ala Gly Ile Glu Phe Val Tyr Ile Lys Ala
                 20                  25                  30

Thr Glu Ser Ile Asn Tyr Ile Asp Ser Lys Phe Asp Ala Asn Tyr Val
             35                  40                  45

Gly Ala Thr Asn Ala Gly Leu Ile Arg Gly Gly Tyr His Phe Ala Arg
 50                  55                  60

Pro Ala Ala Ser Ser Gly Ala Val Gln Ala Asn Tyr Phe Leu Ala Asn
 65                  70                  75                  80

Gly Gly Gly Trp Ser Ser Asp Gly Ile Thr Leu Pro Gly Ala Leu Asp
                 85                  90                  95

Leu Glu Ala Gly Cys Ser Gly Leu Ser Gln Ala Ala Met Thr Ala Trp
            100                 105                 110

Val Arg Asp Phe Ser Asp Thr Tyr His Ala Arg Thr Gly Arg Tyr Pro
        115                 120                 125

Val Ile Tyr Thr Thr Thr Ser Trp Trp Lys Gln Cys Thr Gly Asn Ala
    130                 135                 140

Ser Gly Phe Gln Asn Asn Asn Pro Leu Trp Ile Ala Arg Trp Ala Ser
145                 150                 155                 160

Ser Ala Gly Glu Leu Pro Ala Gly Tyr Ala Phe His Thr Phe Trp Gln
                165                 170                 175

Tyr Ala Asp Lys Gly Pro Asn Pro Gly Asp Gln Asp Tyr Phe Asn Gly
            180                 185                 190

Asp Ser Ala Gly Leu Arg Arg Phe Ala Lys Gly Ser
        195                 200
```

<210> SEQ ID NO 15
<211> LENGTH: 204
<212> TYPE: PRT
<213> ORGANISM: Mortierella alpina
<220> FEATURE:
<221> NAME/KEY: mat_peptide

<222> LOCATION: (1)..(204)

<400> SEQUENCE: 15

```
Ala Leu Pro Lys Gly Ile Asp Val Ser His Trp Gln Gly Asp Val Asn
1               5                   10                  15
Trp Asn Ser Val Lys Ala Ala Gly Ile Glu Phe Val Tyr Ile Lys Ala
            20                  25                  30
Thr Glu Ser Ile Asn Tyr Ile Asp Ser Lys Phe Asp Ala Asn Tyr Val
        35                  40                  45
Gly Ala Thr Asn Ala Gly Leu Ile Arg Gly Tyr His Phe Ala Arg
50                  55                  60
Pro Ala Ala Ser Ser Gly Ala Val Gln Ala Asn Tyr Phe Leu Ala Asn
65                  70                  75                  80
Gly Gly Gly Trp Ser Ser Asp Gly Ile Thr Leu Pro Gly Ala Leu Asp
                85                  90                  95
Leu Glu Ala Gly Cys Ser Gly Leu Ser Gln Ala Ala Met Thr Ala Trp
            100                 105                 110
Val Arg Asp Phe Ser Asp Thr Tyr His Ala Arg Thr Gly Arg Tyr Pro
        115                 120                 125
Val Ile Tyr Thr Thr Thr Ser Trp Trp Lys Gln Cys Thr Gly Asn Ala
    130                 135                 140
Ser Gly Phe Gln Asn Asn Asn Pro Leu Trp Ile Ala Arg Trp Ala Ser
145                 150                 155                 160
Ser Ala Gly Glu Leu Pro Ala Gly Tyr Ala Phe His Thr Phe Trp Gln
                165                 170                 175
Tyr Ala Asp Lys Gly Pro Asn Pro Gly Asp Gln Asp Tyr Phe Asn Gly
            180                 185                 190
Asp Ser Ala Gly Leu Arg Arg Phe Ala Lys Gly Ser
        195                 200
```

<210> SEQ ID NO 16
<211> LENGTH: 742
<212> TYPE: DNA
<213> ORGANISM: Purpureocillium lilacinum
<220> FEATURE:
<221> NAME/KEY: CDS
<222> LOCATION: (1)..(147)
<220> FEATURE:
<221> NAME/KEY: sig_peptide
<222> LOCATION: (1)..(57)
<223> OTHER INFORMATION: 739
<220> FEATURE:
<221> NAME/KEY: mat_peptide
<222> LOCATION: (58)..(739)
<223> OTHER INFORMATION: 739
<220> FEATURE:
<221> NAME/KEY: CDS
<222> LOCATION: (206)..(739)
<223> OTHER INFORMATION: 739

<400> SEQUENCE: 16

```
atg aag ttc gca tcc gtc gcc gcc tct gtg tcc gcc ctc tgc ggc gtg        48
Met Lys Phe Ala Ser Val Ala Ala Ser Val Ser Ala Leu Cys Gly Val
            -15                 -10                 -5
gcc tct gcc gct gtc aag ggc ttt gac att tcc cac tac cag ccc aac        96
Ala Ser Ala Ala Val Lys Gly Phe Asp Ile Ser His Tyr Gln Pro Asn
    -1  1                   5                       10
gtc gac ttt gcc aag gcc tat gcc gat ggc gcc cgc ttc gtg atg atc       144
Val Asp Phe Ala Lys Ala Tyr Ala Asp Gly Ala Arg Phe Val Met Ile
            15                  20                  25
aag gtgcgttcac ccagatgaag agcttccccc gaattccatc taacgttcac            197
```

```
Lys
30 gtcggcag gcc acg gag ggc acc acg tac acg gac ccc agc ttc agc tcg    247
         Ala Thr Glu Gly Thr Thr Tyr Thr Asp Pro Ser Phe Ser Ser
                     35                  40 cac tac acg ggc gcc acc aag gcg ggc ttc atc cgc ggc ggc tac cac    295
His Tyr Thr Gly Ala Thr Lys Ala Gly Phe Ile Arg Gly Gly Tyr His
45                  50                  55                  60 ttt gcc cgc ccg gcg tcc tcg tcc ggt gcc gcg cag gcc aag tac ttt    343
Phe Ala Arg Pro Ala Ser Ser Ser Gly Ala Ala Gln Ala Lys Tyr Phe
                65                  70                  75 atc gcg cac ggc ggc ggc tgg tcc aag gac ggc atc acg ctg cct ggc    391
Ile Ala His Gly Gly Gly Trp Ser Lys Asp Gly Ile Thr Leu Pro Gly
            80                  85                  90 atg ctc gac atg gag tac cag tcg tcg agc agc gcg tgc ggg ggc ctc    439
Met Leu Asp Met Glu Tyr Gln Ser Ser Ser Ser Ala Cys Gly Gly Leu
        95                  100                 105 tca cag agc gcc atg gtc agc tgg atc aac gac ttt gtc aac acg tac    487
Ser Gln Ser Ala Met Val Ser Trp Ile Asn Asp Phe Val Asn Thr Tyr
    110                 115                 120 cac gcc gcc acg ggc gtc tac ccg ctc atc tac acc tcg acc agc tgg    535
His Ala Ala Thr Gly Val Tyr Pro Leu Ile Tyr Thr Ser Thr Ser Trp
125                 130                 135                 140 tgg acg cag tgc acg ggc aac agc gcc gcc ttt ggc agc aag tgc cct    583
Trp Thr Gln Cys Thr Gly Asn Ser Ala Ala Phe Gly Ser Lys Cys Pro
                145                 150                 155 ctc gtc gtc gcg cgc tat gct agc tcc gtc ggc acg ctc cct gct ggc    631
Leu Val Val Ala Arg Tyr Ala Ser Ser Val Gly Thr Leu Pro Ala Gly
            160                 165                 170 tgg ggc ttc tac acc ttc tgg cag tac tcg gac gcg gcg ccc tgg ggt    679
Trp Gly Phe Tyr Thr Phe Trp Gln Tyr Ser Asp Ala Ala Pro Trp Gly
        175                 180                 185 ggt gat gcg gat acc ttt aac ggc gac att act gct ctc aag aag att    727
Gly Asp Ala Asp Thr Phe Asn Gly Asp Ile Thr Ala Leu Lys Lys Ile
    190                 195                 200 gcc aac gcc ggt taa                                                742
Ala Asn Ala Gly
205

<210> SEQ ID NO 17
<211> LENGTH: 227
<212> TYPE: PRT
<213> ORGANISM: Purpureocillium lilacinum

<400> SEQUENCE: 17

Met Lys Phe Ala Ser Val Ala Ala Ser Val Ser Ala Leu Cys Gly Val
                -15                 -10                 -5

Ala Ser Ala Ala Val Lys Gly Phe Asp Ile Ser His Tyr Gln Pro Asn
        -1  1               5                   10

Val Asp Phe Ala Lys Ala Tyr Ala Asp Gly Ala Arg Phe Val Met Ile
    15                  20                  25

Lys Ala Thr Glu Gly Thr Thr Tyr Thr Asp Pro Ser Phe Ser Ser His
30                  35                  40                  45

Tyr Thr Gly Ala Thr Lys Ala Gly Phe Ile Arg Gly Gly Tyr His Phe
                50                  55                  60

Ala Arg Pro Ala Ser Ser Ser Gly Ala Ala Gln Ala Lys Tyr Phe Ile
            65                  70                  75

Ala His Gly Gly Gly Trp Ser Lys Asp Gly Ile Thr Leu Pro Gly Met
        80                  85                  90
```

```
Leu Asp Met Glu Tyr Gln Ser Ser Ser Ala Cys Gly Gly Leu Ser
 95                 100                 105

Gln Ser Ala Met Val Ser Trp Ile Asn Asp Phe Val Asn Thr Tyr His
110                 115                 120                 125

Ala Ala Thr Gly Val Tyr Pro Leu Ile Tyr Thr Ser Thr Ser Trp Trp
            130                 135                 140

Thr Gln Cys Thr Gly Asn Ser Ala Ala Phe Gly Ser Lys Cys Pro Leu
                145                 150                 155

Val Val Ala Arg Tyr Ala Ser Ser Val Gly Thr Leu Pro Ala Gly Trp
        160                 165                 170

Gly Phe Tyr Thr Phe Trp Gln Tyr Ser Asp Ala Ala Pro Trp Gly Gly
        175                 180                 185

Asp Ala Asp Thr Phe Asn Gly Asp Ile Thr Ala Leu Lys Lys Ile Ala
190                 195                 200                 205

Asn Ala Gly

<210> SEQ ID NO 18
<211> LENGTH: 208
<212> TYPE: PRT
<213> ORGANISM: Purpureocillium lilacinum
<220> FEATURE:
<221> NAME/KEY: mat_peptide
<222> LOCATION: (1)..(208)

<400> SEQUENCE: 18

Ala Val Lys Gly Phe Asp Ile Ser His Tyr Gln Pro Asn Val Asp Phe
1               5                   10                  15

Ala Lys Ala Tyr Ala Asp Gly Ala Arg Phe Val Met Ile Lys Ala Thr
            20                  25                  30

Glu Gly Thr Thr Tyr Thr Asp Pro Ser Phe Ser Ser His Tyr Thr Gly
        35                  40                  45

Ala Thr Lys Ala Gly Phe Ile Arg Gly Tyr His Phe Ala Arg Pro
    50                  55                  60

Ala Ser Ser Ser Gly Ala Ala Gln Ala Lys Tyr Phe Ile Ala His Gly
65                  70                  75                  80

Gly Gly Trp Ser Lys Asp Gly Ile Thr Leu Pro Gly Met Leu Asp Met
                85                  90                  95

Glu Tyr Gln Ser Ser Ser Ala Cys Gly Gly Leu Ser Gln Ser Ala
            100                 105                 110

Met Val Ser Trp Ile Asn Asp Phe Val Asn Thr Tyr His Ala Ala Thr
        115                 120                 125

Gly Val Tyr Pro Leu Ile Tyr Thr Ser Thr Ser Trp Trp Thr Gln Cys
    130                 135                 140

Thr Gly Asn Ser Ala Ala Phe Gly Ser Lys Cys Pro Leu Val Val Ala
145                 150                 155                 160

Arg Tyr Ala Ser Ser Val Gly Thr Leu Pro Ala Gly Trp Gly Phe Tyr
                165                 170                 175

Thr Phe Trp Gln Tyr Ser Asp Ala Ala Pro Trp Gly Gly Asp Ala Asp
            180                 185                 190

Thr Phe Asn Gly Asp Ile Thr Ala Leu Lys Lys Ile Ala Asn Ala Gly
        195                 200                 205

<210> SEQ ID NO 19
<211> LENGTH: 734
<212> TYPE: DNA
<213> ORGANISM: Onygena equina
```

```
<220> FEATURE:
<221> NAME/KEY: CDS
<222> LOCATION: (1)..(144)
<220> FEATURE:
<221> NAME/KEY: sig_peptide
<222> LOCATION: (1)..(54)
<220> FEATURE:
<221> NAME/KEY: mat_peptide
<222> LOCATION: (55)..(731)
<220> FEATURE:
<221> NAME/KEY: CDS
<222> LOCATION: (201)..(731)

<400> SEQUENCE: 19
```

| | | | | | | | | | | | | | | | | |
|---|---|---|---|---|---|---|---|---|---|---|---|---|---|---|---|---|
| atg | ttg | aaa | aca | att | atc | tat | acc | acc | ctt | gcc | gtc | gct | agc | ctg | gcg | 48 |
| Met | Leu | Lys | Thr | Ile | Ile | Tyr | Thr | Thr | Leu | Ala | Val | Ala | Ser | Leu | Ala | |
| | | | -15 | | | | -10 | | | | | -5 | | | | |
| tca | gca | gcc | gtt | ccc | ggt | atc | gac | gtg | tcg | ggc | tac | caa | ggc | aac | gtg | 96 |
| Ser | Ala | Ala | Val | Pro | Gly | Ile | Asp | Val | Ser | Gly | Tyr | Gln | Gly | Asn | Val | |
| | -1 | 1 | | | 5 | | | | | 10 | | | | | | |
| aac | tgg | gcg | aac | gtc | gcc | aac | gct | gga | aag | aag | ttt | gcc | tac | gtc | aag | 144 |
| Asn | Trp | Ala | Asn | Val | Ala | Asn | Ala | Gly | Lys | Lys | Phe | Ala | Tyr | Val | Lys | |
| 15 | | | | 20 | | | | | 25 | | | | | 30 | | |

```
gtatgcgtct ccgtaatgag ttatgaattg gaactaatca aatcaatcgg gcatag gcc       203
                                                                 Ala
```

| | | | | | | | | | | | | | | | | |
|---|---|---|---|---|---|---|---|---|---|---|---|---|---|---|---|---|
| acg | gaa | cat | acc | aac | tac | atc | aac | cct | tac | ttc | gcc | cag | cag | tac | aat | 251 |
| Thr | Glu | His | Thr | Asn | Tyr | Ile | Asn | Pro | Tyr | Phe | Ala | Gln | Gln | Tyr | Asn | |
| | | | 35 | | | | | 40 | | | | | 45 | | | |
| ggc | gcc | tac | aac | cag | ggc | att | att | cga | ggt | gca | tac | cac | tac | gcc | cac | 299 |
| Gly | Ala | Tyr | Asn | Gln | Gly | Ile | Ile | Arg | Gly | Ala | Tyr | His | Tyr | Ala | His | |
| | 50 | | | | | 55 | | | | | 60 | | | | | |
| ccc | aac | ggc | gca | agc | gga | gct | tct | cag | gcc | aac | tac | ttc | ctt | gct | cac | 347 |
| Pro | Asn | Gly | Ala | Ser | Gly | Ala | Ser | Gln | Ala | Asn | Tyr | Phe | Leu | Ala | His | |
| 65 | | | | | 70 | | | | | 75 | | | | | | |
| ggt | ggc | ggc | tgg | tct | gct | gat | ggg | aaa | acc | ctt | cct | ggt | gcc | gtc | gac | 395 |
| Gly | Gly | Gly | Trp | Ser | Ala | Asp | Gly | Lys | Thr | Leu | Pro | Gly | Ala | Val | Asp | |
| 80 | | | | 85 | | | | | 90 | | | | | 95 | | |
| ctc | gag | tac | gga | ccc | aat | ggc | agc | act | tgc | tgg | ggt | atc | agt | caa | tcg | 443 |
| Leu | Glu | Tyr | Gly | Pro | Asn | Gly | Ser | Thr | Cys | Trp | Gly | Ile | Ser | Gln | Ser | |
| | | | 100 | | | | | 105 | | | | | 110 | | | |
| gcg | atg | atc | gct | tgg | atc | cgt | gac | ttc | tcc | aac | acc | tac | cgt | gcc | aag | 491 |
| Ala | Met | Ile | Ala | Trp | Ile | Arg | Asp | Phe | Ser | Asn | Thr | Tyr | Arg | Ala | Lys | |
| | | 115 | | | | | 120 | | | | | 125 | | | | |
| acc | ggc | cgg | cct | cca | gtc | atc | tac | acc | agc | acc | tct | tgg | tgg | aag | acc | 539 |
| Thr | Gly | Arg | Pro | Pro | Val | Ile | Tyr | Thr | Ser | Thr | Ser | Trp | Trp | Lys | Thr | |
| | 130 | | | | | 135 | | | | | 140 | | | | | |
| tgc | acc | ggt | aac | tat | ggc | ggt | ttc | gga | aac | gat | aat | ccc | ctt | tgg | att | 587 |
| Cys | Thr | Gly | Asn | Tyr | Gly | Gly | Phe | Gly | Asn | Asp | Asn | Pro | Leu | Trp | Ile | |
| 145 | | | | | 150 | | | | | 155 | | | | | | |
| gct | cgt | tat | tca | agc | act | gtc | ggc | gaa | ctt | cct | gct | ggc | tgg | cct | ttc | 635 |
| Ala | Arg | Tyr | Ser | Ser | Thr | Val | Gly | Glu | Leu | Pro | Ala | Gly | Trp | Pro | Phe | |
| 160 | | | | | 165 | | | | | 170 | | | | | 175 | |
| cac | agc | atc | tgg | cag | aac | aac | gat | aac | agc | ggt | gtt | gga | ggg | gac | ggt | 683 |
| His | Ser | Ile | Trp | Gln | Asn | Asn | Asp | Asn | Ser | Gly | Val | Gly | Gly | Asp | Gly | |
| | | | 180 | | | | | 185 | | | | | 190 | | | |
| gat | atc | tgg | aac | ggt | gac | ctg | gct | gga | ttg | caa | cga | ttt | gca | aag | ggc | 731 |
| Asp | Ile | Trp | Asn | Gly | Asp | Leu | Ala | Gly | Leu | Gln | Arg | Phe | Ala | Lys | Gly | |
| | | 195 | | | | | 200 | | | | | 205 | | | | |

```
taa                                                                      734

<210> SEQ ID NO 20
<211> LENGTH: 225
```

```
<212> TYPE: PRT
<213> ORGANISM: Onygena equina

<400> SEQUENCE: 20

Met Leu Lys Thr Ile Ile Tyr Thr Thr Leu Ala Val Ala Ser Leu Ala
                -15                 -10                  -5

Ser Ala Ala Val Pro Gly Ile Asp Val Ser Gly Tyr Gln Gly Asn Val
     -1   1               5                      10

Asn Trp Ala Asn Val Ala Asn Ala Gly Lys Lys Phe Ala Tyr Val Lys
 15              20              25                      30

Ala Thr Glu His Thr Asn Tyr Ile Asn Pro Tyr Phe Ala Gln Gln Tyr
                 35              40                  45

Asn Gly Ala Tyr Asn Gln Gly Ile Ile Arg Gly Ala Tyr His Tyr Ala
             50              55                  60

His Pro Asn Gly Ala Ser Gly Ala Ser Gln Ala Asn Tyr Phe Leu Ala
             65              70                  75

His Gly Gly Gly Trp Ser Ala Asp Gly Lys Thr Leu Pro Gly Ala Val
         80              85                  90

Asp Leu Glu Tyr Gly Pro Asn Gly Ser Thr Cys Trp Gly Ile Ser Gln
 95              100                 105                 110

Ser Ala Met Ile Ala Trp Ile Arg Asp Phe Ser Asn Thr Tyr Arg Ala
                 115                 120                 125

Lys Thr Gly Arg Pro Pro Val Ile Tyr Thr Ser Thr Ser Trp Trp Lys
             130                 135                 140

Thr Cys Thr Gly Asn Tyr Gly Gly Phe Gly Asn Asp Asn Pro Leu Trp
             145                 150                 155

Ile Ala Arg Tyr Ser Ser Thr Val Gly Glu Leu Pro Ala Gly Trp Pro
 160                 165                 170

Phe His Ser Ile Trp Gln Asn Asn Asp Asn Ser Gly Val Gly Gly Asp
 175                 180                 185                 190

Gly Asp Ile Trp Asn Gly Asp Leu Ala Gly Leu Gln Arg Phe Ala Lys
             195                 200                 205

Gly

<210> SEQ ID NO 21
<211> LENGTH: 207
<212> TYPE: PRT
<213> ORGANISM: Onygena equina
<220> FEATURE:
<221> NAME/KEY: mat_peptide
<222> LOCATION: (1)..(207)

<400> SEQUENCE: 21

Ala Val Pro Gly Ile Asp Val Ser Gly Tyr Gln Gly Asn Val Asn Trp
 1               5                  10                  15

Ala Asn Val Ala Asn Ala Gly Lys Lys Phe Ala Tyr Val Lys Ala Thr
             20                  25                  30

Glu His Thr Asn Tyr Ile Asn Pro Tyr Phe Ala Gln Gln Tyr Asn Gly
         35                  40                  45

Ala Tyr Asn Gln Gly Ile Ile Arg Gly Ala Tyr His Tyr Ala His Pro
     50                  55                  60

Asn Gly Ala Ser Gly Ala Ser Gln Ala Asn Tyr Phe Leu Ala His Gly
 65                  70                  75                  80

Gly Gly Trp Ser Ala Asp Gly Lys Thr Leu Pro Gly Ala Val Asp Leu
                 85                  90                  95

Glu Tyr Gly Pro Asn Gly Ser Thr Cys Trp Gly Ile Ser Gln Ser Ala
```

-continued

```
                100                 105                 110
Met Ile Ala Trp Ile Arg Asp Phe Ser Asn Thr Tyr Arg Ala Lys Thr
            115                 120                 125

Gly Arg Pro Val Ile Tyr Thr Ser Thr Ser Trp Trp Lys Thr Cys
130                 135                 140

Thr Gly Asn Tyr Gly Gly Phe Gly Asn Asp Asn Pro Leu Trp Ile Ala
145                 150                 155                 160

Arg Tyr Ser Ser Thr Val Gly Glu Leu Pro Ala Gly Trp Pro Phe His
                165                 170                 175

Ser Ile Trp Gln Asn Asn Asp Asn Ser Gly Val Gly Gly Asp Gly Asp
            180                 185                 190

Ile Trp Asn Gly Asp Leu Ala Gly Leu Gln Arg Phe Ala Lys Gly
            195                 200                 205

<210> SEQ ID NO 22
<211> LENGTH: 829
<212> TYPE: DNA
<213> ORGANISM: Lecanicillium sp. WMM742
<220> FEATURE:
<221> NAME/KEY: CDS
<222> LOCATION: (1)..(147)
<220> FEATURE:
<221> NAME/KEY: sig_peptide
<222> LOCATION: (1)..(57)
<220> FEATURE:
<221> NAME/KEY: mat_peptide
<222> LOCATION: (58)..(826)
<220> FEATURE:
<221> NAME/KEY: CDS
<222> LOCATION: (210)..(393)
<220> FEATURE:
<221> NAME/KEY: CDS
<222> LOCATION: (480)..(826)

<400> SEQUENCE: 22 atg aag tct ttt ggc ctg ttc gcc tca ctc gcc tct ctg gct ggc atc      48
Met Lys Ser Phe Gly Leu Phe Ala Ser Leu Ala Ser Leu Ala Gly Ile
            -15                 -10                 -5 gcc agc gcc tcg gtc cag ggt ttt gac att tcc cac tac cag agc tct      96
Ala Ser Ala Ser Val Gln Gly Phe Asp Ile Ser His Tyr Gln Ser Ser
    -1  1                  5                  10 gtc aac ttt ggc gcg gcc tac gct gac ggc gct cgc ttc gtc att atc     144
Val Asn Phe Gly Ala Ala Tyr Ala Asp Gly Ala Arg Phe Val Ile Ile
     15                 20                 25 aag                                                                  197
Lys
30 cct tat cat t ag gca acc gag gga acg acg tac cgc gac ccc aag ttc agc    248
             Ala Thr Glu Gly Thr Thr Tyr Arg Asp Pro Lys Phe Ser
                                 35                 40 gag cac tac ggc ggc gcc acc aag gcc ggc ttc atc cgc ggc ggc tat      296
Glu His Tyr Gly Gly Ala Thr Lys Ala Gly Phe Ile Arg Gly Gly Tyr
45                 50                 55 cac ttt gcc cag cct gcc tca tcc tct ggc gcc gcg cag gcc aac ttt     344
His Phe Ala Gln Pro Ala Ser Ser Ser Gly Ala Ala Gln Ala Asn Phe
60                 65                 70                 75 ttc ctc gct cac ggc ggc ggc tgg agc ggc gac ggc atc acc ctg ccc g    393
Phe Leu Ala His Gly Gly Gly Trp Ser Gly Asp Gly Ile Thr Leu Pro
                80                 85                 90 gtaagcctcg cgcttataca cgcatgcttt tcacacccca gctcgacaaa gaaccctcat    453
ttctgattaa acttttgtgt gcttag gt atg ctg gat ctc gag tat ggc ccg      505
                              Gly Met Leu Asp Leu Glu Tyr Gly Pro
```

```
aac ggg aac acc tgc tac ggc ctc ggc ccg gcg tcc atg cgg agc tgg     553
Asn Gly Asn Thr Cys Tyr Gly Leu Gly Pro Ala Ser Met Arg Ser Trp
            105                 110                 115 atc agc gac ttt gtc gag acg tac cac gcc aag acg ggc cgc tac ccc     601
Ile Ser Asp Phe Val Glu Thr Tyr His Ala Lys Thr Gly Arg Tyr Pro
            120                 125                 130 ctc atc tac acg tcg acg agc tgg tgg aag acg tgc acg ggc aac acg     649
Leu Ile Tyr Thr Ser Thr Ser Trp Trp Lys Thr Cys Thr Gly Asn Thr
            135                 140                 145 tcc ctc ttt gcc gac aag tgc ccg ctg gtc gtc gcg cgc tat aac agc     697
Ser Leu Phe Ala Asp Lys Cys Pro Leu Val Val Ala Arg Tyr Asn Ser
    150                 155                 160 cag gtc ggc gag ctc cct gcc ggc tgg ggc ttc tac act ttc tgg cag     745
Gln Val Gly Glu Leu Pro Ala Gly Trp Gly Phe Tyr Thr Phe Trp Gln
165                 170                 175                 180 ttc aac gat cac tac aag cat ggc ggc gac tcg gac gtg ttc aac ggc     793
Phe Asn Asp His Tyr Lys His Gly Gly Asp Ser Asp Val Phe Asn Gly
                185                 190                 195 gcc tac tct cag ctt cag aag att gcc act ggt tag                     829
Ala Tyr Ser Gln Leu Gln Lys Ile Ala Thr Gly
                200                 205
```

<210> SEQ ID NO 23
<211> LENGTH: 226
<212> TYPE: PRT
<213> ORGANISM: Lecanicillium sp. WMM742

<400> SEQUENCE: 23

```
Met Lys Ser Phe Gly Leu Phe Ala Ser Leu Ala Ser Leu Ala Gly Ile
                -15                 -10                 -5

Ala Ser Ala Ser Val Gln Gly Phe Asp Ile Ser His Tyr Gln Ser Ser
        -1   1               5                   10

Val Asn Phe Gly Ala Ala Tyr Ala Asp Gly Ala Arg Phe Val Ile Ile
        15                  20                  25

Lys Ala Thr Glu Gly Thr Thr Tyr Arg Asp Pro Lys Phe Ser Glu His
30                  35                  40                  45

Tyr Gly Gly Ala Thr Lys Ala Gly Phe Ile Arg Gly Tyr His Phe
                50                  55                  60

Ala Gln Pro Ala Ser Ser Gly Ala Ala Gln Ala Asn Phe Phe Leu
            65                  70                  75

Ala His Gly Gly Gly Trp Ser Gly Asp Gly Ile Thr Leu Pro Gly Met
        80                  85                  90

Leu Asp Leu Glu Tyr Gly Pro Asn Gly Asn Thr Cys Tyr Gly Leu Gly
    95                  100                 105

Pro Ala Ser Met Arg Ser Trp Ile Ser Asp Phe Val Glu Thr Tyr His
110                 115                 120                 125

Ala Lys Thr Gly Arg Tyr Pro Leu Ile Tyr Thr Ser Thr Ser Trp Trp
                130                 135                 140

Lys Thr Cys Thr Gly Asn Thr Ser Leu Phe Ala Asp Lys Cys Pro Leu
            145                 150                 155

Val Val Ala Arg Tyr Asn Ser Gln Val Gly Glu Leu Pro Ala Gly Trp
        160                 165                 170

Gly Phe Tyr Thr Phe Trp Gln Phe Asn Asp His Tyr Lys His Gly Gly
    175                 180                 185

Asp Ser Asp Val Phe Asn Gly Ala Tyr Ser Gln Leu Gln Lys Ile Ala
190                 195                 200                 205
```

```
<210> SEQ ID NO 24
<211> LENGTH: 207
<212> TYPE: PRT
<213> ORGANISM: Lecanicillium sp. WMM742
<220> FEATURE:
<221> NAME/KEY: mat_peptide
<222> LOCATION: (1)..(207)

<400> SEQUENCE: 24
```

Ser Val Gln Gly Phe Asp Ile Ser His Tyr Gln Ser Ser Val Asn Phe
1               5                   10                  15

Gly Ala Ala Tyr Ala Asp Gly Ala Arg Phe Val Ile Lys Ala Thr
            20                  25                  30

Glu Gly Thr Thr Tyr Arg Asp Pro Lys Phe Ser Glu His Tyr Gly Gly
        35                  40                  45

Ala Thr Lys Ala Gly Phe Ile Arg Gly Tyr His Phe Ala Gln Pro
    50                  55                  60

Ala Ser Ser Ser Gly Ala Ala Gln Ala Asn Phe Phe Leu Ala His Gly
65                  70                  75                  80

Gly Gly Trp Ser Gly Asp Gly Ile Thr Leu Pro Gly Met Leu Asp Leu
                85                  90                  95

Glu Tyr Gly Pro Asn Gly Asn Thr Cys Tyr Gly Leu Gly Pro Ala Ser
            100                 105                 110

Met Arg Ser Trp Ile Ser Asp Phe Val Glu Thr Tyr His Ala Lys Thr
        115                 120                 125

Gly Arg Tyr Pro Leu Ile Tyr Thr Ser Thr Ser Trp Trp Lys Thr Cys
    130                 135                 140

Thr Gly Asn Thr Ser Leu Phe Ala Asp Lys Cys Pro Leu Val Val Ala
145                 150                 155                 160

Arg Tyr Asn Ser Gln Val Gly Glu Leu Pro Ala Gly Trp Gly Phe Tyr
                165                 170                 175

Thr Phe Trp Gln Phe Asn Asp His Tyr Lys His Gly Gly Asp Ser Asp
            180                 185                 190

Val Phe Asn Gly Ala Tyr Ser Gln Leu Gln Lys Ile Ala Thr Gly
        195                 200                 205

```
<210> SEQ ID NO 25
<211> LENGTH: 746
<212> TYPE: DNA
<213> ORGANISM: Penicillium atrovenetum
<220> FEATURE:
<221> NAME/KEY: CDS
<222> LOCATION: (1)..(159)
<220> FEATURE:
<221> NAME/KEY: SIG_PEPTIDE
<222> LOCATION: (1)..(45)
<220> FEATURE:
<221> NAME/KEY: mat_peptide
<222> LOCATION: (46)..(743)
<220> FEATURE:
<221> NAME/KEY: CDS
<222> LOCATION: (210)..(743)

<400> SEQUENCE: 25
``` atg aag atc act gcc ttc ccg ctt ctg ctc gct gcc gct agt gcc act        48
Met Lys Ile Thr Ala Phe Pro Leu Leu Leu Ala Ala Ala Ser Ala Thr
-15                 -10                 -5                  -1  1 cct ctt gag tcg cgc gct agc ggt gtc cag ggc ttc gat atc tcc agc        96
Pro Leu Glu Ser Arg Ala Ser Gly Val Gln Gly Phe Asp Ile Ser Ser

```
                 5                   10                  15
tac cag ggc acg gtc gac ttt gcc gga gca tat gct gca ggt gca cgc    144
Tyr Gln Gly Thr Val Asp Phe Ala Gly Ala Tyr Ala Ala Gly Ala Arg
             20                  25                  30 ttc gtc atg atc aag gtgaatttgt cgtccagcaa aggctgcaag tatgattgct    199
Phe Val Met Ile Lys
             35 aactacttag gcg acc gag ggc acc aca tac act gac aag acc ttc tcc    248
           Ala Thr Glu Gly Thr Thr Tyr Thr Asp Lys Thr Phe Ser
                       40                  45                  50 agt cac tat gag ggt gca tcc tca gct gga ttg atc cgc gga gga tat    296
Ser His Tyr Glu Gly Ala Ser Ser Ala Gly Leu Ile Arg Gly Gly Tyr
             55                  60                  65 cac ttc gct cac ccg gac agc tcc tct ggc gcc aaa cag gcc gag tat    344
His Phe Ala His Pro Asp Ser Ser Ser Gly Ala Lys Gln Ala Glu Tyr
             70                  75                  80 ttc ctt gcc cac ggt ggt ggt tgg tcc aac gat ggc aaa act ctc ccc    392
Phe Leu Ala His Gly Gly Gly Trp Ser Asn Asp Gly Lys Thr Leu Pro
        85                   90                  95 ggc atg ctg gat atc gaa tac aac ccg tct ggc gca acc tgc tat ggg    440
Gly Met Leu Asp Ile Glu Tyr Asn Pro Ser Gly Ala Thr Cys Tyr Gly
100                 105                 110                 115 atc agc aaa tct gcc atg gtt gcc tgg gtc aag gac ttt ggc gaa acc    488
Ile Ser Lys Ser Ala Met Val Ala Trp Val Lys Asp Phe Gly Glu Thr
                120                 125                 130 tac aag ggc aag act ggc cgc tac ccc atg atc tac acg act gca gac    536
Tyr Lys Gly Lys Thr Gly Arg Tyr Pro Met Ile Tyr Thr Thr Ala Asp
             135                 140                 145 tgg tgg aac acg tgc act gga ggc agc acc gcg ttc agc aag gat tac    584
Trp Trp Asn Thr Cys Thr Gly Gly Ser Thr Ala Phe Ser Lys Asp Tyr
             150                 155                 160 ccc tta gtg ttg gct cgg tac agc agc tct gtg ggc acc atc ccc ggt    632
Pro Leu Val Leu Ala Arg Tyr Ser Ser Ser Val Gly Thr Ile Pro Gly
             165                 170                 175 ggc tgg cca tac cag agc ttc tgg cag aac tcg gac aag tat acc tat    680
Gly Trp Pro Tyr Gln Ser Phe Trp Gln Asn Ser Asp Lys Tyr Thr Tyr
180                 185                 190                 195 ggt ggt gac tca gac ctt tgg aat ggc agc gag gcc tct ctc aag acc    728
Gly Gly Asp Ser Asp Leu Trp Asn Gly Ser Glu Ala Ser Leu Lys Thr
                200                 205                 210 ttc gcc aag ggt gct taa                                           746
Phe Ala Lys Gly Ala
             215

<210> SEQ ID NO 26
<211> LENGTH: 231
<212> TYPE: PRT
<213> ORGANISM: Penicillium atrovenetum

<400> SEQUENCE: 26

Met Lys Ile Thr Ala Phe Pro Leu Leu Leu Ala Ala Ala Ser Ala Thr
-15                 -10                  -5                  -1  1

Pro Leu Glu Ser Arg Ala Ser Gly Val Gln Gly Phe Asp Ile Ser Ser
             5                   10                  15

Tyr Gln Gly Thr Val Asp Phe Ala Gly Ala Tyr Ala Ala Gly Ala Arg
             20                  25                  30

Phe Val Met Ile Lys Ala Thr Glu Gly Thr Thr Tyr Thr Asp Lys Thr
             35                  40                  45

Phe Ser Ser His Tyr Glu Gly Ala Ser Ser Ala Gly Leu Ile Arg Gly
```

| | | 50 | | | 55 | | | 60 | | | 65 | |
|---|---|---|---|---|---|---|---|---|---|---|---|---|

Gly Tyr His Phe Ala His Pro Asp Ser Ser Gly Ala Lys Gln Ala
                     70                   75                   80

Glu Tyr Phe Leu Ala His Gly Gly Gly Trp Ser Asn Asp Gly Lys Thr
            85               90                   95

Leu Pro Gly Met Leu Asp Ile Glu Tyr Asn Pro Ser Gly Ala Thr Cys
          100                105               110

Tyr Gly Ile Ser Lys Ser Ala Met Val Ala Trp Val Lys Asp Phe Gly
     115                 120                 125

Glu Thr Tyr Lys Gly Lys Thr Gly Arg Tyr Pro Met Ile Tyr Thr Thr
130                 135               140               145

Ala Asp Trp Trp Asn Thr Cys Thr Gly Gly Ser Thr Ala Phe Ser Lys
              150               155               160

Asp Tyr Pro Leu Val Leu Ala Arg Tyr Ser Ser Val Gly Thr Ile
         165                170               175

Pro Gly Gly Trp Pro Tyr Gln Ser Phe Trp Gln Asn Ser Asp Lys Tyr
          180                185               190

Thr Tyr Gly Gly Asp Ser Asp Leu Trp Asn Gly Ser Glu Ala Ser Leu
     195                 200                 205

Lys Thr Phe Ala Lys Gly Ala
210                 215

<210> SEQ ID NO 27
<211> LENGTH: 216
<212> TYPE: PRT
<213> ORGANISM: Penicillium atrovenetum

<400> SEQUENCE: 27

Thr Pro Leu Glu Ser Arg Ala Ser Gly Val Gln Gly Phe Asp Ile Ser
1               5                   10                   15

Ser Tyr Gln Gly Thr Val Asp Phe Ala Gly Ala Tyr Ala Ala Gly Ala
           20                25               30

Arg Phe Val Met Ile Lys Ala Thr Glu Gly Thr Thr Tyr Thr Asp Lys
        35                40               45

Thr Phe Ser Ser His Tyr Glu Gly Ala Ser Ser Ala Gly Leu Ile Arg
     50                 55                 60

Gly Gly Tyr His Phe Ala His Pro Asp Ser Ser Gly Ala Lys Gln
65                 70                 75                 80

Ala Glu Tyr Phe Leu Ala His Gly Gly Trp Ser Asn Asp Gly Lys
             85               90                 95

Thr Leu Pro Gly Met Leu Asp Ile Glu Tyr Asn Pro Ser Gly Ala Thr
           100              105              110

Cys Tyr Gly Ile Ser Lys Ser Ala Met Val Ala Trp Val Lys Asp Phe
        115              120              125

Gly Glu Thr Tyr Lys Gly Lys Thr Gly Arg Tyr Pro Met Ile Tyr Thr
     130               135              140

Thr Ala Asp Trp Trp Asn Thr Cys Thr Gly Gly Ser Thr Ala Phe Ser
145               150               155               160

Lys Asp Tyr Pro Leu Val Leu Ala Arg Tyr Ser Ser Val Gly Thr
             165               170               175

Ile Pro Gly Gly Trp Pro Tyr Gln Ser Phe Trp Gln Asn Ser Asp Lys
          180              185              190

Tyr Thr Tyr Gly Gly Asp Ser Asp Leu Trp Asn Gly Ser Glu Ala Ser
        195              200              205

```
                Leu Lys Thr Phe Ala Lys Gly Ala
                    210                 215

<210> SEQ ID NO 28
<211> LENGTH: 767
<212> TYPE: DNA
<213> ORGANISM: Malbranchea flava
<220> FEATURE:
<221> NAME/KEY: CDS
<222> LOCATION: (1)..(174)
<220> FEATURE:
<221> NAME/KEY: sig_peptide
<222> LOCATION: (1)..(54)
<220> FEATURE:
<221> NAME/KEY: mat_peptide
<222> LOCATION: (55)..(764)
<220> FEATURE:
<221> NAME/KEY: CDS
<222> LOCATION: (234)..(764)

<400> SEQUENCE: 28 atg aag ctg tct ctc ctc ctt att gtt gct gca tca ctg gcc gtg gcc     48
Met Lys Leu Ser Leu Leu Leu Ile Val Ala Ala Ser Leu Ala Val Ala
            -15                 -10                 -5 agt gca ggc ccc aag gag ttc gag tca cgc gcg tcg ggc gtc cag ggc     96
Ser Ala Gly Pro Lys Glu Phe Glu Ser Arg Ala Ser Gly Val Gln Gly
    -1  1               5                  10 ttt gac atc tct ggt tgg cag tcc aac gtc aat ttt gca ggt gca tac    144
Phe Asp Ile Ser Gly Trp Gln Ser Asn Val Asn Phe Ala Gly Ala Tyr
15                  20                  25                  30 aat tct ggc gca cgc ttc gtc atg atc aag gtacatttga gtgaattcgt      194
Asn Ser Gly Ala Arg Phe Val Met Ile Lys
                35                  40 ttctcctggt ataatatccct gactaatgta aagatccag gct agc gag ggt acc    248
                                            Ala Ser Glu Gly Thr
                                                            45 acc ttc aag gac cgt caa ttc agc aat cat tac att ggc gcc acc aag    296
Thr Phe Lys Asp Arg Gln Phe Ser Asn His Tyr Ile Gly Ala Thr Lys
                50                  55                  60 gct ggc ttt atc cgt ggc ggc tac cac ttt gcg ttg cca gac gtc agc    344
Ala Gly Phe Ile Arg Gly Gly Tyr His Phe Ala Leu Pro Asp Val Ser
                65                  70                  75 agc gcc act gcc caa gtg aac cat ttc ctg gcc agc ggt ggt ggc tgg    392
Ser Ala Thr Ala Gln Val Asn His Phe Leu Ala Ser Gly Gly Gly Trp
                80                  85                  90 agc aga gac ggc atc acg ctg ccg ggc atg ctg gac atc gag agc aac    440
Ser Arg Asp Gly Ile Thr Leu Pro Gly Met Leu Asp Ile Glu Ser Asn
                95                 100                 105 ccg tat ggc gcc cag tgc tac ggc ctt gac gct ggt cgt atg gtt gcc    488
Pro Tyr Gly Ala Gln Cys Tyr Gly Leu Asp Ala Gly Arg Met Val Ala
110                 115                 120                 125 tgg atc cgg gag ttt gtt gac gcg tac aag cgc gca act gga cgg tat    536
Trp Ile Arg Glu Phe Val Asp Ala Tyr Lys Arg Ala Thr Gly Arg Tyr
                130                 135                 140 cct ctg atc tac acg tct ccc agc tgg tgg cag act tgc acg ggc aat    584
Pro Leu Ile Tyr Thr Ser Pro Ser Trp Trp Gln Thr Cys Thr Gly Asn
                145                 150                 155 agc aat gcc ttt ata gac aag tgc ccg ctt gtg ttg gca cgg tgg gcg    632
Ser Asn Ala Phe Ile Asp Lys Cys Pro Leu Val Leu Ala Arg Trp Ala
                160                 165                 170 agt agc cct ggc act ccg cct ggt ggg tgg ccg ttc cac agt ttt tgg    680
Ser Ser Pro Gly Thr Pro Pro Gly Gly Trp Pro Phe His Ser Phe Trp
175                 180                 185
```

-continued

```
cag tac gcc gat tcc tat caa ttc ggt ggt gac gcc cag gta ttc aat    728
Gln Tyr Ala Asp Ser Tyr Gln Phe Gly Gly Asp Ala Gln Val Phe Asn
190             195                 200                 205 ggc gat gag gct ggg ttg aag aga atg gcc cta ggt taa                767
Gly Asp Glu Ala Gly Leu Lys Arg Met Ala Leu Gly
            210                 215
```

<210> SEQ ID NO 29
<211> LENGTH: 235
<212> TYPE: PRT
<213> ORGANISM: Malbranchea flava

<400> SEQUENCE: 29

Met Lys Leu Ser Leu Leu Leu Ile Val Ala Ala Ser Leu Ala Val Ala
            -15                 -10                  -5

Ser Ala Gly Pro Lys Glu Phe Glu Ser Arg Ala Ser Gly Val Gln Gly
    -1   1               5                  10

Phe Asp Ile Ser Gly Trp Gln Ser Asn Val Asn Phe Ala Gly Ala Tyr
 15              20                  25                  30

Asn Ser Gly Ala Arg Phe Val Met Ile Lys Ala Ser Glu Gly Thr Thr
                 35                  40                  45

Phe Lys Asp Arg Gln Phe Ser Asn His Tyr Ile Gly Ala Thr Lys Ala
             50                  55                  60

Gly Phe Ile Arg Gly Gly Tyr His Phe Ala Leu Pro Asp Val Ser Ser
         65                  70                  75

Ala Thr Ala Gln Val Asn His Phe Leu Ala Ser Gly Gly Gly Trp Ser
     80                  85                  90

Arg Asp Gly Ile Thr Leu Pro Gly Met Leu Asp Ile Glu Ser Asn Pro
 95                 100                 105                 110

Tyr Gly Ala Gln Cys Tyr Gly Leu Asp Ala Gly Arg Met Val Ala Trp
                115                 120                 125

Ile Arg Glu Phe Val Asp Ala Tyr Lys Arg Ala Thr Gly Arg Tyr Pro
            130                 135                 140

Leu Ile Tyr Thr Ser Pro Ser Trp Trp Gln Thr Cys Thr Gly Asn Ser
        145                 150                 155

Asn Ala Phe Ile Asp Lys Cys Pro Leu Val Leu Ala Arg Trp Ala Ser
    160                 165                 170

Ser Pro Gly Thr Pro Pro Gly Gly Trp Pro Phe His Ser Phe Trp Gln
175                 180                 185                 190

Tyr Ala Asp Ser Tyr Gln Phe Gly Gly Asp Ala Gln Val Phe Asn Gly
                195                 200                 205

Asp Glu Ala Gly Leu Lys Arg Met Ala Leu Gly
            210                 215

<210> SEQ ID NO 30
<211> LENGTH: 217
<212> TYPE: PRT
<213> ORGANISM: Malbranchea flava
<220> FEATURE:
<221> NAME/KEY: mat_peptide
<222> LOCATION: (1)..(217)

<400> SEQUENCE: 30

Gly Pro Lys Glu Phe Glu Ser Arg Ala Ser Gly Val Gln Gly Phe Asp
 1               5                  10                  15

Ile Ser Gly Trp Gln Ser Asn Val Asn Phe Ala Gly Ala Tyr Asn Ser
             20                  25                  30

Gly Ala Arg Phe Val Met Ile Lys Ala Ser Glu Gly Thr Thr Phe Lys

```
        35                  40                  45
Asp Arg Gln Phe Ser Asn His Tyr Ile Gly Ala Thr Lys Ala Gly Phe
 50                  55                  60

Ile Arg Gly Gly Tyr His Phe Ala Leu Pro Asp Val Ser Ser Ala Thr
 65                  70                  75                  80

Ala Gln Val Asn His Phe Leu Ala Ser Gly Gly Trp Ser Arg Asp
                 85                  90                  95

Gly Ile Thr Leu Pro Gly Met Leu Asp Ile Glu Ser Asn Pro Tyr Gly
                100                 105                 110

Ala Gln Cys Tyr Gly Leu Asp Ala Gly Arg Met Val Ala Trp Ile Arg
                115                 120                 125

Glu Phe Val Asp Ala Tyr Lys Arg Ala Thr Gly Arg Tyr Pro Leu Ile
            130                 135                 140

Tyr Thr Ser Pro Ser Trp Trp Gln Thr Cys Thr Gly Asn Ser Asn Ala
145                 150                 155                 160

Phe Ile Asp Lys Cys Pro Leu Val Leu Ala Arg Trp Ala Ser Ser Pro
                165                 170                 175

Gly Thr Pro Pro Gly Gly Trp Pro Phe His Ser Phe Trp Gln Tyr Ala
                180                 185                 190

Asp Ser Tyr Gln Phe Gly Gly Asp Ala Gln Val Phe Asn Gly Asp Glu
            195                 200                 205

Ala Gly Leu Lys Arg Met Ala Leu Gly
        210                 215

<210> SEQ ID NO 31
<211> LENGTH: 782
<212> TYPE: DNA
<213> ORGANISM: Engyodontium album
<220> FEATURE:
<221> NAME/KEY: CDS
<222> LOCATION: (1)..(150)
<220> FEATURE:
<221> NAME/KEY: sig_peptide
<222> LOCATION: (1)..(60)
<220> FEATURE:
<221> NAME/KEY: mat_peptide
<222> LOCATION: (61)..(779)
<220> FEATURE:
<221> NAME/KEY: CDS
<222> LOCATION: (200)..(383)
<220> FEATURE:
<221> NAME/KEY: CDS
<222> LOCATION: (433)..(779)

<400> SEQUENCE: 31 atg aag tct ttt ggt gtt att gct acc ggt ttg gcc acc ctt gtg ggt      48
Met Lys Ser Phe Gly Val Ile Ala Thr Gly Leu Ala Thr Leu Val Gly
-20                 -15                 -10                  -5 gtt gcc tct gcc aga gtc caa ggt ttc gac atc tcc cac tat cag ccc      96
Val Ala Ser Ala Arg Val Gln Gly Phe Asp Ile Ser His Tyr Gln Pro
             -1   1               5                  10 agc gtc gac ttc aat gcg gcc tat gct gac gga gct cgc ttt gtg atc     144
Ser Val Asp Phe Asn Ala Ala Tyr Ala Asp Gly Ala Arg Phe Val Ile
         15                  20                  25 atc aag gtataacaaa ccataacttg gcttatgaac accatctaat gtattgcag gca   202
Ile Lys                                                         Ala
     30 acc gag ggt acc acc tac aaa gat ccc aag ttc agc cag cac tac atc     250
Thr Glu Gly Thr Thr Tyr Lys Asp Pro Lys Phe Ser Gln His Tyr Ile
             35                  40                  45 ggt gct acc aac gcc gga ttc atc cgc ggt ggc tac cac ttt gct cag     298
```

```
                                  -continued

Gly Ala Thr Asn Ala Gly Phe Ile Arg Gly Gly Tyr His Phe Ala Gln
            50                  55                  60 cct gct tcc tct tct ggt gca gcg cag gca gac tat ttc ctc aag aac      346
Pro Ala Ser Ser Ser Gly Ala Ala Gln Ala Asp Tyr Phe Leu Lys Asn
65                  70                  75 gga ggt ggt tgg tct agc gat gga att act ctc cca g                    393
Gly Gly Gly Trp Ser Ser Asp Gly Ile Thr Leu Pro
        80                  85                  90 tcacaaacgt tcgagggcag ttcactaata tcgtggcag  gt atg ctt gat atg   446
                                                        Gly Met Leu Asp Met
                                                                    95 gag tac aac ccc aat ggc agt gct tgc tac ggt ctt tcc cag gct tcc      494
Glu Tyr Asn Pro Asn Gly Ser Ala Cys Tyr Gly Leu Ser Gln Ala Ser
                100                 105                 110 atg cgc aac tgg atc aac gac ttt gtc aac acc tac cac tcc cgc acg      542
Met Arg Asn Trp Ile Asn Asp Phe Val Asn Thr Tyr His Ser Arg Thr
                115                 120                 125 ggt gtc tac cct ctc ctt tac acc acc acc agc tgg tgg aaa acc tgc      590
Gly Val Tyr Pro Leu Leu Tyr Thr Thr Thr Ser Trp Trp Lys Thr Cys
            130                 135                 140 acg ggt aac act gcc atg ttt gcc gac aag tgc cct ctc gtc atc gct      638
Thr Gly Asn Thr Ala Met Phe Ala Asp Lys Cys Pro Leu Val Ile Ala
145                 150                 155                 160 cgc tac aac agc gta gtc gga gag ctc ccc gct ggt tgg tct ttc tgg      686
Arg Tyr Asn Ser Val Val Gly Glu Leu Pro Ala Gly Trp Ser Phe Trp
                165                 170                 175 aca att tgg cag tac aac gac cac tac aag cat ggt ggt gac tca gac      734
Thr Ile Trp Gln Tyr Asn Asp His Tyr Lys His Gly Gly Asp Ser Asp
                180                 185                 190 gct ttt aac gga gac tac tct cag ctt cag aga atc gcc aga ggc taa      782
Ala Phe Asn Gly Asp Tyr Ser Gln Leu Gln Arg Ile Ala Arg Gly
            195                 200                 205

<210> SEQ ID NO 32
<211> LENGTH: 227
<212> TYPE: PRT
<213> ORGANISM: Engyodontium album

<400> SEQUENCE: 32

Met Lys Ser Phe Gly Val Ile Ala Thr Gly Leu Ala Thr Leu Val Gly
-20                 -15                 -10                 -5

Val Ala Ser Ala Arg Val Gln Gly Phe Asp Ile Ser His Tyr Gln Pro
                -1  1               5                   10

Ser Val Asp Phe Asn Ala Ala Tyr Ala Asp Gly Ala Arg Phe Val Ile
            15                  20                  25

Ile Lys Ala Thr Glu Gly Thr Thr Tyr Lys Asp Pro Lys Phe Ser Gln
        30                  35                  40

His Tyr Ile Gly Ala Thr Asn Ala Gly Phe Ile Arg Gly Gly Tyr His
45                  50                  55                  60

Phe Ala Gln Pro Ala Ser Ser Ser Gly Ala Ala Gln Ala Asp Tyr Phe
                65                  70                  75

Leu Lys Asn Gly Gly Gly Trp Ser Ser Asp Gly Ile Thr Leu Pro Gly
            80                  85                  90

Met Leu Asp Met Glu Tyr Asn Pro Asn Gly Ser Ala Cys Tyr Gly Leu
        95                  100                 105

Ser Gln Ala Ser Met Arg Asn Trp Ile Asn Asp Phe Val Asn Thr Tyr
    110                 115                 120

His Ser Arg Thr Gly Val Tyr Pro Leu Leu Tyr Thr Thr Thr Ser Trp
```

```
                125                 130                 135                 140
Trp Lys Thr Cys Thr Gly Asn Thr Ala Met Phe Ala Asp Lys Cys Pro
                145                 150                 155
Leu Val Ile Ala Arg Tyr Asn Ser Val Val Gly Glu Leu Pro Ala Gly
                160                 165                 170
Trp Ser Phe Trp Thr Ile Trp Gln Tyr Asn Asp His Tyr Lys His Gly
                175                 180                 185
Gly Asp Ser Asp Ala Phe Asn Gly Asp Tyr Ser Gln Leu Gln Arg Ile
                190                 195                 200
Ala Arg Gly
205

<210> SEQ ID NO 33
<211> LENGTH: 207
<212> TYPE: PRT
<213> ORGANISM: Engyodontium album
<220> FEATURE:
<221> NAME/KEY: mat_peptide
<222> LOCATION: (1)..(207)

<400> SEQUENCE: 33

Arg Val Gln Gly Phe Asp Ile Ser His Tyr Gln Pro Ser Val Asp Phe
1               5                   10                  15
Asn Ala Ala Tyr Ala Asp Gly Ala Arg Phe Val Ile Ile Lys Ala Thr
                20                  25                  30
Glu Gly Thr Thr Tyr Lys Asp Pro Lys Phe Ser Gln His Tyr Ile Gly
                35                  40                  45
Ala Thr Asn Ala Gly Phe Ile Arg Gly Gly Tyr His Phe Ala Gln Pro
        50                  55                  60
Ala Ser Ser Ser Gly Ala Ala Gln Ala Asp Tyr Phe Leu Lys Asn Gly
65              70                  75                  80
Gly Gly Trp Ser Ser Asp Gly Ile Thr Leu Pro Gly Met Leu Asp Met
                85                  90                  95
Glu Tyr Asn Pro Asn Gly Ser Ala Cys Tyr Gly Leu Ser Gln Ala Ser
                100                 105                 110
Met Arg Asn Trp Ile Asn Asp Phe Val Asn Thr Tyr His Ser Arg Thr
                115                 120                 125
Gly Val Tyr Pro Leu Leu Tyr Thr Thr Thr Ser Trp Trp Lys Thr Cys
                130                 135                 140
Thr Gly Asn Thr Ala Met Phe Ala Asp Lys Cys Pro Leu Val Ile Ala
145                 150                 155                 160
Arg Tyr Asn Ser Val Val Gly Glu Leu Pro Ala Gly Trp Ser Phe Trp
                165                 170                 175
Thr Ile Trp Gln Tyr Asn Asp His Tyr Lys His Gly Gly Asp Ser Asp
                180                 185                 190
Ala Phe Asn Gly Asp Tyr Ser Gln Leu Gln Arg Ile Ala Arg Gly
                195                 200                 205

<210> SEQ ID NO 34
<211> LENGTH: 1052
<212> TYPE: DNA
<213> ORGANISM: Flammulina velutipes
<220> FEATURE:
<221> NAME/KEY: CDS
<222> LOCATION: (1)..(157)
<220> FEATURE:
<221> NAME/KEY: sig_peptide
<222> LOCATION: (1)..(51)
<220> FEATURE:
```

```
<221> NAME/KEY: mat_peptide
<222> LOCATION: (52)..(1049)
<220> FEATURE:
<221> NAME/KEY: CDS
<222> LOCATION: (213)..(347)
<220> FEATURE:
<221> NAME/KEY: CDS
<222> LOCATION: (401)..(451)
<220> FEATURE:
<221> NAME/KEY: CDS
<222> LOCATION: (504)..(600)
<220> FEATURE:
<221> NAME/KEY: CDS
<222> LOCATION: (659)..(666)
<220> FEATURE:
<221> NAME/KEY: CDS
<222> LOCATION: (715)..(838)
<220> FEATURE:
<221> NAME/KEY: CDS
<222> LOCATION: (895)..(981)
<220> FEATURE:
<221> NAME/KEY: CDS
<222> LOCATION: (1037)..(1049)

<400> SEQUENCE: 34 atg cgc atc tta ctc ttc atc gct gtg acc att gca ctc ggc gtc cat      48
Met Arg Ile Leu Leu Phe Ile Ala Val Thr Ile Ala Leu Gly Val His
    -15                 -10                 -5 gct cgt ctc aat ggc atc gac gtt tcc ggg tat cag ccg aac gtc aac      96
Ala Arg Leu Asn Gly Ile Asp Val Ser Gly Tyr Gln Pro Asn Val Asn
 -1  1               5                  10                  15 tgg gcc act gtc aag gct aat ggc gtc tca ttc gcg tat atc aag gcc     144
Trp Ala Thr Val Lys Ala Asn Gly Val Ser Phe Ala Tyr Ile Lys Ala
                 20                  25                  30 acc gaa ggc act a gtaagttcac ttcctatatc cttttggtcc agtgctgata       197
Thr Glu Gly Thr
              35 tcatcgacaa cccag ct  tat acg aac ccg tcg ttc tca tcg caa tac acc    247
                    Thr Tyr Thr Asn Pro Ser Phe Ser Ser Gln Tyr Thr
                                 40                  45 gga gct acc aaa gct gga ctc att cga gga tcg tac cat ttt gcg cac     295
Gly Ala Thr Lys Ala Gly Leu Ile Arg Gly Ser Tyr His Phe Ala His
         50                  55                  60 cca agt agt agc acg ggc gct gca cag gcc aga tac ttt gtc gcg cat     343
Pro Ser Ser Ser Thr Gly Ala Ala Gln Ala Arg Tyr Phe Val Ala His
         65                  70                  75 ggc g gtaggaattg atccatcttg tgtggcgtcc cccattgaca caatccttga tag    400
Gly
 80 gt  ggc tgg tcg gga gac gga atc act ctg cct ggg gcg ctg gat ata    447
    Gly Trp Ser Gly Asp Gly Ile Thr Leu Pro Gly Ala Leu Asp Ile
                 85                  90                  95 gaa t gtaatgatca gtcagatcta ttacgttttg agtcacattg acaacttctt ag    503
Glu ac  aat cca agt ggc gca act tgc tac ggc ctg agt acc tca tca atg    550
    Tyr Asn Pro Ser Gly Ala Thr Cys Tyr Gly Leu Ser Thr Ser Ser Met
                100                 105                 110 gtc aat tgg att gcc gac ttc tct aac act tac cat tcc ctc act gga    598
Val Asn Trp Ile Ala Asp Phe Ser Asn Thr Tyr His Ser Leu Thr Gly
        115                 120                 125 ag  gttaggcttc gtaaacacaa gccatgtact gccgtagtaa cgctaatctc         650
Arg
130 catttcag a tac cct g gtacaccaat cccacaatca ttttgagtct gctcatctcc   706
           Tyr Pro
```

```
cct gac agt a    att tac acc acc gca gac tgg tgg agg aca tgt act ggt      755
        Val Ile Tyr Thr Thr Ala Asp Trp Trp Arg Thr Cys Thr Gly
                135                 140                 145 aac agt gca tcc ttt gcc aac aac agt cct ctc tgg att gcg aga tat          803
Asn Ser Ala Ser Phe Ala Asn Asn Ser Pro Leu Trp Ile Ala Arg Tyr
            150                 155                 160 gcc agt acc atc ggt aca ctc cct gct gga tgg ag  gtgcgaccct               848
Ala Ser Thr Ile Gly Thr Leu Pro Ala Gly Trp Ser
            165                 170 tctacttatt cgatgactct gttctgaacc aagtgttcat tctaag c tac gcc aca         904
                                                    Tyr Ala Thr
                                                            175 ttc tgg cag tac gct gac tcg ggt agt aat ccc gga gat cag gat tat          952
Phe Trp Gln Tyr Ala Asp Ser Gly Ser Asn Pro Gly Asp Gln Asp Tyr
            180                 185                 190 ttc aac ggg gat gct gca ggt ctc aaa cg  gtaaattgat atcttttat            1001
Phe Asn Gly Asp Ala Ala Gly Leu Lys Arg
    195                 200 atatcttcac ctgcgagact aatccatgtt tatag g ctt gcc acc agt tga            1052
                                        Leu Ala Thr Ser
                                                    205

<210> SEQ ID NO 35
<211> LENGTH: 224
<212> TYPE: PRT
<213> ORGANISM: Flammulina velutipes

<400> SEQUENCE: 35

Met Arg Ile Leu Leu Phe Ile Ala Val Thr Ile Ala Leu Gly Val His
        -15                 -10                  -5

Ala Arg Leu Asn Gly Ile Asp Val Ser Gly Tyr Gln Pro Asn Val Asn
 -1  1               5                  10                  15

Trp Ala Thr Val Lys Ala Asn Gly Val Ser Phe Ala Tyr Ile Lys Ala
                20                  25                  30

Thr Glu Gly Thr Thr Tyr Thr Asn Pro Ser Phe Ser Ser Gln Tyr Thr
                35                  40                  45

Gly Ala Thr Lys Ala Gly Leu Ile Arg Gly Ser Tyr His Phe Ala His
            50                  55                  60

Pro Ser Ser Ser Thr Gly Ala Ala Gln Ala Arg Tyr Phe Val Ala His
 65                  70                  75

Gly Gly Gly Trp Ser Gly Asp Gly Ile Thr Leu Pro Gly Ala Leu Asp
 80                  85                  90                  95

Ile Glu Tyr Asn Pro Ser Gly Ala Thr Cys Tyr Gly Leu Ser Thr Ser
                100                 105                 110

Ser Met Val Asn Trp Ile Ala Asp Phe Ser Asn Thr Tyr His Ser Leu
            115                 120                 125

Thr Gly Arg Tyr Pro Val Ile Tyr Thr Thr Ala Asp Trp Trp Arg Thr
        130                 135                 140

Cys Thr Gly Asn Ser Ala Ser Phe Ala Asn Asn Ser Pro Leu Trp Ile
    145                 150                 155

Ala Arg Tyr Ala Ser Thr Ile Gly Thr Leu Pro Ala Gly Trp Ser Tyr
160                 165                 170                 175

Ala Thr Phe Trp Gln Tyr Ala Asp Ser Gly Ser Asn Pro Gly Asp Gln
                180                 185                 190

Asp Tyr Phe Asn Gly Asp Ala Ala Gly Leu Lys Arg Leu Ala Thr Ser
            195                 200                 205
```

<210> SEQ ID NO 36
<211> LENGTH: 675
<212> TYPE: DNA
<213> ORGANISM: Artificial Sequence
<220> FEATURE:
<223> OTHER INFORMATION: Codon optimised sequence
<220> FEATURE:
<221> NAME/KEY: CDS
<222> LOCATION: (1)..(672)
<220> FEATURE:
<221> NAME/KEY: sig_peptide
<222> LOCATION: (1)..(51)
<220> FEATURE:
<221> NAME/KEY: mat_peptide
<222> LOCATION: (52)..(672)

<400> SEQUENCE: 36

```
atg cga atc ctc ttg ttc atc gca gtc aca atc gcg ttg gga gtc cat     48
Met Arg Ile Leu Leu Phe Ile Ala Val Thr Ile Ala Leu Gly Val His
        -15                 -10                 -5 gcc agg ctc aac ggc atc gat gtc tcg gga tac cag ccg aac gtc aac     96
Ala Arg Leu Asn Gly Ile Asp Val Ser Gly Tyr Gln Pro Asn Val Asn
 -1   1               5                  10                 15 tgg gcc acg gtc aaa gcg aac ggc gtg tcc ttc gcg tac atc aag gca    144
Trp Ala Thr Val Lys Ala Asn Gly Val Ser Phe Ala Tyr Ile Lys Ala
                20                  25                  30 acc gag ggc acc acg tat aca aac ccc tcg ttc tcc tcc cag tac acc    192
Thr Glu Gly Thr Thr Tyr Thr Asn Pro Ser Phe Ser Ser Gln Tyr Thr
                    35                  40                  45 gga gca aca aaa gcc gga ttg atc agg ggc tcc tac cat ttc gcg cat    240
Gly Ala Thr Lys Ala Gly Leu Ile Arg Gly Ser Tyr His Phe Ala His
             50                  55                  60 cct tcg tcg tcc aca ggc gca gca cag gca cga tac ttc gtg gca cat    288
Pro Ser Ser Ser Thr Gly Ala Ala Gln Ala Arg Tyr Phe Val Ala His
 65                  70                  75 ggc ggt ggt tgg tcc ggt gat ggt atc acc ttg cct ggt gcg ctc gat    336
Gly Gly Gly Trp Ser Gly Asp Gly Ile Thr Leu Pro Gly Ala Leu Asp
 80                  85                  90                  95 atc gag tat aac cct tcg ggt gcg aca tgt tac ggc ctc tcg acc tcg    384
Ile Glu Tyr Asn Pro Ser Gly Ala Thr Cys Tyr Gly Leu Ser Thr Ser
                    100                 105                 110 tcc atg gtg aac tgg atc gcc gat ttc tcc aac act tat cac tcg ctc    432
Ser Met Val Asn Trp Ile Ala Asp Phe Ser Asn Thr Tyr His Ser Leu
                115                 120                 125 aca ggc agg tac ccc gtc att tac acc act gcc gat tgg tgg cga acc    480
Thr Gly Arg Tyr Pro Val Ile Tyr Thr Thr Ala Asp Trp Trp Arg Thr
            130                 135                 140 tgt acc ggc aac tcc gca tcc ttc gca aac aac tcg cct ctc tgg att    528
Cys Thr Gly Asn Ser Ala Ser Phe Ala Asn Asn Ser Pro Leu Trp Ile
145                 150                 155 gcg cgt tac gcg tcg act atc ggt acg ctc cct gcc gga tgg tcg tac    576
Ala Arg Tyr Ala Ser Thr Ile Gly Thr Leu Pro Ala Gly Trp Ser Tyr
160                 165                 170                 175 gcg acc ttc tgg cag tat gcg gat tcg ggc tcc aac cct ggc gat cag    624
Ala Thr Phe Trp Gln Tyr Ala Asp Ser Gly Ser Asn Pro Gly Asp Gln
                180                 185                 190 gat tac ttc aac ggt gac gca gcg ggt ctc aag cgt ctc gcg aca tcg    672
Asp Tyr Phe Asn Gly Asp Ala Ala Gly Leu Lys Arg Leu Ala Thr Ser
                195                 200                 205 taa                                                                 675
```

<210> SEQ ID NO 37

<211> LENGTH: 224
<212> TYPE: PRT
<213> ORGANISM: Artificial Sequence
<220> FEATURE:
<223> OTHER INFORMATION: Synthetic Construct

<400> SEQUENCE: 37

Met Arg Ile Leu Leu Phe Ile Ala Val Thr Ile Ala Leu Gly Val His
    -15                 -10                 -5

Ala Arg Leu Asn Gly Ile Asp Val Ser Gly Tyr Gln Pro Asn Val Asn
-1   1               5                  10                  15

Trp Ala Thr Val Lys Ala Asn Gly Val Ser Phe Ala Tyr Ile Lys Ala
                20                  25                  30

Thr Glu Gly Thr Thr Tyr Thr Asn Pro Ser Phe Ser Ser Gln Tyr Thr
                35                  40                  45

Gly Ala Thr Lys Ala Gly Leu Ile Arg Gly Ser Tyr His Phe Ala His
                50                  55                  60

Pro Ser Ser Ser Thr Gly Ala Ala Gln Ala Arg Tyr Phe Val Ala His
    65                  70                  75

Gly Gly Gly Trp Ser Gly Asp Gly Ile Thr Leu Pro Gly Ala Leu Asp
80                  85                  90                  95

Ile Glu Tyr Asn Pro Ser Gly Ala Thr Cys Tyr Gly Leu Ser Thr Ser
                    100                 105                 110

Ser Met Val Asn Trp Ile Ala Asp Phe Ser Asn Thr Tyr His Ser Leu
            115                 120                 125

Thr Gly Arg Tyr Pro Val Ile Tyr Thr Thr Ala Asp Trp Trp Arg Thr
        130                 135                 140

Cys Thr Gly Asn Ser Ala Ser Phe Ala Asn Asn Ser Pro Leu Trp Ile
    145                 150                 155

Ala Arg Tyr Ala Ser Thr Ile Gly Thr Leu Pro Ala Gly Trp Ser Tyr
160                 165                 170                 175

Ala Thr Phe Trp Gln Tyr Ala Asp Ser Gly Ser Asn Pro Gly Asp Gln
                180                 185                 190

Asp Tyr Phe Asn Gly Asp Ala Ala Gly Leu Lys Arg Leu Ala Thr Ser
            195                 200                 205

<210> SEQ ID NO 38
<211> LENGTH: 207
<212> TYPE: PRT
<213> ORGANISM: Flammulina velutipes
<220> FEATURE:
<221> NAME/KEY: mat_peptide
<222> LOCATION: (1)..(207)

<400> SEQUENCE: 38

Arg Leu Asn Gly Ile Asp Val Ser Gly Tyr Gln Pro Asn Val Asn Trp
1               5                   10                  15

Ala Thr Val Lys Ala Asn Gly Val Ser Phe Ala Tyr Ile Lys Ala Thr
                20                  25                  30

Glu Gly Thr Thr Tyr Thr Asn Pro Ser Phe Ser Ser Gln Tyr Thr Gly
            35                  40                  45

Ala Thr Lys Ala Gly Leu Ile Arg Gly Ser Tyr His Phe Ala His Pro
    50                  55                  60

Ser Ser Ser Thr Gly Ala Ala Gln Ala Arg Tyr Phe Val Ala His Gly
65                  70                  75                  80

Gly Gly Trp Ser Gly Asp Gly Ile Thr Leu Pro Gly Ala Leu Asp Ile
                85                  90                  95

Glu Tyr Asn Pro Ser Gly Ala Thr Cys Tyr Gly Leu Ser Thr Ser Ser
            100                 105                 110

Met Val Asn Trp Ile Ala Asp Phe Ser Asn Thr Tyr His Ser Leu Thr
        115                 120                 125

Gly Arg Tyr Pro Val Ile Tyr Thr Thr Ala Asp Trp Trp Arg Thr Cys
        130                 135                 140

Thr Gly Asn Ser Ala Ser Phe Ala Asn Asn Ser Pro Leu Trp Ile Ala
145                 150                 155                 160

Arg Tyr Ala Ser Thr Ile Gly Thr Leu Pro Ala Gly Trp Ser Tyr Ala
                165                 170                 175

Thr Phe Trp Gln Tyr Ala Asp Ser Gly Ser Asn Pro Gly Asp Gln Asp
        180                 185                 190

Tyr Phe Asn Gly Asp Ala Ala Gly Leu Lys Arg Leu Ala Thr Ser
        195                 200                 205

<210> SEQ ID NO 39
<211> LENGTH: 208
<212> TYPE: PRT
<213> ORGANISM: Acremonium alcalophilum
<220> FEATURE:
<221> NAME/KEY: mat_peptide
<222> LOCATION: (1)..(208)

<400> SEQUENCE: 39

Arg Ile Pro Gly Phe Asp Ile Ser Gly Trp Gln Pro Thr Thr Asp Phe
1               5                   10                  15

Ala Arg Ala Tyr Ala Asn Gly Asp Arg Phe Val Tyr Ile Lys Ala Thr
            20                  25                  30

Glu Gly Thr Thr Phe Lys Ser Ser Ala Phe Ser Arg Gln Tyr Thr Gly
        35                  40                  45

Ala Thr Gln Asn Gly Phe Ile Arg Gly Ala Tyr His Phe Ala Gln Pro
    50                  55                  60

Ala Ala Ser Ser Gly Ala Ala Gln Ala Arg Tyr Phe Ala Ser Asn Gly
65                  70                  75                  80

Gly Gly Trp Ser Lys Asp Gly Ile Thr Leu Pro Gly Ala Leu Asp Ile
                85                  90                  95

Glu Tyr Asn Pro Asn Gly Ala Thr Cys Tyr Gly Leu Ser Gln Ser Ala
            100                 105                 110

Met Val Asn Trp Ile Glu Asp Phe Val Thr Thr Tyr His Gly Ile Thr
        115                 120                 125

Ser Arg Trp Pro Val Ile Tyr Thr Thr Thr Asp Trp Trp Thr Gln Cys
        130                 135                 140

Thr Gly Asn Ser Asn Arg Phe Ala Asn Arg Cys Pro Leu Trp Ile Ala
145                 150                 155                 160

Arg Tyr Ala Ser Ser Val Gly Thr Leu Pro Asn Gly Trp Gly Phe Tyr
                165                 170                 175

Thr Phe Trp Gln Tyr Asn Asp Lys Tyr Pro Gln Gly Gly Asp Ser Asn
        180                 185                 190

Trp Phe Asn Gly Asp Ala Ser Arg Leu Arg Ala Leu Ala Asn Gly Asp
        195                 200                 205

<210> SEQ ID NO 40
<211> LENGTH: 8
<212> TYPE: PRT
<213> ORGANISM: Artificial Sequence
<220> FEATURE:
<223> OTHER INFORMATION: SEQ ID NO: 40 is the conserved motif F[I/L/V]
      [A/S/K][H/N/S]GGGW.

-continued

```
<220> FEATURE:
<221> NAME/KEY: MISC_FEATURE
<222> LOCATION: (2)..(2)
<223> OTHER INFORMATION: The amino acid in position 2 of the conserved
      motif is either isoleucine (I), leucine (L) or valine (V).
<220> FEATURE:
<221> NAME/KEY: MISC_FEATURE
<222> LOCATION: (3)..(3)
<223> OTHER INFORMATION: The amino acid in position 3 of the conserved
      motif is either alanine (A), serine (S) or lysine (K).
<220> FEATURE:
<221> NAME/KEY: MISC_FEATURE
<222> LOCATION: (4)..(4)
<223> OTHER INFORMATION: The amino acid in position 4 of the conserved
      motif is either histidine (H), asparagine (N) or serine (S).

<400> SEQUENCE: 40

Phe Xaa Xaa Xaa Gly Gly Gly Trp
1               5

<210> SEQ ID NO 41
<211> LENGTH: 7
<212> TYPE: PRT
<213> ORGANISM: Artificial Sequence
<220> FEATURE:
<223> OTHER INFORMATION: SEQ ID NO: 41 is the conserved motif DGXTLPG.
<220> FEATURE:
<221> NAME/KEY: MISC_FEATURE
<222> LOCATION: (3)..(3)
<223> OTHER INFORMATION: The amino acid in position 3 of the conserved
      motif is any amino acid.

<400> SEQUENCE: 41

Asp Gly Xaa Thr Leu Pro Gly
1               5

<210> SEQ ID NO 42
<211> LENGTH: 7
<212> TYPE: PRT
<213> ORGANISM: Artificial Sequence
<220> FEATURE:
<223> OTHER INFORMATION: SEQ ID NO: 42 is the conserved motif
      WWX[Q/T]CTG.
<220> FEATURE:
<221> NAME/KEY: MISC_FEATURE
<222> LOCATION: (3)..(3)
<223> OTHER INFORMATION: The amino acid in position 3 of the conserved
      motif is any amino acid.
<220> FEATURE:
<221> NAME/KEY: MISC_FEATURE
<222> LOCATION: (4)..(4)
<223> OTHER INFORMATION: The amino acid in position 4 of the conserved
      motif is either glutamine (Q) or serine (S).

<400> SEQUENCE: 42

Trp Trp Xaa Xaa Cys Thr Gly
1               5

<210> SEQ ID NO 43
<211> LENGTH: 9
<212> TYPE: PRT
<213> ORGANISM: Artificial Sequence
<220> FEATURE:
<223> OTHER INFORMATION: SEQ ID NO: 43 is the conserved motif F[I/L/V]
      [A/S][H/N/S]GGGWS.
<220> FEATURE:
<221> NAME/KEY: MISC_FEATURE
<222> LOCATION: (2)..(2)
<223> OTHER INFORMATION: The amino acid in position 2 of the conserved
      motif is either isoleucine (I), leucine (L) or valine (V).
<220> FEATURE:
<221> NAME/KEY: MISC_FEATURE
<222> LOCATION: (3)..(3)
```

```
<223> OTHER INFORMATION: The amino acid in position 3 of the conserved
      motif is either alanine (A), serine (S) or lysine (K).
<220> FEATURE:
<221> NAME/KEY: MISC_FEATURE
<222> LOCATION: (4)..(4)
<223> OTHER INFORMATION: The amino acid in position 4 of the conserved
      motif is either histidine (H), asparagine (N) or serine (S).

<400> SEQUENCE: 43

Phe Xaa Xaa Xaa Gly Gly Gly Trp Ser
1               5

<210> SEQ ID NO 44
<211> LENGTH: 37
<212> TYPE: DNA
<213> ORGANISM: Artificial Sequence
<220> FEATURE:
<223> OTHER INFORMATION: Primer

<400> SEQUENCE: 44
acacaactgg ggatccacca tgaagactac gggtgtc                              37

<210> SEQ ID NO 45
<211> LENGTH: 35
<212> TYPE: DNA
<213> ORGANISM: artificial sequence
<220> FEATURE:
<223> OTHER INFORMATION: Primer

<400> SEQUENCE: 45
ccctctagat ctcgagttaa gaacccttgg caaag                                35

<210> SEQ ID NO 46
<211> LENGTH: 38
<212> TYPE: DNA
<213> ORGANISM: artificial sequence
<220> FEATURE:
<223> OTHER INFORMATION: Primer

<400> SEQUENCE: 46
acacaactgg ggatccacca tgaagtctgt tgctgtct                             38

<210> SEQ ID NO 47
<211> LENGTH: 36
<212> TYPE: DNA
<213> ORGANISM: artificial sequence
<220> FEATURE:
<223> OTHER INFORMATION: Primer

<400> SEQUENCE: 47
ccctctagat ctcgagctaa gaagcattcg caatgc                               36

<210> SEQ ID NO 48
<211> LENGTH: 37
<212> TYPE: DNA
<213> ORGANISM: artificial sequence
<220> FEATURE:
<223> OTHER INFORMATION: Primer

<400> SEQUENCE: 48
acacaactgg ggatccacca tgaagctcac gagtgtg                              37

<210> SEQ ID NO 49
<211> LENGTH: 35
<212> TYPE: DNA
<213> ORGANISM: artificial sequence
<220> FEATURE:
```

<223> OTHER INFORMATION: Primer

<400> SEQUENCE: 49
ccctctagat ctcgagttac gaacctctag caagc                     35

<210> SEQ ID NO 50
<211> LENGTH: 37
<212> TYPE: DNA
<213> ORGANISM: artificial sequence
<220> FEATURE:
<223> OTHER INFORMATION: Primer

<400> SEQUENCE: 50
acacaactgg ggatccacca tgatcagggc agttgct                   37

<210> SEQ ID NO 51
<211> LENGTH: 34
<212> TYPE: DNA
<213> ORGANISM: artificial sequence
<220> FEATURE:
<223> OTHER INFORMATION: Primer

<400> SEQUENCE: 51
ccctctagat ctcgagtcag gaacctttag cgaa                      34

<210> SEQ ID NO 52
<211> LENGTH: 40
<212> TYPE: DNA
<213> ORGANISM: artificial sequence
<220> FEATURE:
<223> OTHER INFORMATION: Primer

<400> SEQUENCE: 52
acacaactgg ggatccacca tgaagttcgc atccgtcgcc                40

<210> SEQ ID NO 53
<211> LENGTH: 38
<212> TYPE: DNA
<213> ORGANISM: artificial sequence
<220> FEATURE:
<223> OTHER INFORMATION: Primer

<400> SEQUENCE: 53
agatctcgag aagcttaacc ggcgttggca atcttctt                  38

<210> SEQ ID NO 54
<211> LENGTH: 52
<212> TYPE: DNA
<213> ORGANISM: artificial sequence
<220> FEATURE:
<223> OTHER INFORMATION: Primer

<400> SEQUENCE: 54
acacaactgg ggatccacca tgttgaaaac aattatctat accacccttg cc  52

<210> SEQ ID NO 55
<211> LENGTH: 41
<212> TYPE: DNA
<213> ORGANISM: artificial sequence
<220> FEATURE:
<223> OTHER INFORMATION: Primer

<400> SEQUENCE: 55
agatctcgag aagcttagcc ctttgcaaat cgttgcaatc c              41

```
<210> SEQ ID NO 56
<211> LENGTH: 42
<212> TYPE: DNA
<213> ORGANISM: artificial sequence
<220> FEATURE:
<223> OTHER INFORMATION: Primer

<400> SEQUENCE: 56
acacaactgg ggatccacca tgaagatcac tgccttcccg ct                           42

<210> SEQ ID NO 57
<211> LENGTH: 37
<212> TYPE: DNA
<213> ORGANISM: artificial sequence
<220> FEATURE:
<223> OTHER INFORMATION: Primer

<400> SEQUENCE: 57
agatctcgag aagcttaagc acccttggcg aaggtct                                 37

<210> SEQ ID NO 58
<211> LENGTH: 48
<212> TYPE: DNA
<213> ORGANISM: artificial sequence
<220> FEATURE:
<223> OTHER INFORMATION: Primer

<400> SEQUENCE: 58
acacaactgg ggatccacca tgaagctgtc tctcctcctt attgttgc                     48

<210> SEQ ID NO 59
<211> LENGTH: 41
<212> TYPE: DNA
<213> ORGANISM: artificial sequence
<220> FEATURE:
<223> OTHER INFORMATION: Primer

<400> SEQUENCE: 59
agatctcgag aagcttaacc tagggccatt ctcttcaacc c                            41

<210> SEQ ID NO 60
<211> LENGTH: 48
<212> TYPE: DNA
<213> ORGANISM: artificial sequence
<220> FEATURE:
<223> OTHER INFORMATION: Primer

<400> SEQUENCE: 60
acacaactgg ggatccacca tgaagtcttt tggtgttatt gctaccgg                     48

<210> SEQ ID NO 61
<211> LENGTH: 39
<212> TYPE: DNA
<213> ORGANISM: artificial sequence
<220> FEATURE:
<223> OTHER INFORMATION: Primer

<400> SEQUENCE: 61
agatctcgag aagcttagcc tctggcgatt ctctgaagc                               39
```